(12) United States Patent
Mannion et al.

(10) Patent No.: US 8,759,522 B2
(45) Date of Patent: *Jun. 24, 2014

(54) INHIBITORS OF PROTEIN TYROSINE KINASE ACTIVITY

(75) Inventors: Michael Mannion, Montreal (CA); Stephane Raeppel, St-Lazare (CA); Stephen William Claridge, Montreal (CA); Frederic Gaudette, Laval (CA); Lijie Zhan, Montreal (CA); Ljubomir Isakovic, Beaconsfield (CA); Oscar Mario Saavedra, Montreal (CA); Tetsuyuki Uno, Okayama (JP); Masashi Kishida, Hyogo (JP); Arkadii Vaisburg, Kirkland (CA)

(73) Assignee: Methylgene Inc., Montreal (CA)

( * ) Notice: Subject to any disclaimer, the term of this patent is extended or adjusted under 35 U.S.C. 154(b) by 151 days.

This patent is subject to a terminal disclaimer.

(21) Appl. No.: 12/964,289

(22) Filed: Dec. 9, 2010

(65) Prior Publication Data

US 2011/0077240 A1 Mar. 31, 2011

Related U.S. Application Data

(63) Continuation of application No. 12/920,676, filed as application No. PCT/CA2009/000228 on Feb. 27, 2009.

(60) Provisional application No. 61/034,005, filed on Mar. 5, 2008.

(51) Int. Cl.
*C07D 513/04* (2006.01)
*A61K 31/4365* (2006.01)

(52) U.S. Cl.
USPC ............................ 546/114; 514/301

(58) Field of Classification Search
USPC ............................ 546/114; 514/301
See application file for complete search history.

(56) References Cited

U.S. PATENT DOCUMENTS

| 6,232,320 | B1 | 5/2001 | Stewart et al. |
|---|---|---|---|
| 6,448,261 | B1 | 9/2002 | Bakthavatchalam et al. |
| 6,492,383 | B1 | 12/2002 | Munchhof et al. |
| 6,833,456 | B2 | 12/2004 | Romines, III et al. |
| 6,995,171 | B2 | 2/2006 | Autry et al. |
| 2002/0004511 | A1 | 1/2002 | Luzzio et al. |
| 2005/0116028 | A1 | 6/2005 | Cohen et al. |
| 2005/0239820 | A1 | 10/2005 | Borzilleri et al. |
| 2005/0245547 | A1 | 11/2005 | Kim et al. |
| 2005/0288290 | A1 | 12/2005 | Borzilleri et al. |
| 2006/0004006 | A1 | 1/2006 | Borzilleri et al. |
| 2006/0074056 | A1 | 4/2006 | Vaisburg et al. |
| 2006/0211695 | A1 | 9/2006 | Borzilleri et al. |
| 2006/0252777 | A1 | 11/2006 | Kim et al. |
| 2006/0287343 | A1 | 12/2006 | Saavedra et al. |
| 2007/0004675 | A1 | 1/2007 | Saavedra et al. |
| 2007/0197537 | A1 | 8/2007 | Blake et al. |
| 2009/0270391 | A1 | 10/2009 | Kubo et al. |

FOREIGN PATENT DOCUMENTS

| CA | 2309690 A1 | 5/1999 |
|---|---|---|
| CA | 2451678 A1 | 1/2003 |
| CA | 2477651 A1 | 10/2003 |
| CA | 2502614 A1 | 6/2004 |
| CA | 2571680 | 1/2006 |
| CA | 2603125 | 10/2006 |
| CA | 2605680 | 11/2006 |
| CA | 2611370 | 11/2006 |
| WO | WO 99/24440 | 5/1999 |
| WO | WO 99/62908 | 12/1999 |
| WO | WO 00/75145 | 12/2000 |
| WO | WO 01/94353 | 12/2001 |
| WO | WO 03/000194 | 1/2003 |
| WO | WO 03/000688 | 1/2003 |
| WO | WO 03/074529 | 9/2003 |
| WO | WO 2004/048386 | 6/2004 |
| WO | WO 2005/009348 | 2/2005 |
| WO | WO 2005/021554 | 3/2005 |
| WO | WO 2005/073224 | 8/2005 |
| WO | WO 2005/116028 | 8/2005 |
| WO | WO 2005/117867 | 12/2005 |
| WO | WO 2005/121125 | 12/2005 |
| WO | WO 2006/004636 | 1/2006 |
| WO | WO 2006/004833 | 1/2006 |
| WO | WO 2006/010264 | 2/2006 |
| WO | WO 2006/014325 | 2/2006 |
| WO | WO 2006/036266 | 4/2006 |
| WO | WO 2006/104161 | 10/2006 |
| WO | WO 2006/108059 | 10/2006 |
| WO | WO 2006/116713 | 11/2006 |
| WO | WO 2007/054831 | 5/2007 |

(Continued)

OTHER PUBLICATIONS

Fan et al., "Controlling the Vasculature: Angiogenesis . . . ", Trends Pharmacol. Sci. 16:57-66 (1995).
Folkman, J., "Angiogenesis in Cancer, Vascular, Rheumatoid and Other . . . ", Nat. Med. 1:27-31 (1995).
Jakeman et al., "Developmental Expression of Binding Sites . . . ", Endocrinology, 133:848-859 (1993).
Connolly et al., "Human Vascular Permeability Factor . . . ", J. Biol. Chem. 264:20017-20024 (1989).
Plowman et al., "Receptor Tyrosine Kinases as Targets for . . . ", Drug News Perspect. 7:334-339 (1994).
Strawn et al., "Tyrosine Kinases in Disease: Overview . . . ", Exp. Opin. Invest. Drugs 7:553-573 (1998).

(Continued)

*Primary Examiner* — David K O Dell
(74) *Attorney, Agent, or Firm* — Wood, Phillips, Katz, Clark & Mortimer

(57) ABSTRACT

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling. The invention also provides compounds, compositions and methods for treating cell proliferative diseases and conditions and opthalmological diseases, disorders and conditions.

10 Claims, No Drawings

(56) References Cited

FOREIGN PATENT DOCUMENTS

| WO | WO 2007/107005 | | 9/2007 |
|----|----------------|----|--------|
| WO | WO 2008/063202 | | 5/2008 |
| WO | WO 2009026717 | A1 * | 3/2009 |

OTHER PUBLICATIONS

Shawver et al., "Receptor Tyrosine Kinases as Targets for . . . ", Drug Discov. Today 2:50-63 (1997).
De Vries et al., "The FMS-Like Tyrosine Kinases, a Receptor . . . " Science 255:989-991 (1992).
Terman et al., "Identification of the KDR . . . ", Biochem. Biophys. Res. Commun. 187:1579-1586 (1992).
Plate et al., "Vascular Endothelial Growth Factor and Glioma . . . ", Int. J. Cancer 59:520-529 (1994).
Fuh et al., "Requirements for Binding and Signaling of the . . . ", J. Biol. Chem. 273:11197-11204 (1998).
Wheeler-Jones et al., "Vascular Endothelial Growth . . . ", FEBS Lett. 420:28-32 (1997).
Kim et al., "Inhibition of Vascular Endothelial Growth . . . ", Nature (Lond.) 362:841-844 (1993).
Kanai et al., "Anti-Tumor and Anti-Metastatic Effects . . . ", Int. J. Cancer 77:933-936 (1998).
Zhu et al., "Inhibition of Vascular Endothelial Growth Factor . . . ", Cancer Res. 58:3209-3214 (1998).
Siemeister et al., "An Antagonistic Vascular Endo . . . ", Proc. Natl. Acad. Sci. USA 95:4625-4629 (1998).
Lin, P. et al. "Inhibition of Tumor Growth by Targeting . . . ", Cell Growth Differ. 9;49-58 (1998).
Cheng et al., "Suppression of Glioblastoma Angiogenicity . . . ", Proc. Natl. Acad. Sci. USA 93:8502-8507 (1996).
Millauer et al. "Dominant-Negative Inhibition of Flk-1 Suppresses . . . ", Cancer Res. 56:1615-1620 (1996).
Pennacchietti et al., "Hypoxia Promotes Invasive Growth by Transcriptional Activation of the Met Protooncogene", Cancer Cell. 3(4):347-361 (2003).
Camps et al., "Fibroblast-Mediate Acceleration of Human Epithelial Tumor Growth in Vivo", Proc. Natl. Acad. Sci. USA 87:75-9 (1990).
Nakamura et al., "Induction of Hepatocyte Growth Factor in Fibroblasts by Tumor-Derived Factors Affects Invasive Growth of Tumor Cells: In Vitro Analysis of Tumor-Stromal Interactions", Cancer Res. 57:3305-3313 (1997).
Nishimura et al., "Regulation of Invasive Potential of Human . . . ", Int. J. Urol. 5:276-281 (1998).
Bae-Jump et al., "Hepatocyte Growth Factor (HGF) Induces . . . ", Gynecol. Oncol. 73:265-272 (1999).
Nakamura et al., "A Partial Purification and Characterization . . . ",Bioch. Bio. Res. Com. 122:1450-9 (1984).
Nakamura et al., "Molecular Cloning and Expression of Human . . . ", Nature 342:440-443 (1989).
Ebert et al., "Coexpression of the C-Met Proto-oncogene and . . . ", Cancer Res. 54:5775-5778 (1994).
DiRenzo et al., "Expression of the Met-HGF Receptor in normal . . . ", Oncogene 6:1997-2003 (1991).
DiRenzo et al., "Expression of the Met/Hepatocyte Growth Factor . . . " Cancer Res. 11:1129-1138 (1995).
Delehedde et al., "Hepatocyte Growth Factor/Scatter Factor . . . " Eur. J. Biochem. 269:4423-4429 (2001).
Bardelli et al., "Concomitant Activation of Pathways Downstream . . . ", Oncogene 18:1139-1146 (1999).
Saucier et al., "The SHC Adaptor Protein is Critical for . . . " Nat. Acad. Sci. USA 101(8):2345-2350 (2004).
Evans et al., "Addition of Lithiated 9-Deazapurine Derivatives", J. Org. Chem. 66(17):5723-5730 (2001).
Tsou et al., "6-Substituted-4-(3-bromophenylamino) Quinazolines . . . ", J. Med. Chem. 44:2719-2734 (2001).
Cliff et al., "Synthesis of 4,4'-Biimidazoles", Synthesis pp. 681-682 (1994).
He et al., "A Convenient Synthesis of 1,4-Disubstituted . . . ", Tetrahedron Lett. 45(28):5529-5532 (2004).
O'Connell et al., "Convenient Synthesis of Methyl 1-Methyl-2,4-Dibromo . . . ", Synthesis pp. 767-771 (1988).
Gutschow et al., "2-(Diethylamino)Thieno[1,3]Oxazin-4 . . . ", J. Med. Chem. 42(26):5437-5447 (1999).
Robba et al., "Thienopyrimidines", Bull Soc. Chem. Fr. 587-591 (1975).
Hodgson et al., "The Nitrosation of Phenols. Part VII . . . ", J. Chem. Soc. pp. 2775-2778 (1929).
Smith et al., "Cyclization of Isothiocyanates as a Route to . . . ", J. Org. Chem. pp. 2261-2265 (1964).
Claridge et al., "Discovery of a novel and potent series of thieno[3,2-*b*]pyridine-based inhibitors of c-Met and VEGFR2 tyrosine kinases," Bioorganic and Medicinal Chemistry Letters, 18 (2008) 2793-2798.
Antilla et al., "The Copper-Catalyzed N-Arylation of Indoles", JACS 124:11684-11688 (2002).
Zhang et al., "A General Method for the Preparation of . . . ", J. Org. Chem. 67:2345-2347 (2002).
Almansa et al., "Synthesis and SAR of a New Series of COX-2 . . . ", J. Med. Chem. 44:350-361 (2001).
Hill et al., "Dialkylacetyl Biurets", JACS 62:1595-1596 (1940).
Lashkari et al., "Vascular Endothelial Growth Factor and Hepatocyte Growth Factor Levels are Differentially Elevated in Patients with Advanced Retinopathy of Prematurity," American Journal of Pathology, 156.1337-44 (2000).
Iruela-Arispe et al., "Participation of glomerular endothelial cells in the capillary repair of glomerulonephritis," The American Journal of Pathology, 147:1715-27 (1995).
Shafiee A. et al., "Synthesis and Antihypertensive Activities of New 1,4-Dihydropyridine Containing Nitroimidazolyl Substituent with a Nitrooxy Group at the 3-Ester Position" Arch.Pharm.Pharm.Med. Chem 2002, 2, 69-76.
Klemm et al., "Chemistry of Thienopyridines; Synthetic Routes to 5- and 7-Substituted Thieno[3,2-b]pyridines from the N-Oxide" J. Heterocyclic Chem. 22, 1985, 1249-1252.

* cited by examiner

INHIBITORS OF PROTEIN TYROSINE KINASE ACTIVITY

RELATED APPLICATIONS

This application is a continuation of U.S. application Ser. No. 12/920,676, filed Sep. 2, 2010, which is a U.S. National Stage Application based on International Application PCT/CA2009/000228, filed on Feb. 27, 2009, which claims the benefit of U.S. Provisional Application Ser. No. 61/034,005, filed Mar. 5, 2008. The entire teachings of the above-referenced application is incorporated herein by reference.

BACKGROUND OF THE INVENTION

1. Field of the Invention

This invention relates to compounds that inhibit protein tyrosine kinase activity. In particular the invention relates to compounds that inhibit the protein tyrosine kinase activity of growth factor receptors, resulting in the inhibition of receptor signaling, for example, the inhibition of VEGF receptor signaling and HGF receptor signaling. More particularly, the invention relates to compounds, compositions and methods for the inhibition of VEGF receptor signaling and HGF receptor signaling.

2. Summary of the Related Art

Tyrosine kinases may be classified as growth factor receptor (e.g. EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. These tyrosine kinases have diverse biological activity. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

Angiogenesis is an important component of certain normal physiological processes such as embryogenesis and wound healing, but aberrant angiogenesis contributes to some pathological disorders and in particular to tumor growth. VEGF-A (vascular endothelial growth factor A) is a key factor promoting neovascularization (angiogenesis) of tumors. VEGF induces endothelial cell proliferation and migration by signaling through two high affinity receptors, the fms-like tyrosine kinase receptor, Flt-1, and the kinase insert domain-containing receptor, KDR. These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain. The kinase activity autophosphorylates cytoplasmic receptor tyrosine residues, which then serve as binding sites for molecules involved in the propagation of a signaling cascade. Although multiple pathways are likely to be elucidated for both receptors, KDR signaling is most extensively studied, with a mitogenic response suggested to involve ERK-1 and ERK-2 mitogen-activated protein kinases.

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies, receptor antagonists, soluble receptors, antisense constructs and dominant-negative strategies.

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics.

The HGF (hepatocyte growth factor) and the HGF receptor, c-met, are implicated in the ability of tumor cells to undermine the activity of VEGF inhibition. HGF derived from either stromal fibroblasts surrounding tumor cells or expressed from the tumor itself has been suggested to play a critical role in tumor angiogenesis, invasion and metastasis. For example, invasive growth of certain cancer cells is drastically enhanced by tumor-stromal interactions involving the HGF/c-Met (HGF receptor) pathway. HGF, which was originally identified as a potent mitogen for hepatocytes is primarily secreted from stromal cells, and the secreted HGF can promote motility and invasion of various cancer cells that express c-Met in a paracrine manner. Binding of HGF to c-Met leads to receptor phosphorylation and activation of Ras/mitogen-activated protein kinase (MAPK) signaling pathway, thereby enhancing malignant behaviors of cancer cells. Moreover, stimulation of the HGF/c-met pathway itself can lead to the induction of VEGF expression, itself contributing directly to angiogenic activity.

Thus, anti-tumor anti-angiogenic strategies or approaches that target VEGF/VEGFr signaling or HGF/c-met signaling may represent improved cancer therapeutics.

Tyrosine kinases also contribute to the pathology of opthalmological diseases, disorders and conditions, such as age-related macular degeneration (AMD) and diabetic retinopathy (DR). Blindness from such diseases has been linked to anomalies in retinal neovascularization. The formation of new blood vessels is regulated by growth factors such as VEGF and HGF that activate receptor tyrosine kinases resulting in the initiation of signaling pathways leading to plasma leakage into the macula, causing vision loss. Kinases are thus attractive targets for the treatment of eye diseases involving neovascularization.

Thus, there is a need to develop a strategy for controlling neovascularization of the eye and to develop a strategy for the treatment of ocular diseases.

Here we describe small molecules that are potent inhibitors of protein tyrosine kinase activity.

BRIEF SUMMARY OF THE INVENTION

The present invention provides new compounds and methods for treating a disease responsive to inhibition of kinase activity, for example a disease responsive to inhibition of protein tyrosine kinse activity, for example a disease responsive to inhibition of protein tyrosine kinase activity of growth factor receptors, for example a disease responsive to inhibition of receptor type tyrosine kinase signaling, or for example, a disease responsive to inhibition of VEGF receptor signaling. In one embodiment the disease is a cell proliferative disease. In another embodiment, the disease is an opthalmological disease. The compounds of the invention are inhibitors of kinase activity, such as protein tyrosine kinase activity, for example protein tyrosine kinase activity of growth factor receptors, or for example receptor type tyrosine kinase signaling.

In a first aspect, the invention provides compounds of Formula (I) that are useful as kinase inhibitors:

and N-oxides, hydrates, solvates, pharmaceutically acceptable salts, prodrugs and complexes thereof, and racemic and scalemic mixtures, diastereomers and enantiomers thereof, wherein D, M, Z, Ar and G are as defined herein. Because compounds of the present invention are useful as kinase inhibitors they are, therefore, useful research tools for the study of the role of kinases in both normal and disease states. In some embodiments, the invention provides compounds that are useful as inhibitors of VEGF receptor signaling and, therefore, are useful research tools for the study of of the role of VEGF in both normal and disease states.

Reference to "a compound of the formula (I)", (or equivalently, "a compound according to the first aspect", or "a compound of the present invention", and the like), herein is understood to include reference to N-oxides, hydrates, solvates, pharmaceutically acceptable salts, prodrugs and complexes thereof, and racemic and scalemic mixtures, diastereomers, enantiomers and tautomers thereof, unless otherwise indicated.

In a second aspect, the invention provides compositions comprising a compound according to the present invention and a pharmaceutically acceptable carrier, excipient or diluent. For example, the invention provides compositions comprising a compound that is an inhibitor of VEGF receptor signaling, or a pharmaceutically acceptable salt thereof, and a pharmaceutically acceptable carrier, excipient, or diluent.

In a third aspect, the invention provides a method of inhibiting kinase activity, for example protein tyrosine kinase, for example tyrosine kinase activity of a growth factor receptor, the method comprising contacting the kinase with a compound according to the present invention, or with a composition according to the present invention. In some embodiments of this aspect, the invention provides a method of inhibiting receptor type tyrosine kinase signaling, for example inhibiting VEGF receptor signaling. Inhibition can be in a cell or a multicellular organism. If in a cell, the method according to this aspect of the invention comprises contacting the cell with a compound according to the present invention, or with a composition according to the present invention. If in a multicellular organism, the method according to this aspect of the invention comprises administering to the organism a compound according to the present invention, or a composition according to the present invention. In some embodiments the organism is a mammal, for example a primate, for example a human.

In a fourth aspect, the invention provides a method of inhibiting angiogenesis, the method comprising administering to a patient in need thereof a therapeutically effective amount of a compound according to the present invention, or a therapeutically effective amount of a composition according to the present invention. In some embodiments of this aspect, the angiogenesis to be inhibited is involved in tumor growth. In some other embodiments the angiogenesis to be inhibited is retinal angiogenesis. In some embodiments of this aspect, the patient is a mammal, for example a primate, for example a human.

In a fifth aspect, the invention provides a method of treating a disease responsive to inhibition of kinase activity, for example a disease responsive to inhibition of protein tyrosine kinase activity, for example a disease responsive to inhibition of protein tyrosine kinase activity of growth factor receptors. In some embodiments of this aspect, the invention provides a method of treating a disease responsive to inhibition of receptor type tyrosine kinase signaling, for example a disease responsive to inhibition of VEGF receptor signaling, the method comprising administering to an organism in need thereof a therapeutically effective amount of a compound according to the present invention, or a composition according to the present invention. In some embodiments of this aspect, the organism is a mammal, for example a primate, for example a human.

In a sixth aspect, the invention provides a method of treating a cell proliferative disease, the method comprising administering to a patient in need thereof a therapeutically effective amount of a compound according to the present invention, or a therapeutically effective amount of a composition according to the present invention. In some embodiments of this aspect, the cell proliferative disease is cancer. In some embodiments, the patient is a mammal, for example a primate, for example a human.

In a seventh aspect, the invention provides a method of treating an ophthalmic disease, disorder or condition, the method comprising administering to a patient in need thereof a therapeutically effective amount of a compound according to the present invention, or a therapeutically effective amount of a composition according to the present invention. In some embodiments of this aspect, the disease is caused by choroidal angiogenesis. In some embodiments of this aspect, the patient is a mammal, for example a primate, for example a human.

In an eighth aspect, the invention provides for the use of a compound according to the present invention for or in the manufacture of a medicament to inhibit kinase activity, for example to inhibit protein tyrosine kinase activity, for example to inhibit protein tyrosine kinase activity of growth factor receptors. In some embodiments of this aspect, the invention provides for the use of a compound according to the present invention for or in the manufacture of a medicament to inhibit receptor type tyrosine kinase signaling, for example to inhibit VEGF receptor signaling. In some embodiments of this aspect, the invention provides for the use of a compound according to the present invention for or in the manufacture of a medicament to treat a disease responsive to inhibition of kinase activity. In some embodiments of this aspect, the disease is responsive to inhibition of protein tyrosine kinase activity, for example inhibition of protein tyrosine kinase activity of growth factor receptors. In some embodiments of this aspect, the disease is responsive to inhibition of receptor type tyrosine kinase signaling, for example VEGF receptor signaling. In some embodiments, the disease is a cell proliferative disease, for example cancer. In some embodiments of this aspect, the disease is an ophthalmic disease, disorder or condition. In some embodiments of this aspect, the ophthalmic disease, disorder or condition is caused by choroidal angiogenesis. In some embodiments of this aspect, the disease is age-related macular degeneration, diabetic retinopathy or retinal edema.

In a nineth aspect, the invention provides for the use of a compound according to the present invention, or a composition thereof, to inhibit kinase activity, for example to inhibit receptor type tyrosine kinase activity, for example to inhibit protein tyrosine kinase activity of growth factor receptors. In some embodiments of this aspect, the invention provides for the use of a compound according to the present invention, or a composition thereof, to inhibit receptor type tyrosine kinase signaling, for example to inhibit VEGF receptor signaling.

In a tenth aspect, the invention provides for the use of a compound according to the present invention, or a composition thereof, to treat a disease responsive to inhibition of kinase activity, for example a disease responsive to inhibition of protein tyrosine kinase activity, for example a disease responsive to inhibition or protein tyrosine kinase activity of growth factor receptors. In some embodiments of this aspect, the invention provides for the use of a compound according to the present invention, or a composition thereof, to treat a disease responsive to inhibition of receptor type tyrosine kinase signaling, for example a disease responsive to inhibition of VEGF receptor signaling. In some embodiments of this aspect, the disease is a cell proliferative disease, for example cancer. In some embodiments of this aspect, the disease is an ophthalmic disease, disorder or condition. In some embodiments of this aspect, the ophthalmic disease, disorder or condition is caused by choroidal angiogenesis.

The foregoing merely summarizes some aspects of the invention and is not intended to be limiting in nature. These aspects and other aspects and embodiments are described more fully below.

DETAILED DESCRIPTION

The invention provides compounds, compositions and methods for inhibiting kinase activity, for example protein tyrosine kinase activity, for example receptor protein kinase activity, for example the VEGF receptor KDR. The invention also provides compounds, compositions and methods for inhibiting angiogenesis, treating a disease responsive to inhibition of kinase activity, treating cell proliferative diseases and conditions and treating ophthalmic diseases, disorders and conditions. The patent and scientific literature referred to herein reflects knowledge that is available to those with skill in the art. The issued patents, published patent applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which a divalent moiety is required and is stated as being "aryl," those skilled in the art will understand that the term "aryl" refers to the corresponding divalent moiety, arylene. All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$"heterocyclyl or "$C_n$-$C_m$"heteroaryl means a heterocyclyl or heteroaryl having from "n" to "m" annular atoms, where "n" and "m" are integers. Thus, for example, a $C_5$-$C_6$heterocyclyl is a 5- or 6-membered ring having at least one heteroatom, and includes pyrrolidinyl ($C_5$) and piperazinyl and piperidinyl ($C_6$); $C_6$heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$ hydrocarbyl" includes a covalent bond, methyl, ethyl, ethenyl, ethynyl, propyl, propenyl, propynyl, and cyclopropyl.

The term "alkyl" is intended to mean a straight chain or branched aliphatic group having from 1 to 12 carbon atoms, alternatively 1-8 carbon atoms, and alternatively 1-6 carbon atoms. In some embodiments, the alkyl groups have from 2 to 12 carbon atoms, alternatively 2-8 carbon atoms and alternatively 2-6 carbon atoms. Examples of alkyl groups include, without limitation, methyl, ethyl, propyl, isopropyl, butyl, isobutyl, sec-butyl, tert-butyl, pentyl, hexyl and the like. A "$C_0$"alkyl (as in "$C_0$-$C_3$alkyl") is a covalent bond.

The term "alkenyl" is intended to mean an unsaturated straight chain or branched aliphatic group with one or more carbon-carbon double bonds, having from 2 to 12 carbon atoms, alternatively 2-8 carbon atoms, and alternatively 2-6 carbon atoms. Examples alkenyl groups include, without limitation, ethenyl, propenyl, butenyl, pentenyl, and hexenyl.

The term "alkynyl" is intended to mean an unsaturated straight chain or branched aliphatic group with one or more carbon-carbon triple bonds, having from 2 to 12 carbon atoms, alternatively 2-8 carbon atoms, and alternatively 2-6 carbon atoms. Examples of alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Examples of alkylene groups include, without limitation, methylene, ethylene, propylene, and butylene. Examples of alkenylene groups include, without limitation, ethenylene, propenylene, and butenylene. Examples of alkynylene groups include, without limitation, ethynylene, propynylene, and butynylene.

The term "carbocycle" as employed herein is intended to mean a cycloalkyl or aryl moiety.

The term "cycloalkyl" is intended to mean a saturated, partially unsaturated or unsaturated mono-, bi-, tri- or polycyclic hydrocarbon group having about 3 to 15 carbons, alternatively having 3 to 12 carbons, alternatively 3 to 8 carbons, alternatively 3 to 6 carbons, and alternatively 5 or 6 carbons. In some embodiments, the cycloalkyl group is fused to an aryl, heteroaryl or heterocyclic group. Examples of cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated, partially unsaturated or unsaturated, straight chain or branched aliphatic group, wherein one or more carbon atoms in the group are independently replaced by a heteroatom selected from the group consisting of O, S, and N.

The term "aryl" is intended to mean a mono-, bi-, tri- or polycyclic aromatic moiety, comprising one to three aromatic rings. In some embodiments the aryl is a $C_6$-$C_{14}$aromatic moiety, alternatively the aryl group is a $C_6$-$C_{10}$aryl group, alternatively a $C_6$ aryl group. Examples of aryl groups include, without limitation, phenyl, naphthyl, anthracenyl, and fluorenyl.

The terms "aralkyl" or "arylalkyl" are intended to mean a group comprising an aryl group covalently linked to an alkyl group. If an aralkyl group is described as "optionally substituted", it is intended that either or both of the aryl and alkyl moieties may independently be optionally substituted or unsubstituted. In some embodiments, the aralkyl group is ($C_1$-$C_6$)alk($C_6$-$C_{10}$)aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, alternatively 3 to 8 atoms, alternatively 4 to 7 atoms, alternatively 5 or 6 atoms wherein one or more atoms, for example 1 or 2 atoms, are independently selected from the group consisting of N, O, and S, the remaining ring-constituting atoms being carbon atoms. The ring structure may be saturated, unsaturated or partially unsaturated. In some embodiments, the heterocyclic group is non-aromatic, in which case the group is also known as a heterocycloalkyl. In a bicyclic or polycyclic structure, one or more rings may be aromatic; for example, one ring of a bicyclic heterocycle or one or two rings of a tricyclic heterocycle may be aromatic, as in indan and 9,10-dihydro anthracene. Examples of heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, morpholino, thienyl, pyridyl, 1,2,3-triazolyl, imidazolyl, isoxazolyl, pyrazolyl, piperazino, piperidyl, piperidino, morpholinyl, homopiperazinyl, homopiperazino, thiomorpholinyl, thiomorpholino, tetrahydropyrrolyl, and azepanyl. In some embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In some embodiments, the heterocyclic group is a heteroaryl group. As used herein, the term "heteroaryl" is intended to mean a mono-, bi-, tri- or polycyclic group having 5 to 14 ring atoms, alternatively 5, 6, 9, or 10 ring atoms; having for example 6, 10, or 14 pi electrons shared in a cyclic array; and having, in addition to carbon atoms, between one or more heteroatoms independently selected from the group consisting of N, O, and S. For example, a heteroaryl group include, without limitation, pyrimidinyl, pyridinyl, benzimidazolyl, thienyl, benzothiazolyl, benzofuranyl and indolinyl. Other examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Examples of heterocyclyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as fuor [2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolinyl, 4H-quinolizinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

The term "azolyl" as employed herein is intended to mean a five-membered saturated or unsaturated heterocyclic group containing two or more hetero-atoms, as ring atoms, selected from the group consisting of nitrogen, sulfur and oxygen, wherein at least one of the hetero-atoms is a nitrogen atom. Examples of azolyl groups include, but are not limited to, optionally substituted imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, alternatively from one to three, alternatively one or two, independently selected non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

Examples of substituents, which are themselves not further substituted (unless expressly stated otherwise) are:

(a) halo, cyano, oxo, carboxy, formyl, nitro, amino, amidino, guanidino, (b) $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_8$alkyl, $C_1$-$C_8$alkenyl, $C_1$-$C_8$alkoxy, $C_1$-$C_8$alkyamino, $C_1$-$C_8$alkoxycarbonyl, aryloxycarbonyl, $C_2$-$C_8$acyl, $C_2$-$C_8$acylamino, $C_1$-$C_8$alkylthio, arylalkylthio, arylthio, $C_1$-$C_8$alkylsulfinyl, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$heterocycle, $C_5$-$C_{15}$heteroaryl or any of these rings fused or spiro-fused to a cycloalkyl, heterocyclyl, or aryl, wherein each of the foregoing is further optionally substituted with one more moieties listed in (a), above; and (c) —$(CR^{32}R^{33})_s$—$NR^{30}R^{31}$, wherein s is from 0 (in which case the nitrogen is directly bonded to the moiety that is substituted) to 6, $R^{32}$ and $R^{33}$ are each independently hydrogen, halo, hydroxyl or $C_1$-$C_4$alkyl, and $R^{30}$ and $R^{31}$ are each independently hydrogen, cyano, oxo, hydroxyl, $C_1$-$C_8$alkyl, $C_1$-$C_8$heteroalkyl, $C_1$-$C_8$alkenyl, carboxamido, $C_1$-$C_3$alkyl-carboxamido, carboxamido-$C_1$-$C_3$alkyl, amidino, $C_2$-$C_8$hydroxyalkyl, $C_1$-$C_3$alkylaryl, $C_1$-$C_3$alkylheteroaryl, heteroaryl-$C_1$-$C_3$alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$alkyl, $C_2$-$C_8$alkoxy, $C_2$-$C_8$alkoxy-$C_1$-$C_4$alkyl, $C_1$-$C_8$alkoxycarbonyl, aryloxycarbonyl, aryl-$C_1$-$C_3$alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein $X^{30}$ is selected from the group consisting of $C_1$-$C_8$alkyl, $C_2$-$C_8$alkenyl-, $C_2$-$C_8$alkynyl-, —$C_0$-$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—$C_0$-$C_3$alkyl-, —HO—$C_0$-$C_3$alkyl-, $C_0$-$C_4$alkyl-N($R^{30}$)—$C_0$-$C_3$alkyl-, N($R^{30}$)($R^{31}$)—$C_0$-$C_3$alkyl-, N($R^{30}$)($R^{31}$)—$C_0$-$C_3$alkenyl-, N($R^{30}$)($R^{31}$)—$C_0$-$C_3$alkynyl-, (N($R^{30}$)($R^{31}$))$_2$—C=N—, $C_0$-$C_3$alkyl-S(O)$_{0-2}$—$C_0$-$C_3$alkyl-, CF$_3$-$C_0$-$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{30}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and $Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, N($R^{30}$)—C(NR$^{30}$)—N($R^{31}$)—, —N($R^{30}$)—C(NR$^{31}$)—, —C(NR$^{31}$)—N($R^{30}$)—, —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

A moiety that is substituted is one in which one or more (for example one to four, alternatively from one to three and alternatively one or two), hydrogens have been independently replaced with another chemical substituent. As a non-limiting example, substituted phenyls include 2-flurophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In some embodiments, a hydrocarbyl, heteroalkyl, heterocyclic and/or aryl group is unsubstituted.

In some embodiments, a hydrocarbyl, heteroalkyl, heterocyclic and/or aryl group is substituted with from 1 to 3 independently selected substituents.

Examples of substituents on alkyl groups include, but are not limited to, hydroxyl, halogen (e.g., a single halogen substituent or multiple halo substituents; in the latter case, groups such as CF$_3$ or an alkyl group bearing Cl$_3$), oxo, cyano, nitro, alkyl, cycloalkyl, alkenyl, cycloalkenyl, alkynyl, heterocycle, aryl, —OR$^a$, —SR$^a$, —S(=O)R$^e$, —S(=O)$_2$R$^e$, —P(=O)$_2$R$^3$, —S(=O)$_2$OR$^e$, —P(=O)$_2$OR$^e$, —NR$^b$R$^c$, —NR$^b$S(=O)$_2$R$^e$, —NR$^b$P(=O)$_2$R$^e$, —S(=O)$_2$NR$^b$R$^c$, —P(=O)$_2$NR$^b$R$^c$, —C(=O)OR$^a$, —C(=O)R$^a$, —C(=O)NR$^b$R$^c$, —OC(=O)R$^a$, —OC(=O)NR$^b$R$^c$, —NR$^b$C(=O)OR$^e$, —NR$^d$C(=O)NR$^b$R$^c$, —NR$^d$S(=O)$_2$NR$^b$R$^c$, —NR$^d$P(=O)$_2$NR$^b$R$^c$, —NR$^b$C(=O)R$^a$ or —NR$^b$P(=O)$_2$R$^e$, wherein R$^a$ is hydrogen, alkyl, cycloalkyl, alkenyl, cycloalkenyl, alkynyl, heterocycle or aryl; R$^b$, R$^c$ and R$^d$ are independently hydrogen, alkyl, cycloalkyl, heterocycle or aryl, or said R$^b$ and R$^c$ together with the N to which they are bonded optionally form a heterocycle; and R$^e$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Examples of substituents on alkenyl and alkynyl groups include, but are not limited to, alkyl or substituted alkyl, as well as those groups recited as examples of alkyl substituents.

Examples of substituents on cycloalkyl groups include, but are not limited to, nitro, cyano, alkyl or substituted alkyl, as well as those groups recited above as examples of alkyl substituents. Other examples of substituents include, but are not limited to, Spiro-attached or fused cyclic substituents, for example, spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on cycloalkenyl groups include, but are not limited to, nitro, cyano, alkyl or substituted alkyl, as well as those groups recited as examples of alkyl substituents. Other examples of substituents include, but are not limited to, spiro-attached or fused cyclic substituents, for examples spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on aryl groups include, but are not limited to, nitro, cycloalkyl or substituted cycloalkyl, cycloalkenyl or substituted cycloalkenyl, cyano, alkyl or substituted alkyl, as well as those groups recited above as examples of alkyl substituents. Other examples of substituents include, but are not limited to, fused cyclic groups, such as fused cycloalkyl, fused cycloalkenyl, fused heterocycle, or fused aryl, where the aforementioned cycloalky, cylcoalkenyl, heterocycle and aryl substituents can themselves be optionally substituted. Still other examples of substituents on aryl groups (phenyl, as a non-limiting example) include, but are not limited to, haloalkyl and those groups recited as examples of alkyl substituents.

Examples of substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as examples of alkyl substituents. Other examples substituents on heterocyclic groups include, but are not limited to, spiro-attached or fused cylic substituents at any available point or points of attachment, for example spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In some embodiments, a heterocyclic group is substituted on carbon, nitrogen and/or sulfur at one or more positions. Examples of substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Examples of substituents on sulfur include, but are not limited to, oxo and $C_{1-6}$alkyl. In some embodiments, nitrogen and sulfur heteroatoms may independently be optionally oxidized and nitrogen heteroatoms may independently be optionally quaternized.

In some embodiments, substituents on ring groups, such as aryl, heteroaryl, cycloalkyl and heterocyclyl, include halogen, alkoxy and/or alkyl.

In some embodiments, substituents on alkyl groups include halogen and/or hydroxy.

A "halohydrocarbyl" as employed herein is a hydrocarbyl moiety, in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, dialkylamino (wherein each alkyl may be the same or different), arylamino, and cyclic amino groups. The term "ureido" as employed herein refers to a substituted or unsubstituted urea moiety.

The term "radical" as used herein means a chemical moiety comprising one or more unpaired electrons.

Where optional substituents are chosen from "one or more" groups it is to be understood that this definition includes all substituents being chosen from within one of the specified groups or from within the combination of all of the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

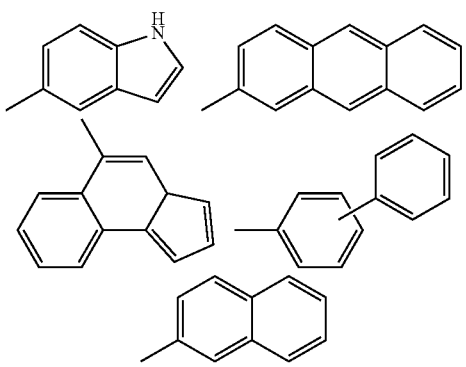

An "unsubstituted" moiety (e.g., unsubstituted cycloalkyl, unsubstituted heteroaryl, etc.) means a moiety as defined above that does not have any optional substituents.

A saturated, partially unsaturated or unsaturated three- to eight-membered carbocyclic ring is for example a four- to seven-membered, alternatively a five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

A saturated or unsaturated carboxylic and heterocyclic group may condense with another saturated or heterocyclic group to form a bicyclic group, for example a saturated or unsaturated nine- to twelve-membered bicyclic carbocyclic or heterocyclic group. Bicyclic groups include naphthyl, quinolyl, 1,2,3,4-tetrahydroquinolyl, 1,4-benzoxanyl, indanyl, indolyl, and 1,2,3,4-tetrahydronaphthyl.

When a carbocyclic or heterocyclic group is substituted by two $C_1$-$C_6$alkyl groups, the two alkyl groups may combine together to form an alkylene chain, for example a $C_1$-$C_3$alkylene chain. Carbocyclic or heterocyclic groups having this crosslinked structure include bicyclo[2.2.2]octanyl and norbornanyl.

The terms "kinase inhibitor" and "inhibitor of kinase activity", and the like, are used to identify a compound which is capable of interacting with a kinase and inhibiting its enzymatic activity.

The term "inhibiting kinase enzymatic activity" is used to mean reducing the ability of a kinase to transfer a phosphate group from a donor molecule, such as ATP, to a specific target molecule (substrate). For example, the inhibition of kinase activity may be at least about 10%. In some embodiments of the invention, such reduction of kinase activity is at least about 25%, alternatively at least about 50%, alternatively at least about 75%, and alternatively at least about 90%. In other embodiments, kinase activity is reduced by at least 95% and alternatively by at least 99%. The $IC_{50}$ value is the concentration of kinase inhibitor which reduces the activity of a kinase to 50% of the uninhibited enzyme.

The terms "inhibitor of VEGF receptor signaling" is used to identify a compound having a structure as defined herein, which is capable of interacting with a VEGF receptor and inhibiting the activity of the VEGF receptor. In some embodiments, such reduction of activity is at least about 50%, alternatively at least about 75%, and alternatively at least about 90%. In some embodiments, activity is reduced by at least 95% and alternatively by at least 99%.

The term "inhibiting effective amount" is meant to denote a dosage sufficient to cause inhibition of kinase activity. The amount of a compound of the invention which constitutes an "inhibiting effective amount" will vary depending on the compound, the kinase, and the like. The inhibiting effective amount can be determined routinely by one of ordinary skill in the art. The kinase may be in a cell, which in turn may be in a multicellular organism. The multicellular organism may be, for example, a plant, a fungus or an animal, for example a mammal and for example a human. The fungus may be infecting a plant or a mammal, for example a human, and could therefore be located in and/or on the plant or mammal.

In an exemplary embodiment, such inhibition is specific, i.e., the kinase inhibitor reduces the ability of a kinase to transfer a phosphate group from a donor molecule, such as ATP, to a specific target molecule (substrate) at a concentration that is lower than the concentration of the inhibitor that is required to produce another, unrelated biological effect. For example, the concentration of the inhibitor required for kinase inhibitory activity is at least 2-fold lower, alternatively at least 5-fold lower, alternatively at least 10-fold lower, and alternatively at least 20-fold lower than the concentration required to produce an unrelated biological effect.

Thus, the invention provides a method for inhibiting kinase enzymatic activity, comprising contacting the kinase with an inhibiting effective amount of a compound or composition according to the invention. In some embodiments, the kinase is in an organism. Thus, the invention provides a method for inhibiting kinase enzymatic activity in an organism, comprising administering to the organism an inhibiting effective amount of a compound or composition according to the invention. In some embodiments, the organism is a mammal, for example a domesticated mammal. In some embodiments, the organism is a human.

The term "therapeutically effective amount" as employed herein is an amount of a compound of the invention, that when administered to a patient, elicits the desired therapeutic effect. The therapeutic effect is dependent upon the disease being treated and the results desired. As such, the therapeutic effect can be treatment of a disease-state. Further, the therapeutic effect can be inhibition of kinase activity. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art.

In some embodiments, the therapeutic effect is inhibition of angiogenesis. The phrase "inhibition of angiogenesis" is used to denote an ability of a compound according to the present invention to retard the growth of blood vessels, such as blood vessels contacted with the inhibitor as compared to blood vessels not contacted. In some embodiments, angiogenesis is tumor angiogenesis. The phrase "tumor angiogenesis" is intended to mean the proliferation of blood vessels that penetrate into or otherwise contact a cancerous growth, such as a tumor. In some embodiments, angiogenesis is abnormal blood vessel formation in the eye.

In an exemplary embodiment, angiogenesis is retarded by at least 25% as compared to angiogenesis of non-contacted blood vessels, alternatively at least 50%, alternatively at least 75%, alternatively at least 90%, alternatively at least 95%, and alternatively, at least 99%. Alternatively, angiogenesis is inhibited by 100% (i.e., the blood vessels do not increase in size or number). In some embodiments, the phrase "inhibition of angiogenesis" includes regression in the number or size of blood vessels, as compared to non-contacted blood vessels. Thus, a compound according to the invention that inhibits angiogenesis may induce blood vessel growth retardation, blood vessel growth arrest, or induce regression of blood vessel growth.

Thus, the invention provides a method for inhibiting angiogenesis in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is treatment of an ophthalmic disesase, disorder or condition. The phrase "treatment of an ophthalmic disease, disorder or condition" is intended to mean the ability of a compound according to the present invention to treat an exudative and/or inflammatory ophthalmic disease, disorder or condition, a disorder related to impaired retinal vessel permeability and/or integrity, a disorder related to retinal microvessel rupture leading to focal hemorrhage, a disease of the back of the eye, a retinal disease, or a disease of the front of the eye, or other ophthalmic disease, disorder or condition.

In some embodiments, the ophthalmic disease, disorder or condition includes but is not limited to Age Related Macular Degeneration (ARMD), exudative macular degeneration (also known as "wet" or neovascular age-related macular degeneration (wet-AMD), macular oedema, aged disciform macular degeneration, cystoid macular oedema, palpebral oedema, retinal oedema, diabetic retinopathy, Acute Macular Neuroretinopathy, Central Serous Chorioretinopathy, chorioretinopathy, Choroidal Neovascularization, neovascular maculopathy, neovascular glaucoma, obstructive arterial and venous retinopathies (e.g. Retinal Venous Occlusion or Retinal Arterial Occlusion), Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease(CAD), Frosted Branch Angitis, Sickle Cell Retinopathy and other Hemoglobinopathies, Angioid Streaks, macular oedema occurring as a result of aetiologies such as disease (e.g. Diabetic Macular Oedema), eye injury or eye surgery, retinal ischemia or degeneration produced for example by injury, trauma or tumours, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, an ocular inflammatory disease caused by bacterial or viral infection or by an ophthalmic operation, an ocular inflammatory disease caused by a physical injury to the eye, and a symptom caused by an ocular inflammatory disease including itching, flare, oedema and ulcer, erythema, erythema exsudativum multiforme, erythema nodosum, erythema annulare, scleroedema, dermatitis, angioneurotic oedema, laryngeal oedema, glottic oedema, subglottic laryngitis, bronchitis, rhinitis, pharyngitis, sinusitis, laryngitis or otitis media.

In some embodiments, the ophthalmic disease, disorder or condition includes but is not limited to age-related macular degeneration, diabetic retinopathy, retinal edema, retinal vein occlusion, neovascular glaucoma, retinopathy of prematurity, pigmentary retinal degeneration, uveitis, corneal neovascularization or proliferative vitreoretinopathy.

In some embodiments, the ophthalmic disease, disorder or condition is age-related macular degeneration, diabetic retinopathy or retinal edema.

Thus, the invention provides a method for treating an ophthalmic disease, disorder or condition in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is inhibition of retinal neovascularization. The phrase "inhibition of retinal neovascularization" is intended to mean the ability of a compound according to the present invention to retard the growth of blood vessels in the eye, for example new blood vessels originating from retinal veins, for example, to retard the growth of new blood vessels originating from retinal veins and extending along the inner (vitreal) surface of the retina.

In an exemplary embodiment, retinal neovascularization is retarded by at least 25% as compared to retinal neovascularization of non-contacted blood vessels, alternatively at least 50%, alternatively at least 75%, alternatively at least 90%, alternatively at least 95%, and alternatively, at least 99%. Alternatively, retinal neovascularization is inhibited by 100% (i.e., the blood vessels do not increase in size or number). In some embodiments, the phrase "inhibition of retinal neovascularization" includes regression in the number or size of blood vessels, as compared to non-contacted blood vessels. Thus, a compound according to the invention that inhibits retinal neovascularization may induce blood vessel growth retardation, blood vessel growth arrest, or induce regression of blood vessel growth.

Thus, the invention provides a method for inhibiting retinal neovascularization in an animal, comprising administering to an animal in need of such treatment a therapeutically effective amount of a compound or composition of the invention. In some embodiments, the animal is a mammal, for example a domesticated mammal. In some embodiments, the animal is a human.

In some embodiments, the therapeutic effect is inhibition of cell proliferation. The phrase "inhibition of cell proliferation" is used to denote an ability of a compound according to the present invention to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers or comparing the size of the growth of contacted cells with non-contacted cells.

In an exemplary embodiment, growth of cells contacted with the inhibitor is retarded by at least 25% as compared to growth of non-contacted cells, alternatively at least 50%, alternatively at least 75%, alternatively at least 90%, alternatively at least 95%, and alternatively, at least 99%. Alternatively, cell proliferation is inhibited by 100% (i.e., the contacted cells do not increase in number). In some embodiments, the phrase "inhibition cell proliferation" includes a reduction in the number or size of contacted cells, as compared to non-contacted cells. Thus, a compound according to the invention that inhibits cell proliferation in a contacted cell may induce the contacted cell to undergo growth retardation, to undergo growth arrest, to undergo programmed cell death (i.e., to apoptose), or to undergo necrotic cell death.

In some embodiments, the contacted cell is a neoplastic cell. The term "neoplastic cell" is used to denote a cell that shows aberrant cell growth. In some embodiments, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth.

In some embodiments, the contacted cell is in an animal. Thus, the invention provides a method for treating a cell proliferative disease or condition in an animal, comprising administering to an animal in need of such treatment a therapeutically effective amount of a compound or composition of the invention. In some embodiments, the animal is a mammal, for example a domesticated mammal. In some embodiments, the animal is a human.

The term "cell proliferative disease or condition" is meant to refer to any condition characterized by aberrant cell growth, such as abnormally increased cellular proliferation. Examples of such cell proliferative diseases or conditions amenable to inhibition and treatment include, but are not limited to, cancer. Examples of particular types of cancer include, but are not limited to, breat cancer, lung cancer, colon cancer, rectal cancer, bladder cancer, prostate cancer leukemia and renal cancer. In some embodiments, the invention provides a method for inhibiting neoplastic cell proliferation in an animal comprising administering to an animal having at least one neoplastic cell present in its body a therapeutically effective amount of a compound of the invention or a composition thereof.

The term "patient" as employed herein for the purposes of the present invention includes humans and other animals, for example mammals, and other organisms. Thus the compounds, compositions and methods of the present invention are applicable to both human therapy and veterinary applications. In some embodiments the patient is a mammal, for example a human.

The terms "treating", "treatment", or the like, as used herein covers the treatment of a disease-state in an organism, and includes at least one of: (i) preventing the disease-state from occurring, in particular, when such animal is predisposed to the disease-state but has not yet been diagnosed as having it; (ii) inhibiting the disease-state, i.e., partially or completely arresting its development; (iii) relieving the disease-state, i.e., causing regression of symptoms of the disease-state, or ameliorating a symptom of the disease; and (iv) reversal or regression of the disease-state, such as eliminating or curing of the disease. In some embodiments of the present invention the organism is an animal, for example a mammal, for example a primate, for example a human. As is known in the art, adjustments for systemic versus localized delivery, age, body weight, general health, sex, diet, time of administration, drug interaction, the severity of the condition, etc., may be necessary, and will be ascertainable with routine experimentation by one of ordinary skill in the art. In some embodiments, the terms "treating", "treatment", or the like, as used herein covers the treatment of a disease-state in an organism and includes at least one of (ii), (iii) and (iv) above.

Administration for non-opthalmic diseases, disorders or conditions may be by any route, including, without limitation, parenteral, oral, sublingual, transdermal, topical, intranasal, intratracheal, or intrarectal. In some embodiments, compounds of the invention are administered intravenously in a hospital setting. In some embodiments, administration may be by the oral route.

Examples of routes of administration for ophthalmic diseases, disorders and conditions include but are not limited to, systemic, periocular, retrobulbar, intracanalicular, intravitral injection, topical (for example, eye drops), subconjunctival injection, subtenon, transcleral, intracameral, subretinal, electroporation, and sustained-release implant. Other routes of administration other injection sites or other forms of administration for ophthalmic situations will be known or contemplated by one skilled in the art and are intended to be within the scope of the present invention.

In some embodiments of the present invention, routes of administration for ophthalmic diseases, disorders and conditions include topical, subconjunctval injection, intravitreal injection, or other ocular routes, systemically, or other methods known to one skilled in the art to a patient following ocular surgery.

In some other embodiments of the present invention, routes of administration for ophthalmic diseases, disorders and conditions include topical, intravitreal, transcleral, periocular, conjunctival, subtenon, intracameral, subretinal, subconjunctival, retrobulbar, or intracanalicular.

In some embodiments of the present invention, routes of administration for ophthalmic diseases, disorders and conditions include topical administration (for example, eye drops), systemic administration (for example, oral or intravenous), subconjunctival injection, periocular injection, intravitreal injection, and surgical implant.

In some embodiments of the present invention, routes of administration for ophthalmic diseases, disorders and conditions include intravitreal injection, periocular injection, and sustained-release implant.

In some embodiments of the present invention, an intraocular injection may be into the vitreous (intravitreal), under the conjunctiva (subconjunctival), behind the eye (retrobulbar), into the sclera, under the Capsule of Tenon (sub-Tenon), or may be in a depot form.

The compounds of the present invention form salts which are also within the scope of this invention. Reference to a compound of the invention, for example a compound of Formula (I), herein is understood to include reference to salts thereof, unless otherwise indicated.

The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic (exhibiting minimal or no undesired toxicological effects), physiologically acceptable) salts are preferred, although other salts are also useful, e.g., in isolation or purification steps which may be employed during preparation. Salts of the compounds of the invention may be formed, for example, by reacting a compound of the present invention with an amount of acid or base, such as an equivalent amount, in a medium such as one in which the salts precipitates or in an aqueous medium followed by lyophilization.

The compounds of the present invention which contain a basic moiety, such as but not limited to an amine or a pyridine or imidazole ring, may form salts with a variety of organic and inorganic acids. Examples of acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemi sulfates, heptanoates, hexanoates, hydrochlorides, hydrobromides, hydroiodides, hydroxyethanesulfanotes (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such as but not limited to a carboxylic acid, may form salts with a variety of organic and inorganic bases. Examples of basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl and butyl chlorides, bromides and iodides), dialkyl sulfates (e.g. dimethyl, diethyl, dibuty and diamyl sulfates), long chain halides (e.g. decyl, lauryl, myristyl and stearyl chlorides, bromides and iodides), aralkyl halides (e.g. benzyl and phenethyl bromides), and others.

As used herein, the term "pharmaceutically acceptable salts" is intended to mean salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. Other salts include pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Another aspect of the invention provides compositions comprising a compound according to the present invention. For example, in some embodiments of the invention, a composition comprises a compound, N-oxide, hydrate, solvate, pharmaceutically acceptable salt, complex or prodrug of a compound according to the present invention present in at least about 30% enantiomeric or diastereomeric excess. In some embodiments of the invention, the compound, N-oxide, hydrates, solvate, pharmaceutically acceptable salt, complex or prodrug is present in at least about 50%, at least about 80%, or even at least about 90% enantiomeric or diastereomeric excess. In some embodiments of the invention, the compound, N-oxide, hydrate, solvate, pharmaceutically acceptable salt, complex or prodrug is present in at least about 95%, alternatively at least about 98% and alternatively at least about 99% enantiomeric or diastereomeric excess. In other embodiments of the invention, a compound, N-oxide, hydrate, solvate, pharmaceutically acceptable salt, complex or prodrug is present as a substantially racemic mixture.

Some compounds of the invention may have chiral centers and/or geometric isomeric centers (E- and Z-isomers), and it is to be understood that the invention encompasses all such optical, enantiomeric, diastereoisomeric and geometric isomers. The invention also comprises all tautomeric forms of the compounds disclosed herein. Where compounds of the invention include chiral centers, the invention encompasses the enantiomerically and/or diasteromerically pure isomers of such compounds, the enantiomerically and/or diastereomerically enriched mixtures of such compounds, and the racemic and scalemic mixtures of such compounds. For example, a composition may include a mixture of enantiomers or diastereomers of a compound of Formula (I) in at least about 30% diastereomeric or enantiomeric excess. In some embodiments of the invention, the compound is present in at least about 50% enantiomeric or diastereomeric excess, in at least about 80% enantiomeric or diastereomeric excess, or even in at least about 90% enantiomeric or diastereomeric excess. In some embodiments of the invention, the compound is present in at least about 95%, alternatively in at least about 98% enantiomeric or diastereomeric excess, and alternatively in at least about 99% enantiomeric or diastereomeric excess.

The chiral centers of the present invention may have the S or R configuration. The racemic forms can be resolved by physical methods, such as, for example, fractional crystallization, separation or crystallization of diastereomeric derivates or separation by chiral column chromatography. The individual optical isomers can be obtained either starting from chiral precursors/intermediates or from the racemates by any suitable method, including without limitation, conventional methods, such as, for example, salt formation with an optically active acid followed by crystallization.

The present invention also includes prodrugs of compounds of the invention. The term "prodrug" is intended to represent a compound covalently bonded to a carrier, which prodrug is capable of releasing the active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the present invention), amides (e.g., trifluoroacetylamino, acetylamino, and the like), and the like.

The compounds of the invention may be administered, for example, as is or as a prodrug, for example in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_1$-$C_6$alkoxymethyl esters (e.g., methoxymethyl), $C_1$-$C_6$alkanoyloxymethyl esters (e.g., for example pivaloyloxymethyl), phthalidyl esters, $C_3$-$C_8$cycloalkoxycarbonyloxy-$C_1$-$C_6$alkyl esters (e.g., 1-cyclohexylcarbonyloxyethyl); 1,3-dioxolen-2-onylmethyl esters (e.g., 5-methyl-1,3-dioxolen-2-onylmethyl; and $C_1$-$C_6$alkoxycarbonyloxyethyl esters (e.g., 1-methoxycarbonyloxyethyl) and may be formed at any appropriate carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_1$-$C_6$alkyl or N,N-di-$C_1$-$C_6$alkyl amide such as N-methyl, N-ethyl, N-propyl, N,N-dimethyl, N-ethyl-N-methyl or N,N-diethyl amide.

Upon administration to a subject, the prodrug undergoes chemical conversion by metabolic or chemical processes to yield a compound of the present invention, for example, a salt and/or solvate thereof. Solvates of the compounds of the present invention include, for example, hydrates.

Throughout the specification, embodiments of one or more chemical substituents are identified. Also encompassed are combinations of various embodiments. For example, the invention describes some embodiments of D in the compounds and describes some embodiments of group G. Thus, as an example, also contemplated as within the scope of the invention are compounds in which examples of D are as described and in which examples of group G are as described.

Compounds

According to one embodiment, the invention provides compounds of Formula (I):

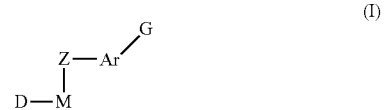

(I)

including N-oxides, hydrates, solvates, pharmaceutically acceptable salts, prodrugs and complexes thereof, and racemic and scalemic mixtures, diastereomers and enantiomers thereof, wherein, D is selected from the group consisting of an aromatic, heteroaromatic, cycloalkyl or heterocyclic ring system, each of which is optionally substituted with 1 to 5 independently selected $R^{38}$;

M is an optionally substituted fused heterocyclic moiety;

Z is —O—;

Ar is a 5 to 7 membered aromatic ring system, which is optionally substituted with 0 to 4 $R^2$ groups; and G is a group B-L-T, wherein B is —N($R^{13}$)— or —C(=S)—;

L is selected from the group consisting of —C(=O)N($R^{13}$)—, —C(=O)$C_0$-$C_1$alkyl-C(=O)N($R^{13}$)—, and —C(=O)—, wherein an alkyl group of the aforementioned L group is optionally substituted; and T is selected from the group consisting of —$C_0$-$C_5$alkyl, —$C_0$-$C_5$alkyl-Q, —O—$C_0$-$C_5$alkyl-Q, —O—$C_0$-$C_5$alkyl, —C(=S)≥N($R^{13}$)—$C_0$-$C_5$alkyl-Q, —$C_0$-$C_5$alkyl-S(O)$_2$-Q, and —C(=S)—N($R^{13}$)—$C_0$-$C_5$alkyl, wherein each $C_0$-$C_5$alkyl is optionally substituted;

wherein each $R^{38}$ is independently selected from the group consisting of halo, optionally substituted $C_1$-$C_6$ alkyl, —$C_0$-$C_6$alkyl-(optionally substituted heterocycle), optionally substituted —$C_2$-$C_6$alkenyl=N-heterocycle-$C_1$-$C_6$alkyl, optionally substituted —CH=N-heterocycle, —(CH$_2$)$_j$NR$^{39}$(CH$_2$)$_n$R$^{36}$, —C(O)(CH$_2$)$_j$NR$^{39}$(CH$_2$)$_n$R$^{36}$, —(CH$_2$)$_j$NR$^{39}$(CH$_2$)$_i$[O(CH$_2$)$_i$]$_x$(CH$_2$)$_j$R$^{99}$, —(CH$_2$)$_j$NR$^{39}$C(O)(CH$_2$)$_j$O(CH$_2$)$_j$OR$^3$, —(CH$_2$)$_j$NR$^{39}$(CH$_2$)$_j$(CH)(NH$_2$)(COOH) and —(CH$_2$)$_j$NR$^{39}$(CH$_2$)$_j$COOH;

wherein each j is an integer independently ranging from 0 to 4, alternatively 1-2, n is an integer ranging from 0 to 6, x is an integer ranging from 0-6, alternatively 2-3, each i is independently 2 or 3, and the —(CH$_2$)$_n$— moieties of the foregoing $R^{38}$ groups are optionally substituted with $C_1$-$C_6$ alkyl;

$R^{36}$ is H or —(CH$_2$)$_{n3}$OR$^{37}$;

wherein n3 is an integer ranging from 0 to 6;

with the proviso that when $R^{36}$ and $R^{39}$ are both attached to the same nitrogen, then $R^{36}$ and $R^{39}$ are not both bonded to the nitrogen directly through an oxygen;

each $R^{37}$ is independently selected from H, $C_1$-$C_6$ alkyl, —(CH$_2$)$_n$O(CH$_2$)$_a$O—$C_1$-$C_6$alkyl, —(CH$_2$)$_n$CH(NH)(CH$_2$)—O—$C_1$-$C_6$alkyl, —(CH$_2$)$_n$CH(NH)(CH$_2$)$_n$$C_1$-$C_6$alkyl, —(CH$_2$)$_n$O(CH$_2$)$_a$O—$C_3$-$C_{10}$cycloalkyl, —(CH$_2$)$_n$CH(NH)(CH$_2$)$_n$O—$C_3$-$C_{10}$cycloalkyl and —(CH$_2$)$_n$CH(NH)(CH$_2$)$_n$$C_3$-$C_{10}$cycloalkyl, wherein each n is an integer independently ranging from 0 to 6 and a is an integer ranging from 2 to 6, wherein the alkyl and cycloalkyl moieties of the foregoing $R^{37}$ groups are optionally substituted by one or more independently selected substituents;

$R^{39}$ is selected from the group consisting of H, $C_1$-$C_6$ alkyl, —SO$_2$—$C_1$-$C_6$alkyl, —C(O)—$C_1$-$C_6$ alkyl, —C(O)O—$C_1$-$C_6$alkyl, —C(O)—$C_1$-$C_6$alkyl-NR$^3$R$^3$, —$C_1$-$C_6$alkyl-O—$C_1$-$C_6$alkyl, —C(O)(CH$_2$)$_{0-4}$O(CH$_2$)$_{1-4}$OC$_1$-$C_6$alkyl, —C(O)—$C_1$-$C_6$alkyl-OH and —C(O)CH[CH($C_1$-$C_6$alkyl)$_2$]NR$^3$R$^3$ and a protecting group used to protect secondary amino groups with the proviso that when $R^{36}$ and $R^{39}$ are both attached to the same nitrogen, then $R^{36}$ and $R^{39}$ are not both bonded to the nitrogen directly through an oxygen;

$R^{99}$ at each occurrence is independently —H, —NH$_2$ or —OR$^3$;

$R^2$ at each occurrence is independently selected from —H and halogen;

each $R^3$ is independently selected from the group consisting of —H and $R^4$;

$R^4$ is ($C_1$-$C_6$)alkyl;

each $R^{13}$ is independently selected from the group consisting of —H, —C(O)NR$^3$R$^3$ and $C_1$-$C_6$ alkyl;

Q is a three- to ten-membered ring system, optionally substituted with between zero and four of $R^{20}$; and each $R^{20}$ is independently selected from the group consisting of —H, halogen, trihalomethyl, —OR$^3$, —S(O)$_{0-2}$R$^3$, —S(O)$_2$NR$^3$R$^3$, —C(O)OR$^3$, —C(O)NR$^3$R$^3$, —(CH$_2$)$_{0-5}$(heteroaryl), $C_1$-$C_6$ alkyl, —(CH$_2$)$_n$P(=O)($C_1$-$C_6$alkyl)$_2$, wherein n is an integer ranging from 0 to 6, and the heteroaryl and $C_1$-$C_6$ alkyl are optionally substituted.

In some embodiments of the compounds according to the present invention D is an aromatic or heteroaromatic ring system, each of which is substituted with 1 or 2 independently selected $R^{38}$ groups.

In some embodiments according to the present invention, D is a 5- or 6-membered heteroaromatic ring system, each of which is substituted with 1 or 2 independently selected $R^{38}$ groups.

In some embodiments according to the present invention, D is a 6-membered aromatic or 6-membered heteroaromatic ring system, each of which is substituted with 1 or 2 independently selected $R^{38}$ groups.

In some embodiments according to the present invention, D is a 6-membered aromatic ring system, substituted with 1 or 2 independently selected $R^{38}$ groups.

In some embodiments according to the present invention, D is a 6-membered heteroaromatic ring system, substituted with 1 or 2 independently selected $R^{38}$ groups.

In some embodiments according to the present invention, D is a 5-membered heteroaromatic ring system, substituted with 1 or 2 independently selected $R^{38}$ groups.

In some embodiments of the present invention, D is selected from the group consisting of

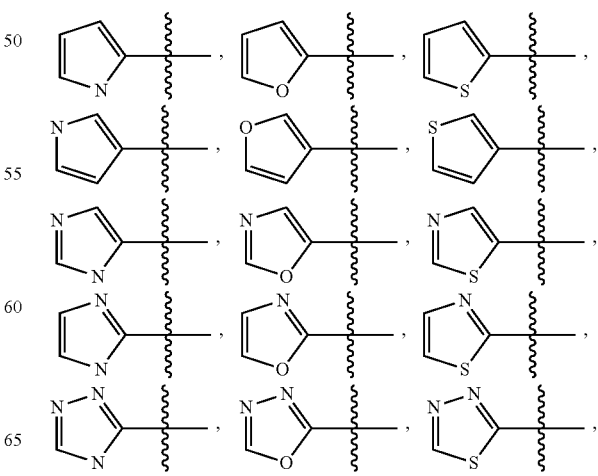

-continued

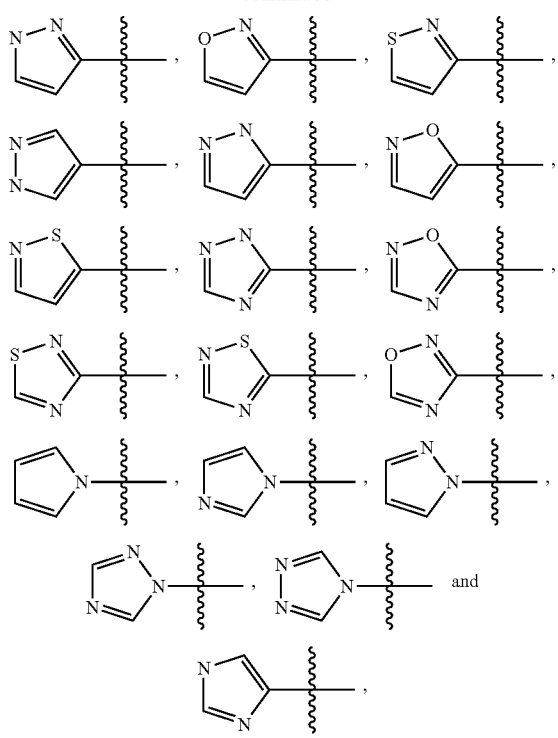

wherein the members of said group are substituted with 1 or 2 independently selected $R^{38}$ groups.

In some embodiments of the present invention, D is selected from the group consisting of

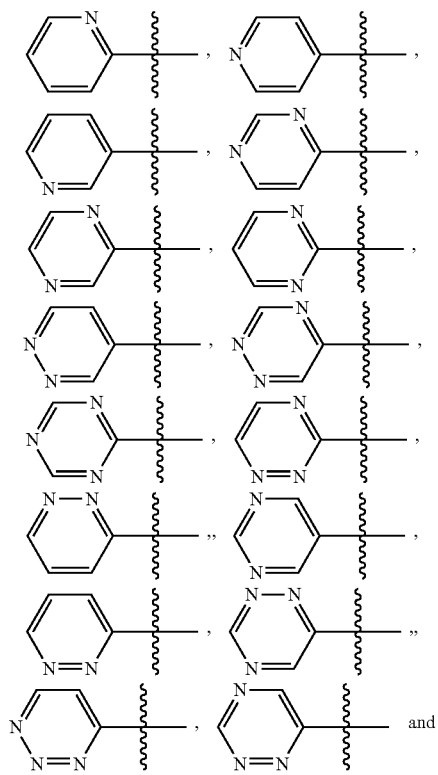

-continued

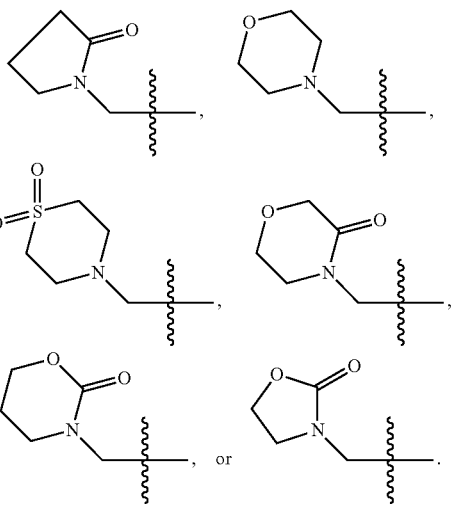

wherein the members of said group are substituted with 1 or 2 independently selected $R^{38}$ groups.

In some embodiments according to the present invention, D is substituted with one $R^{38}$ group.

In some embodiments of the present invention, D is phenyl, pyridyl, imidazolyl or tetrahydropyridyl, each of which is substituted with 1 or 2 independently selected $R^{38}$ groups.

In some embodiments according to the present invention, $R^{38}$ is

In some embodiments according to the present invention, D is phenyl, substituted with 1 $R^{38}$ groups.

In some embodiments according to the present invention, D is pyridyl, substituted with 1 or 2 independently selected $R^{38}$ groups.

In some embodiments according to the present invention, D is pyridyl, substituted with one $R^{38}$.

In some embodiments according to the present invention, D is imidazolyl, substituted with one or two $R^{38}$.

In some embodiments according to the present invention, D is imidazolyl, substituted with two $R^{38}$.

In some embodiments of the present invention, D is tetrahydropyridyl substituted with 1 $R^{38}$ group.

In some embodiments of the present invention, each $R^{38}$ is independently selected from the group consisting of $C_1$-$C_6$ alkyl, —$(CH_2)_j NR^{39}(CH_2)_i[(CH_2)_i]_x(CH_2)_j R^{99}$, —$(CH_2)_j NR^{39}(CH_2)_n R^{36}$ and —$C_0$-$C_6$alkyl-(optionally substituted heterocycle).

In some embodiments of the present invention each $R^{38}$ is independently selected from the group consisting of $C_1$-$C_6$ alkyl, —$(CH_2)_j NR^{39}(CH_2)_i[O(CH_2)_i]_x(CH_2)_j R^{99}$, and —$(CH_2)_j NR^{39}(CH_2)_n R^{36}$.

In some embodiments of the present invention, each $R^{38}$ is independently —$(CH_2)_j NR^{39}(CH_2)_i[O(CH_2)_i]_x(CH_2)_j R^{99}$ or —$(CH_2)_j NR^{39}(CH_2)_n R^{36}$.

In some embodiments of the present invention, $R^{38}$ is —$(CH_2)_j NR^{39}(CH_2)_n R^{36}$, wherein j is 1 and n is 2.

In some embodiments of the present invention $R^{38}$ is —$(CH_2)NR^{39}(CH_2)_2 OCH_3$.

In some embodiments of the present invention, $R^{38}$ is —$(CH_2)_jNR^{39}(CH_2)_i[O(CH_i)]_x(CH_2)_jR^{99}$.

In some embodiments of the present invention, $R^{38}$ is —$(CH_2)_jNR^{39}(CH_2)_i[O(CH_2)_i]_x(CH_2)_jR^{99}$, wherein j is 1, i is 2, and x is 3 or 3.

In some embodiments of the present invention, D is pyridyl subsituted with one —$(CH_2)_jNR^{39}(CH_2)_nR^{36}$, alternatively one —$(CH_2)_jNR^{39}(CH_2)_nR^{36}$, wherein j is 1 and n is 2.

In some embodiments of the present invention, D is pyridyl substituted with one —$(CH_2)_jNR^{39}(CH_2)_i[O(CH_2)_i]_x(CH_2)_jR^{99}$, alternatively one —$(CH_2)_jNR^{39}(CH_2)_i[O(CH_2)_i]_x(CH_2)_j$OMe, wherein j is 1, i is 2, and x is 2 or 3.

In some embodiments of the present invention, D is pyridyl substituted with one —$(CH_2)_jNR^{39}(CH_2)_j(CH)(NH_2)(COOH)$.

In some embodiments of the present invention, D is pyridyl subsituted by one —$C_0$-$C_6$alkyl-(optionally substituted heterocycle), for example —$C_0$-$C_6$alkyl-(heterocycle substituted with one oxo).

In some embodiments of the present invention, D is pyridyl subsittuted with one —$(CH_2)_jNR^{39}(CH_2)_j$COOH.

In some embodiments of the present invention, D is pyridyl subsituted with one —$(CH_2)_jNR^{39}C(O)(CH_2)_jO(CH_2)_jOR^3$.

In some embodiments of the present invention D is tetrahydropyridyl substituted with one optionally substituted —CH=N-heterocycle.

In some embodiments of the present invention D is tetrahydropyridyl substituted with one —$C(O)(CH_2)_jNR^{39}(CH_2)_nR^{36}$.

In some embodiments of the present invention D is imidazolyl subsituted with one $C_1$-$C_6$alkyl and one —$(CH_2)_jNR^{39}(CH_2)_nR^{36}$.

In some embodiments of the present invention, D is phenyl substituted with one —$(CH)_jNR^{39}(CH_2)_i[O(CH_2)_i]_x(CH_2)_jR^{99}$.

In some embodiments of the present invention, $R^{39}$ is selected from the group consisting of H, —C(O)—$C_1$-$C_6$alkyl (for example, —C(O)-Me), —C(O)—$C_1$-$C_6$alkyl-$NH_2$, —$SO_2$-Me, —$C(O)(CH_2)_{0-4}O(CH_2)_{1-4}OC_1$-$C_6$alkyl and —C(O)CH[CH($C_1$-$C_6$alkyl)$_2$]$NR^3R^3$.

In another embodiment of the present invention, $R^{39}$ is selected from the group consisting of H, —C(O)-Me, —C(O)$(CH_2)O(CH_2)_2OC_1$alkyl and —C(O)CH(CHMe$_2$)NH$_2$.

In some embodiments of the present invention, $R^{39}$ is H or —C(O)-Me.

In some embodiments of the present invention, $R^{39}$ is H.

In some embodiments of the present invention $R^{36}$ is —OMe.

In some embodiments of the present invention, $R^{99}$ is —OMe.

In some embodiments of the present invention, M is

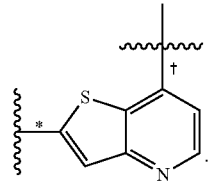

wherein
* represents the point of attachment to D; and
† represents the point of attachment to Z.

In some embodiments of the present invention, Ar is selected from the group consisting of phenyl, pyrazine, pyridazine, pryimidine and pyridine, wherein each of said phenyl, pyrazine, pyridazine, pryimidine and pyridine is optionally substituted with 0 to 4 $R^2$ groups.

In some embodiments of the present invention, Ar is phenyl, optionally substituted with 0 to 4 $R^2$ groups, alternatively with 1 or 2 $R^2$ groups, alternatively with 0, 1 or 2 halo.

In some embodiments of the present invention, Ar is phenyl substituted with one halo, for example one F.

In some embodiments of the present invention, G is selected from the group consisting of

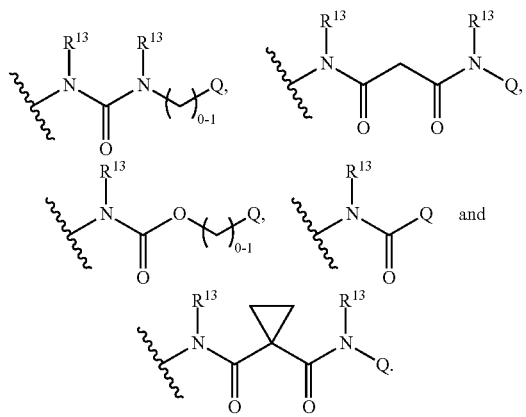

In some embodiments of the present invention, G is selected from the group consisting of

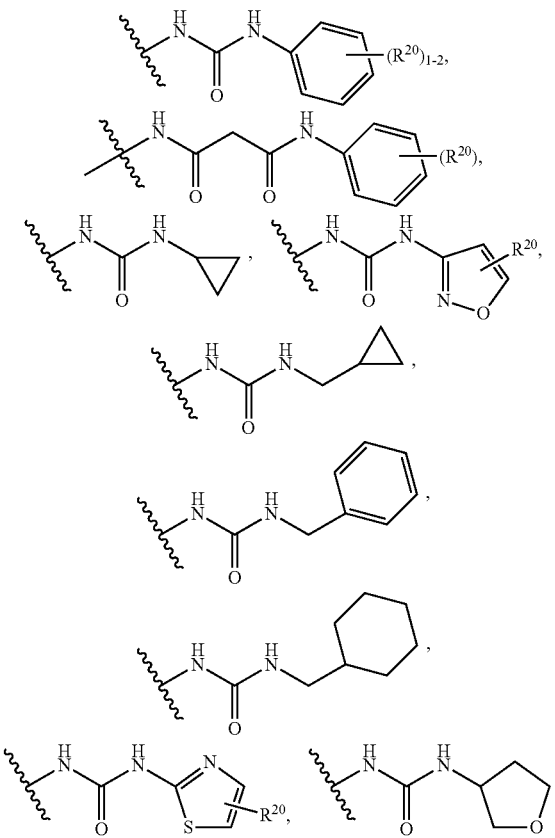

27

-continued

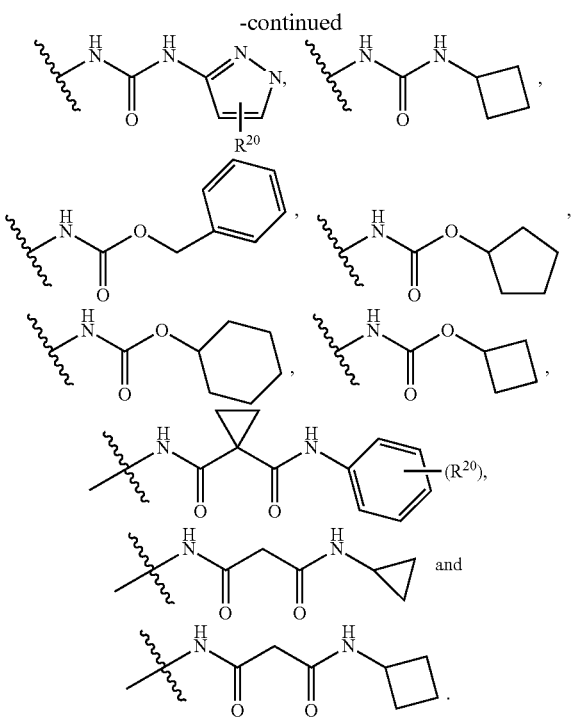

In some embodiments of the present invention, G is selected from the group consisting of

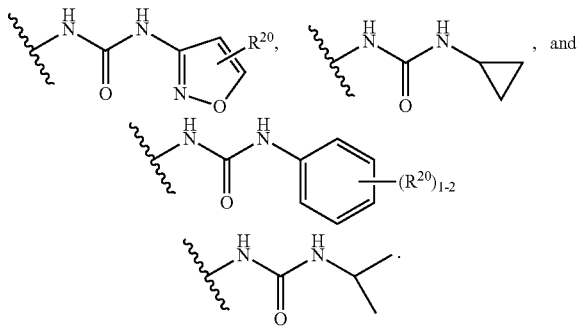

In some embodiments of the present invention, Q is selected from the group consisting of phenyl, cyclopropyl, isoxazolyl, cyclohexyl, thiazolyl, tetrahydrofuran, pyrazolyl, cyclobutyl and cyclopentyl, optionally substituted with between zero and two $R^{20}$.

In some embodiments of the present invention, Q is phenyl, optionally substituted with one or two $R^{20}$.

In some embodiments of the presention invention, Q is cyclopropyl.

In some embodiments of the presention invention Q is tetrahydrofuran.

In some embodiments of the present invention, Q is pyrazolyl optionally substituted with one $R^{20}$.

In some embodiments of the present invention, each $R^{20}$ is independently selected from the group consisting of —P(=O)(Me)$_2$, methyl, halo (for example F), trihalomethyl, methoxy, —C(O)NH$_2$, heteroaryl, —COON, —SO$_2$HN$_2$, —C(O)NH$_2$, —COOMe, —C(O)N(H)(Me), —C(O)N(Me)$_2$ and —SO$_2$Me.

In some embodiments of the present invention, Q is substituted with one $R^{20}$ selected from —P(=O)(Me)$_2$, methyl and methoxy.

28

In some embodiments of the present invention, Q is phenyl substituted with one —P(=O)(Me)$_2$.

In some embodiments of the present invention, Q is pyrazolyl, isoxazolyl or thiazolyl substituted with one methyl.

In some embodiments of the present invention,

D is phenyl, pyridyl, imidazolyl or tetrahydropyridyl, each of which is substituted with 1 or 2 independently selected $R^{38}$ groups;

M is

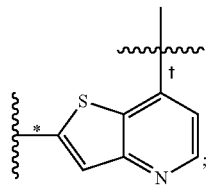 [SMILES: *c1cc2nccc(*)c2s1]

Z is —O—;

Ar is phenyl optionally substituted with 0 to 4 $R^2$ groups, for example with between zero and four halo; and G is selected from the group consisting of

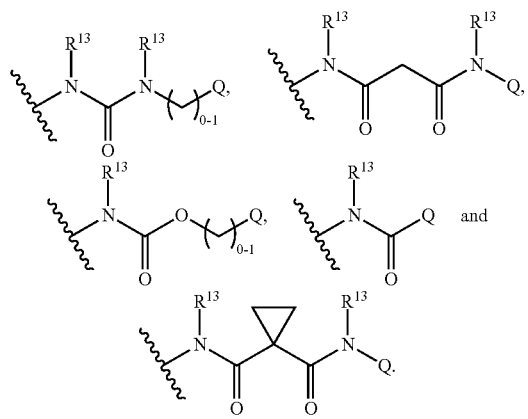

wherein Q is optionally substituted with from 0 to 4 independently selected $R^{20}$.

In some embodiments of the present invention,

D is pyridyl substituted with —(CH$_2$)$_j$NR$^{39}$(CH$_2$)$_n$R$^{36}$, —(CH$_2$)$_j$NR$^{39}$(CH$_2$)$_i$[O(CH$_2$)$_i$]$_x$(CH$_2$)$_j$R$^{99}$, —C$_0$-C$_6$alkyl-(heterocycle optionally substituted with one or two oxo), —(CH$_2$)$_j$NR$^{39}$(CH$_2$)$_j$COOH or —(CH$_2$)$_j$NR$^{39}$(CH$_2$)$_j$(CH)(NH$_2$)(COOH);

M is

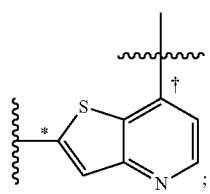 [SMILES: *c1cc2nccc(*)c2s1]

Z is —O—;

Ar is phenyl optionally substituted with 0 to 4 $R^2$ groups, for example one F; and G is

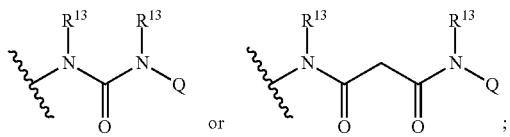

wherein Q is optionally substituted with from 0 to 4 independently selected $R^{20}$.

In some embodiments of the present invention,

D is pyridyl substituted with —$(CH_2)_jNR^{39}(CH_2)_nR^{36}$, —$(CH_2)_jNR^{39}(CH_2)_i[O(CH_2)_i]_x(CH_2)_jR^{99}$, —$C_0$-$C_6$alkyl-(heterocycle substituted with one oxo), —$(CH_2)_jNR^{39}(CH_2)_jCOOH$ or —$(CH_2)_jNR^{39}(CH_2)_j(CH)(NH_2)(COOH)$;

$R^{99}$ is OMe;

M is

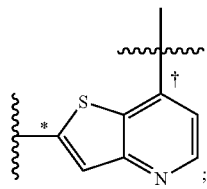 [SMILES: *c1cc2nccc(*)c2s1]

Z is —O—;

Ar is phenyl optionally substituted with 0 to 4 $R^2$ groups, for example phenyl substituted with one F; and G is

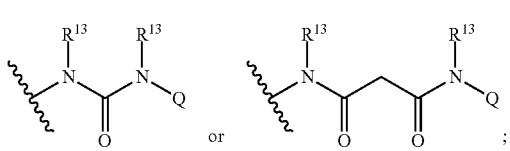

wherein $R^{13}$ is H; and

Q is phenyl optionally substituted with 1 or 2 independently selected $R^{20}$, wherein each $R^{20}$ is independently selected from the group consisting of —P(=O)(Me)$_2$, methyl, halo (for example F), trihalomethyl, methoxy, —C(O)NH$_2$, heteroaryl, —COON, —SO$_2$HN$_2$, —C(O)NH$_2$, —COOMe, —C(O)N(H)(Me), —C(O)N(Me)$_2$ and —SO$_2$Me, or Q is pyrazolyl optionally substituted with methyl, or Q is cyclopropyl, cyclobutyl or tetrahydrofuran.

In some embodiments of the present invention,

D is pyridyl substituted with —$(CH_2)_jNR^{39}(CH_2)_nR^{36}$, —$(CH_2)_jNR^{39}(CH_2)_i[O(CH_2)_i]_x(CH_2)_jR^{99}$, —$C_0$-$C_6$alkyl-(heterocycle substituted with one oxo), —$(CH_2)_jNR^{39}(CH_2)_jCOOH$ or —$(CH_2)_jNR^{39}(CH_2)_j(CH)(NH_2)(COOH)$;

$R^{99}$ is OMe;

M is

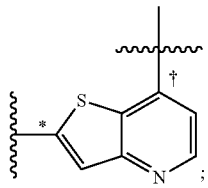 [SMILES: *c1cc2nccc(*)c2s1]

Z is —O—;

Ar is phenyl optionally substituted with 0 to 4 $R^2$ groups, for example phenyl substituted with one F; and G is

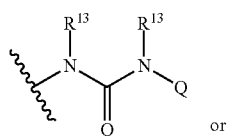

wherein $R^{13}$ is H; and

Q is cyclopropyl.

In some embodiments of the present invention,

D is pyridyl substituted with —$C_0$-$C_6$alkyl-(optionally substituted heterocycle);

M is

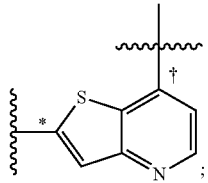 [SMILES: *c1cc2nccc(*)c2s1]

Z is —O—;

Ar is phenyl optionally substituted with 0 to 4 $R^2$ groups, for example phenyl substituted with one F; and G is

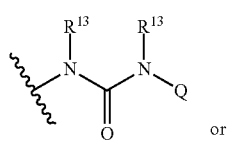

wherein $R^{13}$ is H; and

Q is cyclopropyl.

In some embodiments of the present invention,

D is pyridyl substituted with —$C_0$-$C_6$alkyl-(heterocycle optionally substituted with one or two oxo), for example —$CH_2$-(5- or 6-membered heterocyclyl substituted with 0, 1 or 2 oxo);

M is

Z is —O—;
Ar is phenyl optionally substituted with 0 to 4 $R^2$ groups, for example phenyl substituted with one F; and
G is wherein
$R^{13}$ is H; and
Q is cyclopropyl.

In some embodiments of the present invention,
D is pyridyl substituted with

M is

Z is —O—;
Ar is phenyl optionally substituted with 0 to 4 $R^2$ groups, for example phenyl substituted with one F; and G is wherein
$R^{13}$ is H; and
Q is cyclopropyl.

In some embodiments of the present invention,
D is pyridyl substituted with —$(CH_2)_i NR^{39}(CH_2)_i$ $[O(CH_2)_i]_x(CH_2)_j R^{99}$;
$R^{99}$ is OMe;
M is Z is —O—;
Ar is phenyl optionally substituted with 0 to 4 $R^2$ groups, for example phenyl substituted with one F; and
G is wherein
$R^{13}$ is H; and
Q is cyclopropyl.

In some embodiments of the present invention,
D is imidazolyl subsituted with one $C_1$-$C_6$alkyl and one —$(CH_2)_j NR^{39}(CH_2)_n R^{36}$;
M is Z is —O—;
Ar is phenyl optionally substituted with 0 to 4 $R^2$ groups, for example one F; and G is

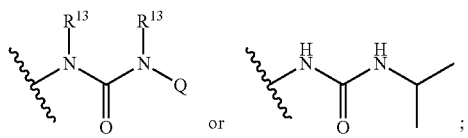

wherein Q is optionally substituted with from 0 to 4 independently selected $R^{20}$.

In some embodiments of the present invention,

D is imidazolyl subsituted with one $C_1$-$C_6$alkyl and one —$(CH_2)_j NR^{39}(CH_2)_n R^{36}$;

M is

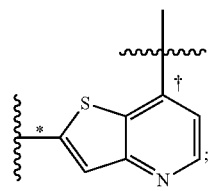 [SMILES: *c1cc2nccc(*)c2s1]

Z is —O—;

Ar is phenyl optionally substituted with 0 to 4 $R^2$ groups, for example phenyl substituted one F; and G is

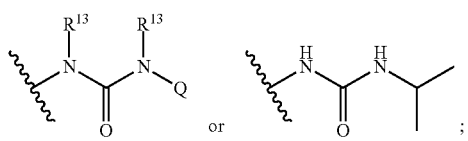

wherein $R^{13}$ is H; and

Q is phenyl optionally substituted with from 0 to 4 independently selected $R^{20}$.

In some embodiments of the present invention,

D is imidazolyl subsituted with one $C_1$-$C_6$alkyl and one —$(CH_2)_j NR^{39}(CH_2)_n R^{36}$;

M is

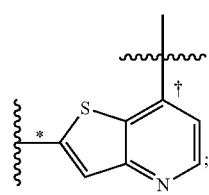 [SMILES: *c1cc2nccc(*)c2s1]

Z is —O—;

Ar is phenyl optionally substituted with 0 to 4 $R^2$ groups, for example phenyl substituted with one F; and G is

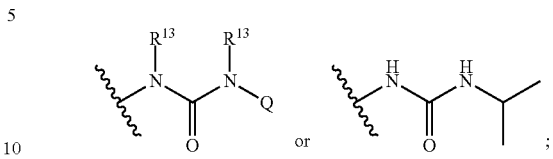

wherein $R^{13}$ is H; and

Q is phenyl optionally substituted with one or two groups independently selected from the group consisting of —P(O)Me$_2$, methyl, halo (for example F), trihalomethyl (for example trifluoromethyl), methoxy, —C(O)NH$_2$ and heteroaryl (for example oxazolyl), or Q is cyclopropyl.

Compounds of above formulas may generally be prepared according to the following Schemes. Tautomers and solvates (e.g., hydrates) of the compounds of above formulas are also within the scope of the present invention. Methods of solvation are generally known in the art. Accordingly, the compounds of the present invention may be in the free, hydrate or salt form, and may be obtained by methods exemplified by the following schemes below.

The following examples and preparations describe the manner and process of making and using the invention and are illustrative rather than limiting. It should be understood that there may be other embodiments which fall within the spirit and scope of the invention as defined by the claims appended hereto.

Compounds according to the invention include but are not limited to those described in the examples below. Compounds were named using Chemdraw Ultra version 10.0 or version 8.0.3, which are available through Cambridgesoft.com, 100 Cambridge Park Drive, Cambridge, Mass. 02140, or were derived therefrom.

The data presented herein demonstrate the inhibitory effects of the kinase inhibitors of the invention. These data lead one to reasonably expect that the compounds of the invention are useful not only for inhibition of kinase activity, protein tyrosine kinase activity, or embodiments thereof, such as, VEGF receptor signaling, but also as therapeutic agents for the treatment of proliferative diseases, including cancer and tumor growth and opthalmological diseases, disorders and conditions.

Synthetic Schemes and Experimental Procedures

The compounds of the invention can be prepared according to the reaction schemes or the examples illustrated below utilizing methods known to one of ordinary skill in the art. These schemes serve to exemplify some procedures that can be used to make the compounds of the invention. One skilled in the art will recognize that other general synthetic procedures may be used. The compounds of the invention can be prepared from starting components that are commercially available. Any kind of substitutions can be made to the start-

PARTICULAR EXAMPLES

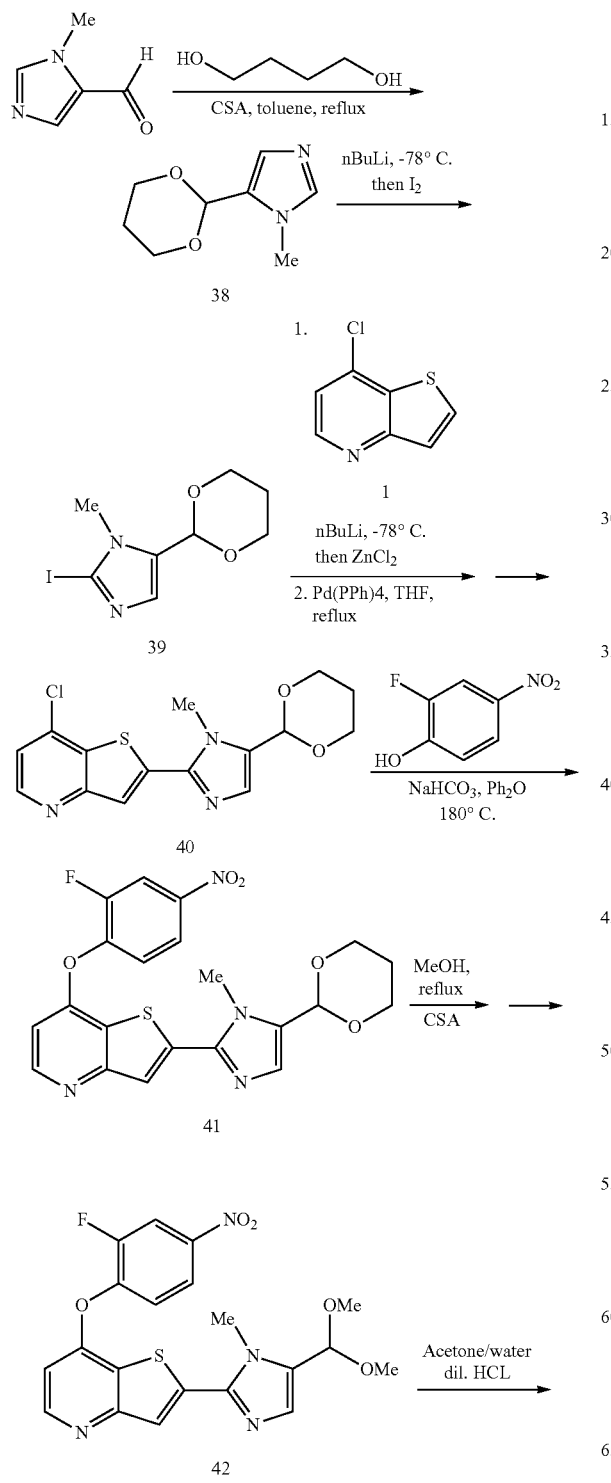

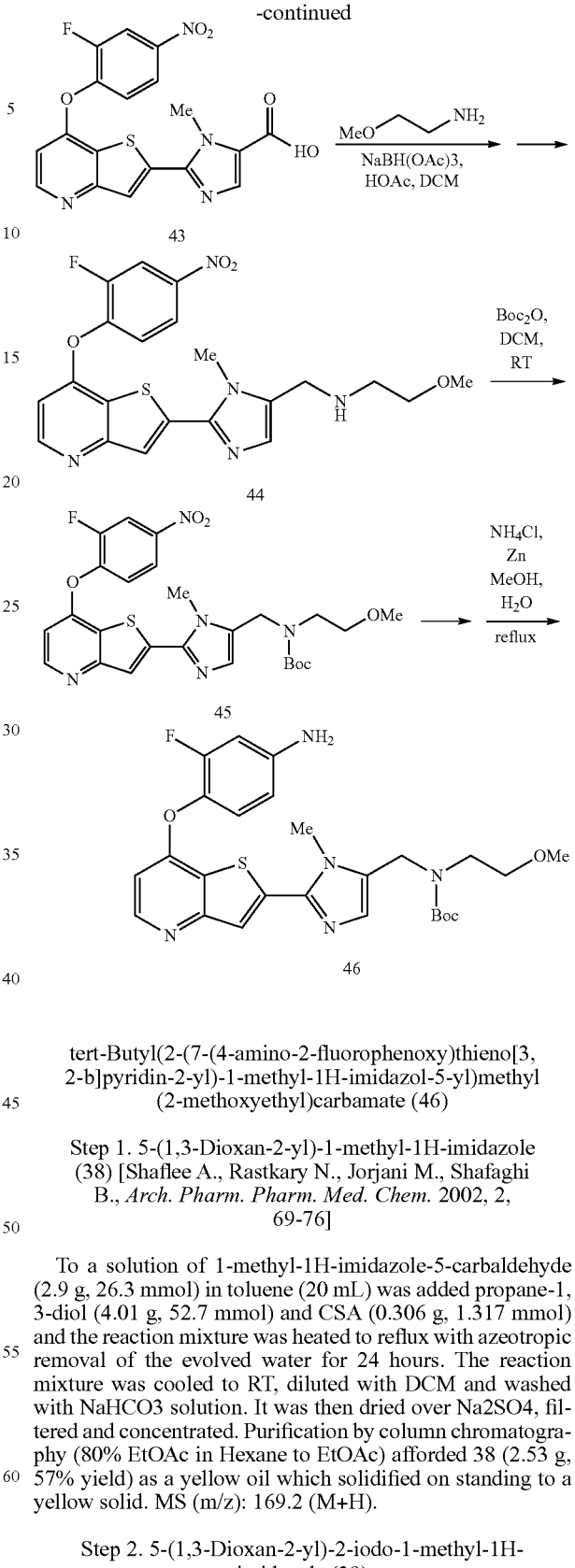

tert-Butyl(2-(7-(4-amino-2-fluorophenoxy)thieno[3,2-b]pyridin-2-yl)-1-methyl-1H-imidazol-5-yl)methyl (2-methoxyethyl)carbamate (46)

Step 1. 5-(1,3-Dioxan-2-yl)-1-methyl-1H-imidazole (38) [Shaflee A., Rastkary N., Jorjani M., Shafaghi B., *Arch. Pharm. Pharm. Med. Chem.* 2002, 2, 69-76]

To a solution of 1-methyl-1H-imidazole-5-carbaldehyde (2.9 g, 26.3 mmol) in toluene (20 mL) was added propane-1,3-diol (4.01 g, 52.7 mmol) and CSA (0.306 g, 1.317 mmol) and the reaction mixture was heated to reflux with azeotropic removal of the evolved water for 24 hours. The reaction mixture was cooled to RT, diluted with DCM and washed with NaHCO3 solution. It was then dried over Na2SO4, filtered and concentrated. Purification by column chromatography (80% EtOAc in Hexane to EtOAc) afforded 38 (2.53 g, 57% yield) as a yellow oil which solidified on standing to a yellow solid. MS (m/z): 169.2 (M+H).

Step 2. 5-(1,3-Dioxan-2-yl)-2-iodo-1-methyl-1H-imidazole (39)

To a solution of 38 (295 g, 1.754 mmol) in dry THF (10 mL) at −78° C. was added n-BuLi (0.772 mL, 1.929 mmol, 2.5 M solution in hexanes) and the reaction mixture was stirred for 20 min. Iodine (445 mg, 1.754 mmol) in THF (2 mL) was slowly added dropwise while maintaining the temperature at −78° C. and the reaction mixture was stirred for a further 30 min, and was quenched by the addition of water and then extracted with EtOAc. The organic phase was, washed with sodium thiosulfate solution, separated, dried over $Na_2SO_4$, filtered and concentrated. Purification by column chromatography (20% EtOAc/Hexane) afforded 39 (305 mg, 59% yield) as a white solid. MS (m/z): 294.1 (M+H).

Step 3. 2-(5-(1,3-Dioxan-2-yl)-1-methyl-1H-imidazol-2-yl)-7-chlorothieno[3,2-b]pyridine (40)

To a solution of 7-chlorothieno[3,2-b]pyridine (1) [Klemm, L. H.; Louris, J. N.; Boisvert, W.; Higgins, C.; Muchiri, D. R.; J. Heterocyclic Chem., 22, 1985, 1249-1252] (11.7 g, 69.0 mmol) in THF (300 mL) was added, at −78° C., a solution of n-BuLi (30.46 mL, 76 mmol, 2.5 M in hexanes) and the reaction mixture was stirred for 10 min. A solution of $ZnCl_2$ (76.15 mL, 76 mmol, 1.0 M in $Et_2O$) was added and the mixture was stirred at RT for 10 min. $Pd(PPh_3)_4$ (2.287 mg, 0.104 mmol) was added along with a solution of 39 (5.82 g, 19.79 mmol) in THF (20 mL) and the reaction mixture was heated to reflux under an atmosphere of $N_2$ gas for 4 hours. The reaction was then cooled to RT, and diluted with ammonium hydroxide and EtOAc. The organic phase was collected, dried over $Na_2SO_4$, filtered and concentrated. The resultant material was triturated with $Et_2O$ to afford the title compound 40 (5.79 g, 87% yield) as a white solid. MS (m/z): 336.1 (M+H).

Step 4. 2-(5-(1,3-Dioxan-2-yl)-1-methyl-1H-imidazol-2-yl)-7-(2-fluoro-4-nitrophenoxy)thieno[3,2-b]pyridine, (41)

A mixture of 40 (5.9 g, 17.57 mmol), 2-fluoro-4-nitrophenol (5.52 g, 35.1 mmol) and $NaHCO_3$ (1.346 g, 16.02 mmol) in $Ph_2O$ (7 mL) was heated to 180° C. for 4 hours. The reaction mixture was cooled to RT and diluted with DCM, filtered and concentrated. Purification of the residue by column chromatography (eluent EtOAc) afforded 41 (2.5 g, 31% yield) as a yellow solid. MS (m/z): 457.1 (M+H).

Step 5. 2-(5-(Dimethoxymethyl)-1-methyl-1H-imidazol-2-yl)-7-(2-fluoro-4-nitrophenoxy)thieno[3,2-b]pyridine (42)

To a solution of 41 (2.5 g, 5.48 mmol) in MeOH (200 mL) was added CSA (127 mg, 0.548 mmol) and the reaction mixture was heated to reflux for 5 hours. It was then cooled to RT and solid $NaHCO_3$ was added. The mixture was filtered and the filtrate was concentrated to dryness. The residual solid was dissolved in DCM, washed with water, dried over $Na_2SO_4$, filtered and concentrated. The resultant solid was triturated with $Et_2O$ to afford 42 (1.8 g, 74% yield) which was used without any further purification. MS (m/z): 445.1 (M+H).

Step 6. 2-(7-(2-Fluoro-4-nitrophenoxy)thieno[3,2-b]pyridin-2-yl)-1-methyl-1H-imidazole-5-carbaldehyde (43)

To a solution 42 (1.8 g, 4.05 mmol) in acetone (100 mL) and water (100 mL) was added diluted HCl (20 mL, 2M, 40.0 mmol) and the reaction mixture was stirred at RT overnight. It was then concentrated to dryness. The residual solid was dissolved in DCM, washed with water, dried over $Na_2SO_4$, filtered and concentrated. The resultant solid was triturated with $Et_2O$ to afford 43 (1.3 g, 81% yield), which used without additional purification. MS (m/z): 399.2 (M+H).

Step 7. N-((2-(7-(2-Fluoro-4-nitrophenoxy)thieno[3,2-b]pyridin-2-yl)-1-methyl-1H-imidazol-5-yl)methyl)-2-methoxyethanamine (44)

To a suspension of 43 (1.3 g, 3.26 mmol) in dry DCM (50 mL) at RT was added 2-methoxyethanamine (1.226 g, 16.32 mmol), acetic acid (0.98 g, 16.32 mmol) and sodium triacetoxyborohydride (3.46 g, 16.32 mmol), and the reaction mixture was stirred at RT for 24 hours. It was then diluted with additional DCM and washed with saturated $NaHCO_3$ solution, dried over $Na_2SO_4$, filtered and concentrated to dryness to afford 44 (1.5 g, 100% yield) as an yellow oil which was used crude in the next step with no additional purification. MS (m/z): 458.2 (M+H).

Step 8. tert-Butyl(2-(7-(2-fluoro-4-nitrophenoxy)thieno[3,2-b]pyridin-2-yl)-1-methyl-1H-imidazol-5-yl)methyl(2-methoxyethyl)carbamate (45)

To a solution of 44 (1.5 g, 3.28 mmol) in DCM (50 mL) at RT was added $Boc_2O$ (1.073 mg, 4.92 mmol) and the reaction mixture was stirred at RT overnight. The mixture was concentrated to dryness and the residue was purified by column chromatography (eluent EtOAc) to afford 45 (1.3 g, 71% yield) as a yellow solid. MS (m/z): 558.2 (M+H).

Step 9. tert-Butyl(2-(7-(4-amino-2-fluorophenoxy)thieno[3,2-b]pyridin-2-yl)-1-methyl-1H-imidazol-5-yl)methyl(2-methoxyethyl)carbamate (46)

To a solution of 45 (1.1 g, 0.717 mmol) in MeOH (30 mL) and water (10 mL) was added ammonium chloride (211 mg, 3.95 mmol) and zinc (1.61 g, 17.76 mmol) and the reaction mixture was heated to reflux for 24 hours. The reaction mixture was cooled to RT then concentrated to dryness. The residue was partitioned between DCM and water and the organic phase was collected, dried over $Na_2SO_4$, filtered and concentrated to afford the title compound 46 (1.04 g, 100% yield), which was used crude in the next step with no additional purification. MS (m/z): 528.1 (M+H).

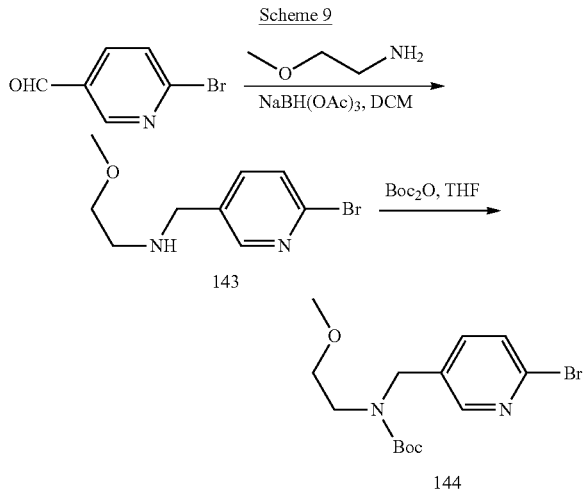

Scheme 9

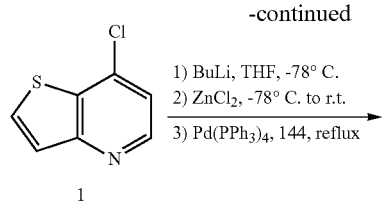

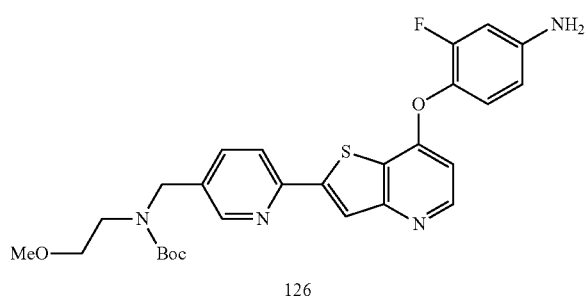

tert-Butyl(6-(7-(4-amino-2-fluorophenoxy)thieno[3,2-b]pyridin-2-yl)pyridin-3-yl)methyl(2-methoxyethyl)carbamate (126)

Step 1. N-((6-Bromopyridin-3-yl)methyl)-2-methoxyethanamine (143)

To a solution of 6-bromopyridine-3-carbaldehyde (5 g, 26.9 mmol) in DCM (40 mL). was added 2-methoxyethylamine (2.80 mL, 32.3 mmol). After 10 min, sodium triacetoxyborohydride (7.98 g, 37.6 mmol) was added to the mixture and it was stirred at r.t for 17 h. DCM (100 mL water (50 mL and NH₄Cl (50 mL) were added to the reaction mixture. The organic phase was collected and the aqueous layer was extracted with DCM (3×100 mL). The combined organic solutions were washed with brine and concentrated under reduce pressure. The residue was purified by flash column chromatography, eluent 98/2 to 95/5 DCM/MeOH, to afford title 143 (2.958 g, 45% yield) as a brown oil. $^1$H NMR (400 MHz, DMSO-d$_6$) δ (ppm): 8.31 (dd, J=2.6, 0.6 Hz, 1H), 7.70 (dd, J=8.2, 2.6 Hz, 1H), 7.58 (d, J=8.4 Hz, 1H), 3.69 (s, 2H), 3.37 (t, J=5.8 Hz, 2H), 3.22 (s, 3H), 2.60 (t, J=5.8 Hz, 2H). MS (m/z): 245.1 (M+H).

Step 2. tert-Butyl(6-bromopyridin-3-yl)methyl(2-methoxyethyl) carbamate (144)

To a solution of 143 (13.072 g, 53.3 mmol) in THF (40 mL) was added di-tert-butyl dicarbonate (14.86 mL, 64.0 mmol). The mixture was stirred at r.t. for 16 h and concentrated under reduce pressure. The residue was purified by flash column chromatography, eluent Hexane/EtOAc: 7/3, 6/4, 5/5, to afford title compound 144 (16.196 g, 88% yield) as a yellow oil. $^1$H NMR (400 MHz, DMSO-d$_6$) δ (ppm): 8.26 (dd, J=2.4, 0.8 Hz, 1H), 7.64-7.58 (m, 2H), 4.39 (s, 2H), 3.40-3.33 (m, 4H), 3.20 (s, 3H), 1.41-1.31 (m, 9H). MS (m/z): 345.2 (M+H).

Step 3. tert-Butyl(6-(7-chlorothieno[3,2-b]pyridin-2-yl)pyridin-3-yl)methyl(2-methoxyethyl)carbamate (145)

To a solution of 7-chlorothieno[3,2-b]pyridine (1) (8.84 g, 52.1 mmol) in THF (100 mL) at −78° C. was added n-butyllithium (20.86 mL, 52.1 mmol). After 30 min, zinc chloride (52.1 mL, 52.1 mmol) (1M in ether) was added at −78° C. and the reaction mixture was warmed to r.t. After 1 h, palladium tetrakistriphenylphosphine (1.004 g, 0.869 mmol) and 144 (6 g, 17.38 mmol) in THF (25 mL) were added and the mixture was heated to reflux for 1 h. It was then partitioned between saturated aqueous NaHCO₃ solution and EtOAc. The organic layer was collected and the aqueous layer was extracted with EtOAc (3×100mL). The combined organic layers were washed with brine and evaporated under reduce pressure. The residue was purified by flash column chromatography, eluents Hexane/EtOAc: 5/5, 3/7, 0/10, to afford compound 145 (5.41 g, 72% yield). $^1$H NMR (400 MHz, DMSO-d$_6$) δ (ppm): 8.65 (d, J=5.1 Hz, 1H), 8.52 (d, J=1.6 Hz, 1H), 8.39 (s, 1H), 8.27 (d, J=8.0 Hz, 1H), 7.80 (dd, J=8.1, 2.1 Hz, 1H), 7.58 (d, J=5.1 Hz, 1H), 4.48 (s, 2H), 3.43-3.35 (m, 4H), 3.22 (s, 3H), 1.43-1.33 (m, 9H). MS (m/z): 434.2 (M+H).

Step 4. tert-Butyl(6-(7-(4-amino-2-fluorophenoxy)thieno[3,2-b]pyridin-2-yl)pyridin-3-yl)methyl(2-methoxyethyl)carbamate (126)

To a solution of 4-amino-2-fluorophenol (1.933 g, 15.21 mmol) in DMSO (30 mL) was added potassium tert-butoxide (2.017 g, 17.97 mmol). After 30 min, chloride 145 (6 g, 13.83 mmol) was added and the reaction mixture was heated at 100° C. for 45 min. The mixture was cooled down then poured in water (250 mL) at 40-45° C. and stirred for 30 min. The precipitate was collected by filtration, washed with water (2×30 mL) and dried overnight. The crude solid was triturated with Et₂O (50 mL) for 1 h, to afford title compound 126 (4.18 g, 58% yield) as a brown solid. MS (m/z): 525.2 (M+H).

Scheme 14

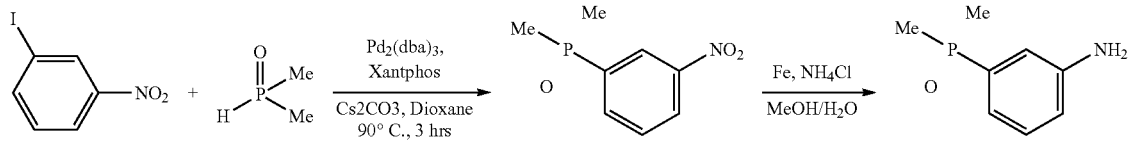

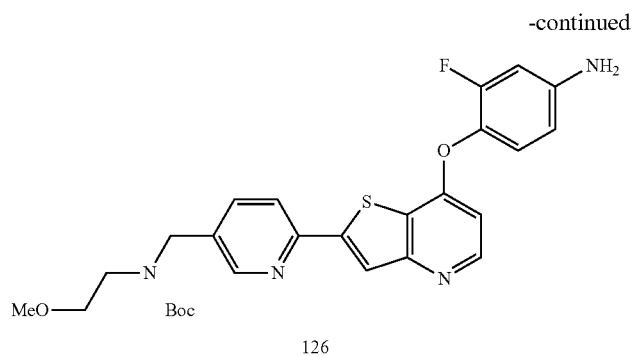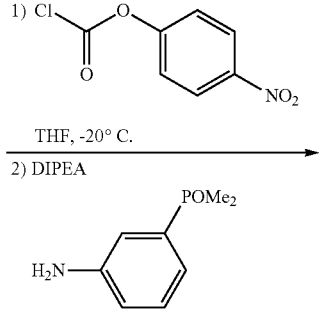

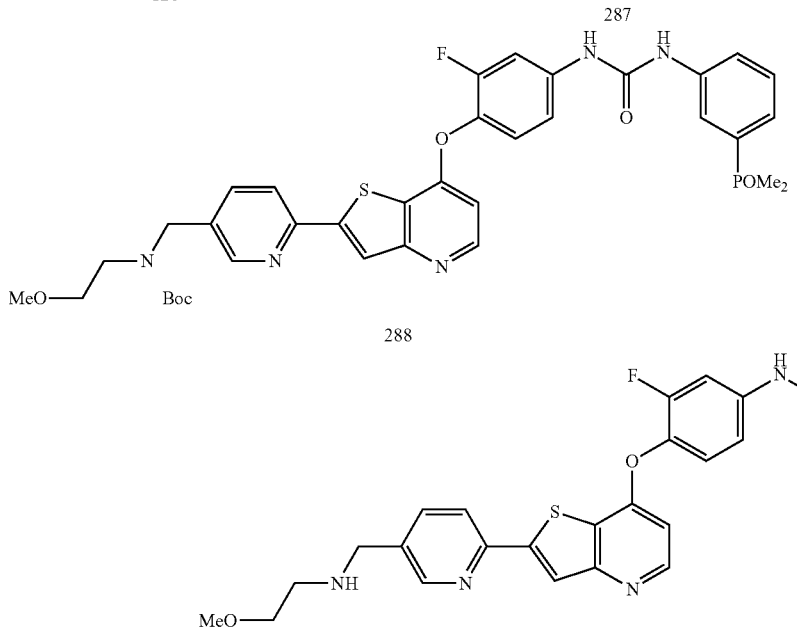

289: Example 179

Example 179

1-(3-(Dimethylphosphoryl)phenyl)-3-(3-fluoro-4-(2-(5-(((2-methoxyethylamino)methyl)pyridin-2-yl)thieno[3,2-b]pyridin-7-yloxy)phenyl)urea (289)

Step 1. 1-(dimethylphosphoryl)-3-nitrobenzene (286)

To a solution of 1-iodo-3-nitrobenzene (2.4 g, 9.6 mmol) in dry 1,4-dioxane (24 ml) in a pressure bottle under nitrogen at room temperature was added dimethylphosphine oxide [WO 2005/009348] (1.5 g, 19.2 mmol), $Pd_2(dba)_3$ (0.44 g, 0.48 mmol), Xantphos (0.56 g, 0.96 mmol) and cesium cabonate (4.38 g, 13.5 mmol). The mixture was degassed by bubbling nitrogen into the solution for 10 min. The pressure bottle was closed and heated at 90° C. for 3 h. The solvent was removed under reduced pressure and the residue was purified via Biotage (linear gradient 0-20%, methanol/ethyl acetate; 25M column) to afford title compound 286 as a brown solid (1.52 g, 7.63 mmol, 79%). MS (m/z): 200.1 (M+H).

Step 2. 3-(dimethylphosphoryl)aniline (287)

To a solution of compound 286 (1.5 g, 7.5 mmol) in methanol (62 ml) and water (12 ml) under nitrogen at room temperature was added ammonium chloride (0.604 g, 11.3 mmol) and iron (1.68 g, 30.1 mmol). The resulting mixture was heated to reflux for 30 min then filtered through celite. The celite pad was rinsed with methanol. The filtrate and washings were combined and concentrated and the residue was purified via Biotage (linear gradient 0-20%, methanol/dichloromethane; 25M column) to afford compound 287 as a yellow solid (1.27 g, 7.51 mmol, quantitative). MS (m/z): 170.1 (M+H).

Step 3. tert-butyl(6-(7-(4-(3-(3-(dimethylphosphoryl)phenyl)ureido)-2-fluorophenoxy)thieno[3,2-b]pyridin-2-yl)pyridin-3-yl)methyl(2-methoxyethyl)carbamate (288)

To a solution of compound 126 (schemes 6 or 9) (200 mg, 0.381 mmol) in dry tetrahydrofuran (8 mL) under nitrogen at –20° C. was added 4-nitrophenyl chloroformate (115 mg, 0.572 mmol). The reaction mixture was stirred at –20° C. for 2 h. A solution of 3-(dimethylphosphoryl)aniline 287 (97 mg, 0.57 mmol) and N,N'-diisopropylethylamine (0.200 mL, 1.14 mmol) in a mixture of dry tetrahydrofuran (2 mL) and dry N,N'-dimethylformamide (2 mL) were added at –20° C., the reaction mixture was allowed to warm to room temperature slowly, and the stirring was continued for an additional 16 h. The solvent was removed under reduced pressure; the residue was diluted with ethyl acetate, washed with a saturated aqueous solution of ammonium chloride, dried over anhydrous sodium sulfate and concentrated. Purification via Biotage (linear gradient 0-20%, methanol/dichloromethane; 25M column) afforded compound 288 (230 mg, 0.32 mmol, 84%). MS (m/z): 720.4 (M+H).

Step 4. 1-(3-(dimethylphosphoryl)phenyl)-3-(3-fluoro-4-(2-(5-((2-methoxyethylamino)methyl)pyridin-2-yl)thieno[3,2-b]pyridin-7-yloxy)phenyl)urea (289)

To a solution of compound 288 (230 mg, 0.32 mmol) in dichloromethane (7 mL) under nitrogen at room temperature was added trifluoroacetic acid (2.5 mL, 32 mmol). The reaction mixture was stirred for 16 h at room temperature. The solvent was removed under reduced pressure and a saturated aqueous solution of sodium bicarbonate was added. The aqueous phase was extracted with ethyl acetate (3×), the combined organic layers were concentrated. The residue was purified via Biotage (linear gradient 0-20%, methanol/dichloromethane; 25M column) to afford compound 289 as an off-white solid (75.3 mg, 0.122 mmol, 38.0%). $^1$H NMR (400 MHz, DMSO-$d_6$) δ (ppm): 9.15 (s, 1H), 9.06 (s, 1H), 8.57 (d, J=1.6 Hz, 1H), 8.53 (d, J=5.6 Hz, 1H), 8.31 (s, 1H), 8.23 (d, J=8.0 Hz, 1H), 7.92-7.83 (m, 2H), 7.76 (dd, J=13.2, 2.4 Hz, 1H), 7.67-7.62 (m, 1H), 7.49-7.42 (m, 2H), 7.41-7.33 (m, 1H), 7.32-7.26 (m, 1H), 6.67 (d, J=5.6 Hz, 1H), 3.78 (s, 2H), 3.54-3.34 (2H, hidden under water signal), 3.24 (s, 3H), 2.65 (t, J=5.6 Hz, 2H), 1.65 (d, J=13.2 Hz, 6H). MS (m/z): 620.4 (M+H).

Example 180

1-(4-(Dimethylphosphoryl)phenyl)-3-(3-fluoro-4-(2-(5-((2-methoxyethylamino)methyl)pyridin-2-yl)thieno[3,2-b]pyridin-7-yloxy)phenyl)urea (290)

Compound 290 was obtained by following the procedures described above for the compound 289 (Example 179). Characterization of compound 290 and compounds 295-300 are provided in the Table 1.

TABLE 1

| Cpd | Ex | STRUCTURE | CHARACTERIZATION |
|---|---|---|---|
| 290 | 180 | 1-(4-(dimethylphosphoryl)phenyl)-3-(3-fluoro-4-(2-(5-((2-methoxyethylamino)methyl)pyridin-2-yl)thieno[3,2-b]pyridin-7-yloxy)phenyl)urea | $^1$H NMR (400 MHz, DMSO-$d_6$) δ (ppm): 9.38 (s, 1H), 9.29 (s, 1H), 8.57 (s, 1H), 8.52 (d, J = 5.6 Hz, 1H), 8.32 (s, 1H), 8.23 (d, J = 8.0 Hz, 1H), 7.89 (d, J = 6.0 Hz, 1H), 7.77 (d, J = 13.4 Hz, 1H), 7.70-7.65 (m, 2H), 7.62-7.59 (m, 2H), 7.46 (t, J = 8.8 Hz, 1H), 7.28 (d, J = 10.0 Hz, 1H), 6.67 (d, J = 5.6 Hz, 1H), 3.78 (s, 2H), 3.40 (t, J = 5.8 Hz, 2H), 3.24 (s, 3H), 2.65 (t, J = 5.8 Hz, 2H), 1.61 (d, J = 13.2 Hz, 6H), one NH is not seen in the spectrum. MS (m/z): 620.3 (M + H). |
| 295 | 185 | 1-(4-(2-(5-5,8,11-Trioxa-2-azadodecylpyridin-2-yl)thieno[3,2-b]pyridin-7-yloxy)-3-fluorophenyl)-3-(2-fluoro-5-(trifluoromethyl)phenyl)urea | $^1$H NMR (400 MHz, DMSO-$d_6$) δ (ppm): 1H: 9.54 (s, 1H); 9.03 (s, 1H); 8.58-8.56 (m, 2H); 8.51 (d, J = 5.5, 1H); 8.31 (s, 1H); 8.22 (d, J = 8.4, 1H); 7.88 (dd, J = 7.8, 1.8, 1H); 7.76 (dd, J = 12.9, 2.4, 1H); 7.53-7.41 (m, 3H); 7.26-7.24 (m, 1H); 6.66 (d, J = 5.5, 1H); 3.78 (s, 2H); 3.50-3.44 (m, 8H); 3.40-3.37 (m, 2H); 3.20 (s, 3H); 2.66-2.62 (m, 2H). MS (M/Z): (calc.) 718.2 (found) 718.4 |
| 296 | 186 | N1-(4-(2-(5-5,8,11-Trioxa-2-azadodecylpyridin-2-yl)thieno[3,2-b]pyridin-7-yloxy)-3-fluorophenyl)-N3-methyl-N3-phenylmalonamide | $^1$H NMR (400 MHz, DMSO-$d_6$) δ (ppm): 1H: 10.29 (s, 1H); 8.55 (d, J = 1.4, 1H); 8.49 (d, J = 5.5, 1H); 8.30 (s, 1H); 8.21 (d, J = 7.8, 1H); 7.87 (dd, J = 8.2, 1H); 7.77 (d, J=12.5, 1H); 7.49-7.29 (m, 7H); 6.64 (d, J = 5.3, 1H); 3.76 (s, 2H); 3.50-3.43 (m, 8H); 3.41-3.38 (m, 2H); 3.22-3.18 (m, 8H); 2.63 (t, J = 5.9, 2H). MS (M/Z): (calc.) 688.3 (found) 688.5 |

TABLE 1-continued

| Cpd | Ex | STRUCTURE | CHARACTERIZATION |
|---|---|---|---|
| 297 | 187 | 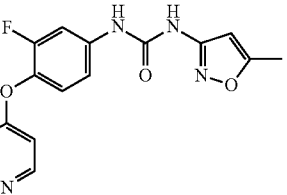<br>1-(4-(2-(5-5,8,11-Trioxa-2-azadodecylpyridin-2-yl)thieno[3,2-b]pyridin-7-yloxy)-3-fluorophenyl)-3-(5-methylisoxazol-3-yl)urea | $^1$H NMR (400 MHz, DMSO-d$_6$) δ (ppm): 1H: 9.69 (s, 1H); 9.25 (s, 1H); 8.58 (s, 1H); 8.52 (d, J = 5.3, 1H); 8.32 (s, 1H); 8.23 (d, J = 8.0, 1H); 7.92-7.88 (m, 1H); 7.74 (dd, J = 13.1, 2.5, 1H); 7.47 (t, J = 9.0, 1H); 7.30-7.26 (m, 1H); 6.66 (d, J = 5.9, 1H); 6.56 (d, J = 0.9, 1H); 3.80 (s, 2H); 3.52-3.47 (m, 8H); 3.42-3.38 (m, 2H); 3.22 (s, 3H); 2.68-2.64 (m, 2H); 2.37 (d, J = 1.0, 3H). MS (M/Z): (calc.) 637.2 (found) 637.4 |
| 300 | 190 | 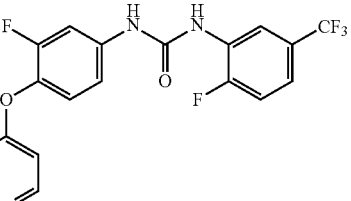<br>(E)-1-(3-Fluoro-4-(2-(5-((4-methylpiperazin-1-ylimino)methyl)pyridin-2-yl)thieno[3,2-b]pyridin-7-yloxy)phenyl)-3-(2-fluoro-5-(trifluoromethyl)phenyl)urea | $^1$H NMR (400 MHz, DMSO-d$_6$) δ (ppm): 1H: 9.73 (s, 1H); 9.20 (d, J = 2.5, 1H); 8.75 (d, J = 2.0, 1H); 8.57 (dd, J = 7.7, 2.2, 1H); 8.53 (d, J = 5.5, 1H); 8.33 (s, 1H); 8.26-8.24 (m, 2H); 8.06 (dd, J = 8.4, 2.0, 1H); 7.78 (dd, J = 13.1, 2.5, 1H); 7.69 (s, 1H); 7.54-7.43 (m, 3H); 7.30-7.26 (m, 1H); 6.67 (d, J = 5.5, 1H); 5.76 (s, 2H); 3.22-3.16 (m, 4H); ~2.54 (m, 4H?, obscured by DMSO peak); 2.24 (s, 3H). MS: (calc.) 668.2 (found) 668.3 (MH)+ |

Scheme 16

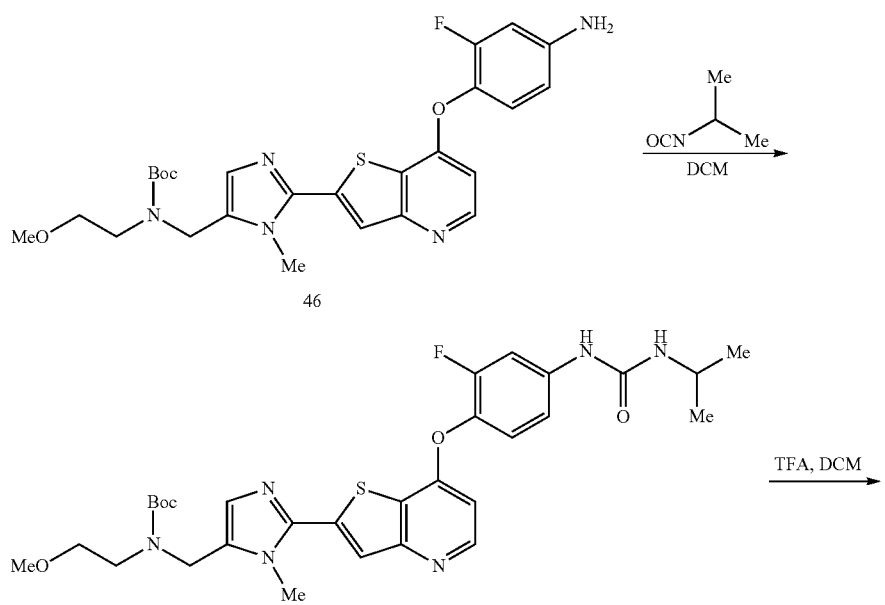

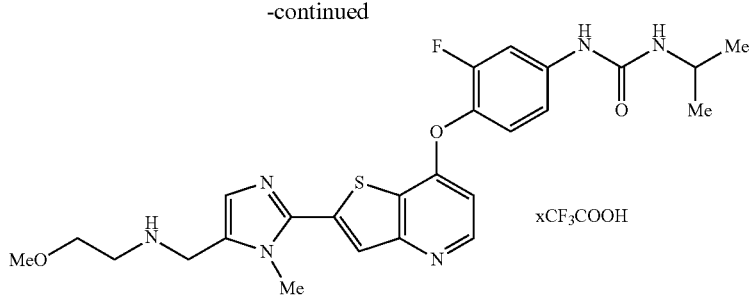

315: Example 202

Example 202

Step 1. tert-Butyl(2-(7-(2-fluoro-4-(3-isopropylureido)phenoxy)thieno[3,2-b]pyridin-2-yl)-1-methyl-1H-imidazol-5-yl)methyl(2-methoxyethyl)carbamate (314)

The reaction mixture of aniline 46 (200 mg, 0.379 mmol) and 2-isocyanatopropane (64.5 mg, 0.758 mmol) was heated to 100° C. for 15 min in a microwave reactor. The reaction mixture was loaded directly into Biotage (Silicycle, HR, 12 g column, 50-100% EA/Hexane, then MeOH/EA, 0-20%). The collected fractions afforded the desired product 314 (150 mg, 0.245 mmol, 64.6% yield) as a white solid. MS: 613(MH)+, very weak signal.

Step 2. 1-(3-Fluoro-4-(2-(5-((2-methoxyethylamino)methyl)-1-methyl-1H-imidazol-2-yl)thieno[3,2-b]pyridin-7-yloxy)phenyl)-3-isopropylurea (315)

The solution of urea 314 (150 mg, 0.245 mmol) and TFA (1 mL, 12.98 mmol) in DCM (20 mL) was stirred 4 hr at room temperature and concentrated. The residue was partitioned between EtOAc/NaHCO$_3$ sat. solution. The solid was collected by filtration and combined with organic layer. The mixture was concentrated and the residue was purified via Biotage (EA/MeOH 0-40%, 12 g Silicycle HR column). Collected fractions gave the desired product 315 (70 mg, 0.137 mmol, 55.8% yield) as a white solid. $^1$HNMR (dmso-d$_6$) δ(ppm) 1H:8.67 (s, 1H), 8.48 (d, 1H, J=5.5 Hz), 7.91 (s, 1H), 7.65 (dd, 1H, J1=13.7 Hz, J2=2.6 Hz), 7.32 (t, 1H, J=9.0 Hz), 7.07 (m, 2H), 6.63 (d, 1H, J=5.5 Hz), 6.13 (d, 1H, J=7.6 Hz), 4.04 (s, br, 2H), 3.08 (s, 3H), 3.72 (m, 1H), 3.47 (t, 2H, J=5.2 Hz), 3.24 (s, 3H), 2.94 (m, 2H), 1.07 (s, 3H, 1.05 (s, 3H) (presumably a mono-TFA salt). MS: 513.4 (MH)+

Scheme 17

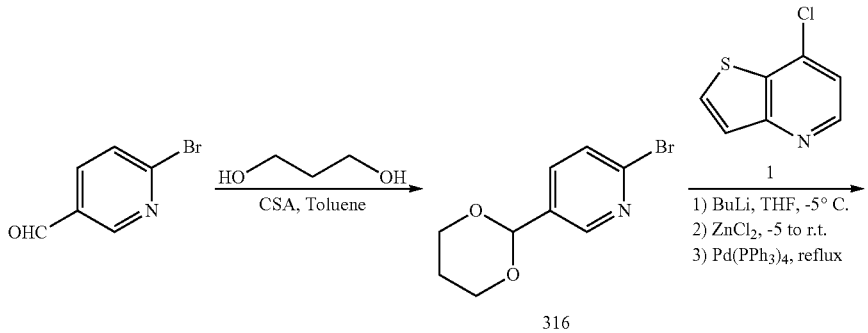

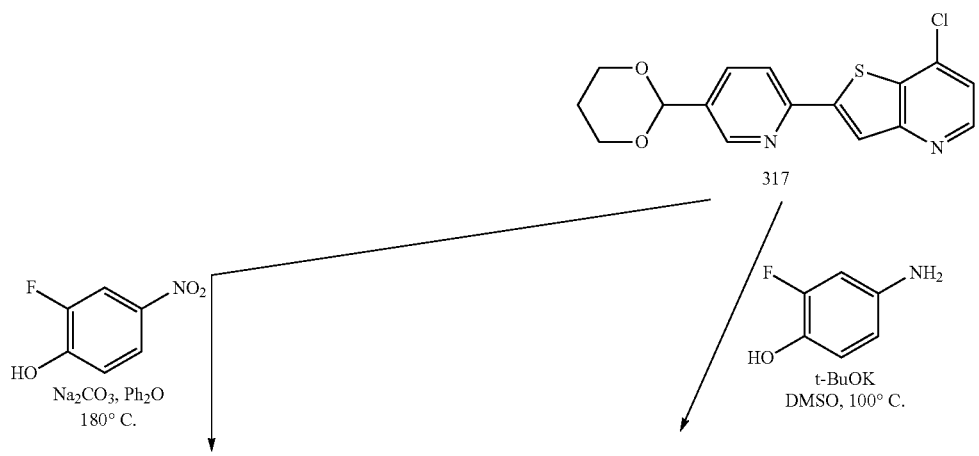

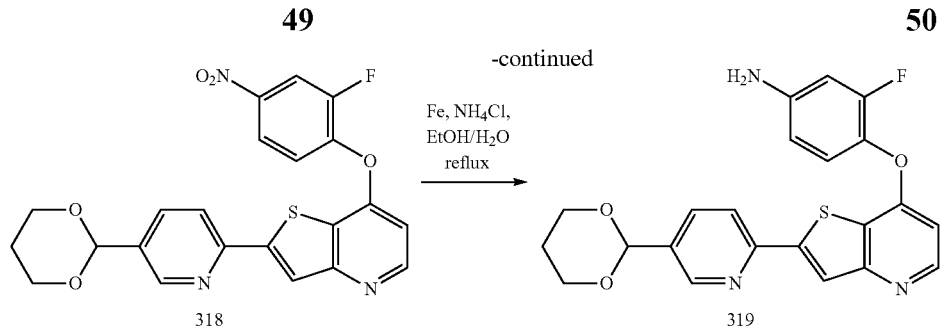

Step 4. 4-(2-(5-(1,3-Dioxan-2-yl)pyridin-2-yl)thieno[3,2-b]pyridin-7-yloxy)-3-fluoroaniline (319)

Step 1. 2-Bromo-5-(1,3-dioxan-2-yl)pyridine (316)

To a solution of 6-bromopyridine-3-carbaldehyde (25 g, 134 mmol) in toluene (130 mL) were added 1,3-propanediol (20.45 g, 269 mmol) and 10-camphorsulfonic acid (3.12 g, 13.44 mmol). The reaction mixture was heated to reflux, with azeotropic removal of the evolved water, for 50 minutes, cooled down to r.t. and concentrated. The residue was partitioned between EtOAc (150 mL) and saturated aqueous NaHCO$_3$ solution (100 mL). Organic phase was collected and the aqueous phase was extracted with EtOAc (2×150 mL). Combined organic fractions were washed with brine (100 mL), dried over Na$_2$SO$_4$, filtered and concentrated to yield a brown solid which was triturated with Et$_2$O and hexane (10/200 mL), to afford intermediate 316 (27.7 g, 84% yield) as a beige solid. MS (m/z): 244.1, 246.1 (M+H). $^1$H NMR (400 MHz, DMSO-d$_6$) δ (ppm): 8.40 (d, J=2.4 Hz, 1H), 7.35 (dd, J=8.0, 2.4 Hz, 1H), 7.66 (dd, J=8.0, 0.4 Hz, 1H), 5.61 (s, 1H), 4.15 (ddd, J=11.8, 5.0, 1.2 Hz, 2H), 3.98-3.91 (m, 2H), 2.028-1.95 (m, 1H), 1.46 (d quint, J=13.2, 1.2 Hz, 1H).

Step 2. 2-(5-(1,3-Dioxan-2-yl)pyridin-2-yl)-7-chlorothieno[3,2-b]pyridine (317)

To a solution of 7-chlorothieno[3,2-b]pyridine (1) (13.33 g, 79 mmol) in THF (204 mL) at −5° C./−10° C. was added n-BuLi (2.5 M in hexanes, 31.6 mL, 79 mmol) over 50 min. After 30 min, a solution of zinc chloride in ether (1M, 79 mL, 79 mmol) was added at −5° C./−10° C. over 50 min and the reaction mixture was allowed to warm-up to r.t. After 45 min, 2-bromo-5-(1,3-dioxan-2-yl)pyridine (316) (15.98 g, 65.5 mmol) and palladium tetrakistriphenylphosphine (2.27 g, 1.964 mmol) in THF (28 mL) were added and the mixture was heated to reflux for 2 h, cooled down to r.t., and concentrated. The residue was diluted with DCM (600 mL), H$_2$O (500 mL) and NH$_4$OH (100 mL), stirred at r.t. for 1 h and the phases were separated. The aqueous phase was extracted with DCM (2×100 mL); the combined organic phases were dried over anhydrous Na$_2$SO$_4$, filtered and concentrated. The residue was triturated with MTBE (150 mL), to afford intermediate 317 (12.796 g, 59% yield) as a beige solid. $^1$H NMR (400 MHz, DMSO-d$_6$) δ (ppm): 8.66-8.65 (m, 2H), 8.43 (d, J=0.8 Hz, 1H), 8.30 (d, J=8.4 Hz, 1H), 7.94 (d, J=8.4 Hz, 1H), 7.59 (dd, J=5.0, 0.6 Hz, 1H), 5.68 (s, 1H), 4.19 (dd, J=11.6, 4.8 Hz, 2H), 3.99 (t, J=11.4 Hz, 2H), 2.07-2.01 (m, 1H), 1.49 (d, J=13.2 Hz, 1H). MS (m/z): 333.1 (M+H).

Step 3. 2-(5-(1,3-Dioxan-2-yl)pyridin-2-yl)-7-(2-fluoro-4-nitrophenoxy)thieno[3,2-b]pyridine (318)

To a suspension of 317 (22.48 g, 67.5 mmol) in phenyl ether (65 mL) was added sodium carbonate (14.32 g, 135 mmol) and 2-fluoro-4-nitrophenol (15.92 g, 101 mmol). The reaction mixture was heated at 180° C. for 2 h, cooled down to 40° C., diluted with DCM (300 mL), stirred at r.t. for 15 min and filtered. The filtrate was collected and concentrated to a minimal volume; Et$_2$O (200 mL) was added and the formed suspension was stirred for 30 min. The solid material was collected by filtration, to afford intermediate 318 (25.20 g, 55.6 mmol, 82% yield) as a beige solid. $^1$H NMR (400 MHz, DMSO-d$_6$) δ (ppm): 8.63-8.62 (m, 2H), 8.48 (dd, J=10.6, 2.6 Hz, 1H), 8.43 (s, 1H), 8.31 (d, J=8.0 Hz, 1H), 8.21 (dt, J=8.8, 1.2 Hz, 1H), 7.94 (dd, J=8.4, 2.0 Hz, 1H), 7.71 (t, J=8.6 Hz, 1H), 6.98 (d, J=5.2 Hz, 1H), 5.67 (s, 1H), 4.19 (dd, J=10.8, 5.2 Hz, 2H), 3.98 (td, J=12.0, 2.0 Hz, 2H), 2.08-1.99 (m, 1H), 1.46 (d, J=13.6 Hz, 1H). MS (m/z): 454.2 (M+H).

Step 4. 4-(2-(5-(1,3-dioxan-2-yl)pyridin-2-yl)thieno[3,2-b]pyridin-7-yloxy)-3-fluoroaniline (319)

Method A

To a suspension of 318 (10 g, 22.05 mmol) in EtOH (216 ml) and water (108 ml) was added iron powder (10.47 g, 187 mmol) and ammonium chloride (1.015 g, 18.97 mmol). The mixture was heated to reflux for 30 min, filtered while hot and the solids were washed with ether (200 mL). The filtrate and washings were combined and concentrated to afford title compound 319 (9.62 g, 99% yield) as a beige solid. This material was used in the next step (Scheme 18) without additional purification. $^1$H NMR (400 MHz, DMSO-d$_6$) δ (ppm): 8.64 (d, J=2.0 Hz, 1H), 8.51 (dd, J=5.6, 2.0 Hz, 1H), 8.34 (s, 1H), 8.28 (dd, J=8.0, 0.8 Hz, 1H), 7.93 (dd, J=8.4, 2.0 Hz, 1H), 7.13 (t, J=9.0 Hz, 1H), 6.61 (dd, J=5.4, 0.6 Hz, 1H), 6.54 (dd, J=13.2, 2.4 Hz, 1H), 6.46 (ddd, J=8.8, 2.8, 0.6 Hz, 1H), 5.67 (s, 1H), 5.56 (s, 2H), 4.19 (dd, J=10.6, 5.0 Hz, 2H), 3.98 (td, J=12.0, 2.5 Hz, 2H), 2.09-1.99 (m, 1H), 1.49 (dt, J=13.2, 1.3 Hz, 1H). MS (m/z): 424.1 (M+H).

Method B

To a solution of 4-amino-2-fluorophenol (7.42 g, 58.4 mmol) in DMSO (65 mL) was added potassium tert-butoxide (7.75 g, 69.0 mmol)). After 30 min, intermediate 317 (17.67 g, 53.1 mmol) was added and the reaction mixture was heated at 100° C. for 1.5 h, cooled down to room temperature, poured in water (300 mL) at 40-45° C. and stirred for 30 min. The solid was collected by filtration, washed with water (2×30 mL) and dried for 2 h. This material was triturated with ether (60 mL), to afford title compound 319 (19.80 g, 88% yield) as a brown solid. MS (m/z): 424.1 (M+H).

Scheme 18
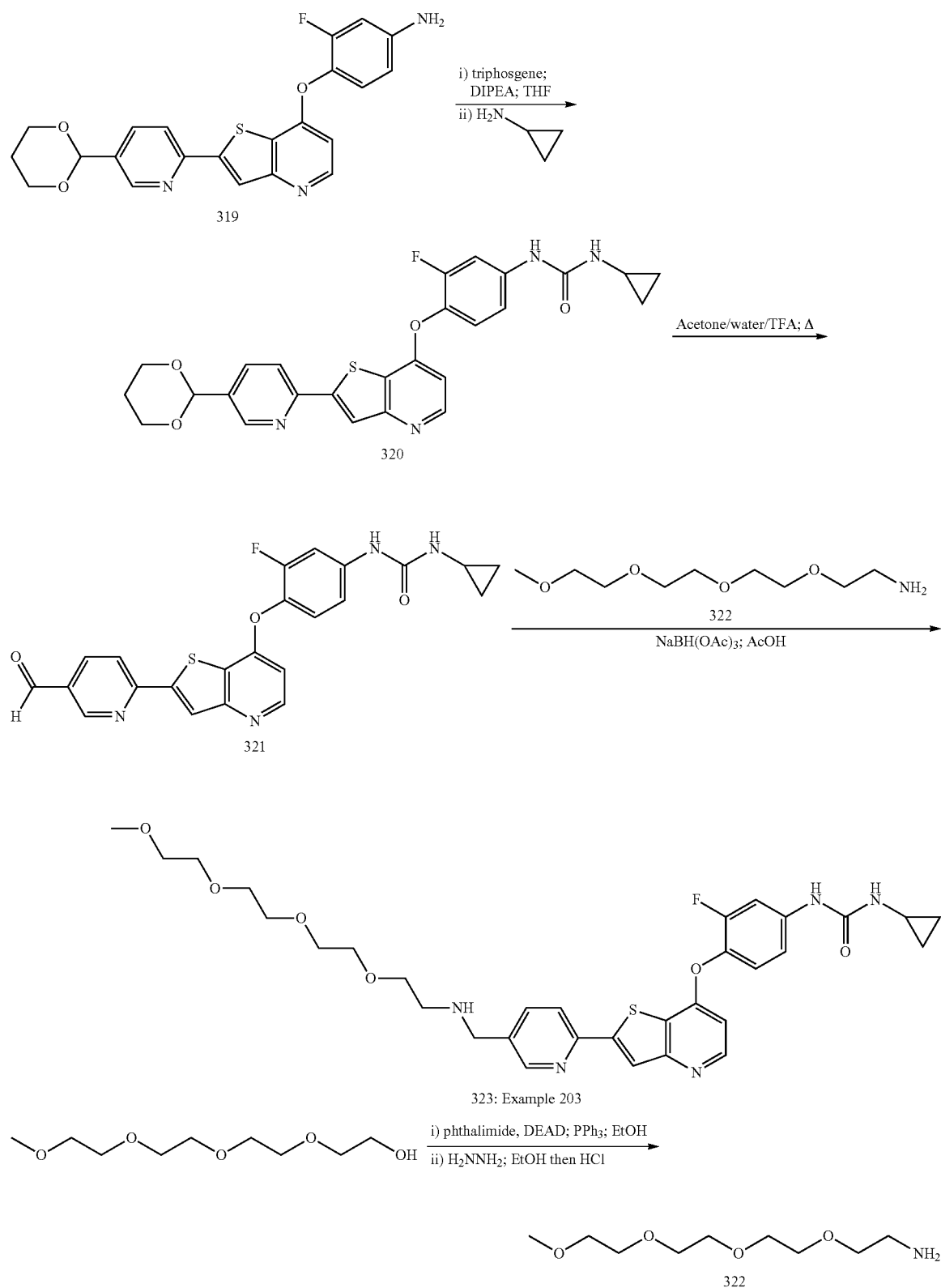

Example 203

1-(4-(2-(5-5,8,11,14-Tetraoxa-2-azapentadecylpyridin-2-yl)thieno[3,2-b]pyridin-7-yloxy)-3-fluorophenyl)-3-cyclopropylurea (323)

Step 1: 1-(4-(2-(5-(1,3-Dioxan-2-yl)pyridin-2-yl)thieno[3,2-b]pyridin-7-yloxy)-3-fluorophenyl)-3-cyclopropylurea (320)

A 100 mL round bottom flask was charged with 319 (0.55 g, 1.3 mmol) and DIPEA (0.91 mL, 5.2 mmol) in dry tetrahydrofuran (55 mL) to give a colorless solution. The reaction mixture was cooled to 0° C. then triphosgene (0.154 g, 0.520 mmol) was added. The reaction mixture was stirred for 1 h at 0° C. then cyclopropylamine (1.8 mL, 26 mmol) was added. Finally the reaction mixture was stirred at r.t. for 3 h then concentrated. The residue was partitioned between water and ethyl acetate, resulting in the formation a thick white solid. This was isolated by suction filtration, rinsed with water and ethyl acetate, and dried in vacuo to give crude 320 (0.65 g, 1.2 mmol, 99% yield) which was used without further purification. MS: 507.2 (M+H).

Step 2: 1-Cyclopropyl-3-(3-fluoro-4-(2-(5-formylpyrid in-2-yl)thieno[3,2-b]pyridin-7-yloxy)-3-fluorophenyl)-yloxy)phenyl)urea (321)

A suspension of 320 (0.65 g, 1.3 mmol) in 5:2:1 acetone/water/TFA (100 mL) was heated to reflux for 6 h. The mixture was then cooled and concentrated. The resulting solid residue was suspended in water, isolated by suction filtration, washed with ethyl acetate and dried in vacuo yielding 321 (0.49 g, 1.1 mmol, 85% yield) which was used without further purification in the next step. MS: 449.0 (M+H).

Step 3. 2,5,8,11-Tetraoxatridecan-13-amine (322)

Tetraethylene glycol monomethyl ether (10.0 mL, 47.5 mmol), phthalimide (7.20 g, 48.9 mmol), and triphenylphosphine (12.8 g, 48.8 mmol) were suspended in dry tetrahydrofuran (200 mL) to give a colorless suspension. Diethyl azodicarboxylate (8.0 mL, 50.5 mmol) was added dropwise by syringe, and the mixture was stirred at r.t. for 18 h. Then ethanol (50 mL) was added, the mixture was stirred for a further 30 min and then concentrated under reduced pressure. The residue was dissolved in 1:1 ethyl acetate/hexanes (100 mL), stirred at 0° C. for 2 h, and the resulting white precipitate was removed by suction filtration. The filtrate was concentrated (13.5 g, 40.0 mmol, 84% yield) and used in the next step without further purification.

The above crude product was dissolved in ethanol (100 mL) to give a colorless solution. Hydrazine hydrate (2.3 mL, 40 mmol) was added and the mixture was heated to reflux for 4 h. It was then cooled, concentrated HCl (10.0 mL) was added, and the mixture refluxed for 1 hour more. It was then cooled to r.t., the white precipitate removed by suction filtration, and the filtrate concentrated. The residue was partitioned between water and diethyl ether. The aqueous phase was extracted with ether (organic phase, containing mostly $PPh_3O$ by MS, was discarded), then basified with 3M NaOH (50 mL) to pH=13. The aqueous phase was saturated with sodium chloride and extracted repeatedly with dichloromethane (~10×50 mL). The organic extract was dried ($MgSO_4$) and concentrated to yield 322 (7.0 g, 33.8 mmol, 84% yield, 71% over 2 steps). This was used without further purification in subsequent step. MS (m+1)=208.1.

Step 4: 1-(4-(2-(5-5,8,11,14-Tetraoxa-2-azapentadecylpyridin-2-yl)thieno[3,2-b]pyridin-7-yloxy)-3-fluorophenyl)-3-cyclopropylurea (323)

To a suspension of carboxaldehyde 321 (0.45 g, 1.0 mmol) and amine 322 (1.4 g, 6.75 mmol) in dichloromethane (75 mL) was added acetic acid (0.12 mL, 2.0 mmol). The reaction mixture was stirred for 1 h, then sodium triacetoxyborohydride (0.64 g, 3.0 mmol) was added and the resulting mixture stirred for 18 h. The mixture was then partitioned between water and dichloromethane, washed with 1M NaOH and brine, dried ($MgSO_4$), filtered and concentrated under reduced pressure. The residue was purified by Gilson reverse phase HPLC (35-75% $MeOH/H_2O$, Aquasil $C_{18}$, 30 min) and lyophilized. The purified product (containing some formic acid from the HPLC) was partitioned between warm dichloromethane and 1M NaOH. The organic phase was dried ($MgSO_4$), filtered and concentrated to give title compound 323 (0.264 g, 0.413 mmol, 41.1% yield). $^1$H NMR (DMSO-$d_6$) δ(ppm) $^1$H: 8.80 (s, 1H); 8.57 (s, 1H); 8.51 (d, J=5.5, 1H); 8.31 (s, 1H); 8.23 (d, J=8.0, 1H); 7.89 (dd, J=8.0, 1.5, 1H); 7.73 (dd, J=13.5, 2.2, 1H); 7.38 (t, J=9.0, 1H); 7.20 (d, J=8.2, 1H); 6.67 (d, J=2.7, 1H); 6.64 (d, J=5.5, 1H); 3.78 (s, 2H); 3.56-45 (m, 12H); 3.41 (t, J=5.7, 2H); 3.21 (s, 3H); 2.66 (d, J=5.7, 2H); 2.58-2.51 (m, 1H); 0.66-0.62 (m, 2H); 0.44-0.41 (m, 2H). LRMS: 640.5 (M+H).

Scheme 19

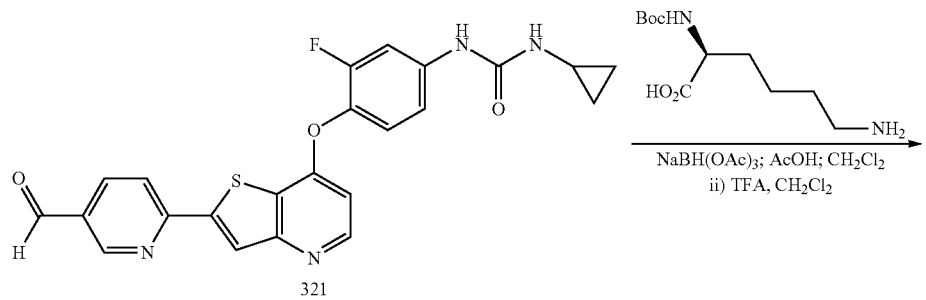

321

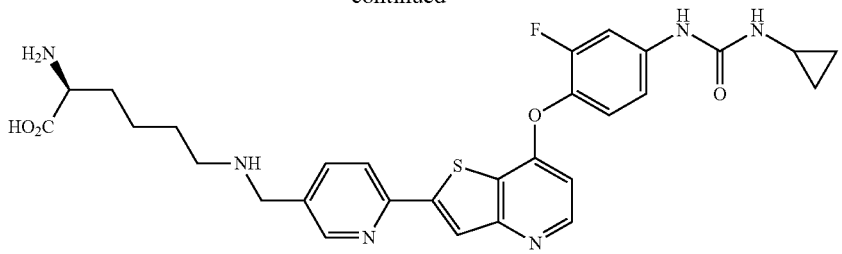

324: Example 204

Example 204

(S)-2-amino-6-((6-(7-(4-(3-cyclopropylureido)-2-fluorophenoxy)thieno[3,2-b]pyridin-2-yl)pyridin-3-yl)methylamino)hexanoic acid (324)

To a suspension of 321 (0.26 g, 0.58 mmol) and N-Boc-lysine (1.1 g, 4.6 mmol) in dichloromethane (75 mL) and was added acetic acid (0.066 mL, 1.2 mmol). The reaction mixture was stirred for 1 h, then sodium triacetoxyborohydride (0.37 g, 1.7 mmol) was added and the resulting mixture stirred for 18 h. The mixture was then partitioned between water and dichloromethane, and the solid precipitate removed by suction filtration through celite. The product was mostly in the solid filter cake, so this was solubilized by washing with 1:1 dichloromethane/methanol. This solution was concentrated and the residue was purified by Gilson reverse phase HPLC (35-75% MeOH/H$_2$O, Aquasil C$_{18}$, 30 min) and lyophilized to yield BOC-protected product. This was dissolved in dichloromethane (75 mL) and trifluoroacetic acid (3 mL), and stirred at r.t. for 3 h. The mixture was concentrated and the residue was purified by Gilson reverse phase HPLC (35-75% MeOH/H$_2$O, Aquasil C$_{18}$, 30 min) and lyophilized to yield title compound 324 (44 mg, 69% yield). $^1$H NMR (DMSO-d$_6$) δ(ppm) $^1$H: 9.02 (s, 1H); 8.66 (s, 1H); 8.53 (d, J=5.3, 1H); 8.35 (s, 1H); 8.28 (d, J=8.4, 1H); 7.98 (d, J=6.3, 1H); 7.72 (dd, J=13.5, 2.3, 1H); 7.37 (t, J=9.0, 1H); 7.21 (d, J=10.0, 1H), 6.89 (s, 1H); 6.68 (d, J=5.3, 1H); 4.00 (s, 2H); 2.75-2.70 (m, 2H); 2.55-2.52 (m, 1H); 2.45 (m, 1H); 1.70-1.30 (m. 6H); 0.67-0.62 (m, 2H); 0.44-0.40 (m, 2H). LRMS: 579.5 (M+H).

Scheme 20

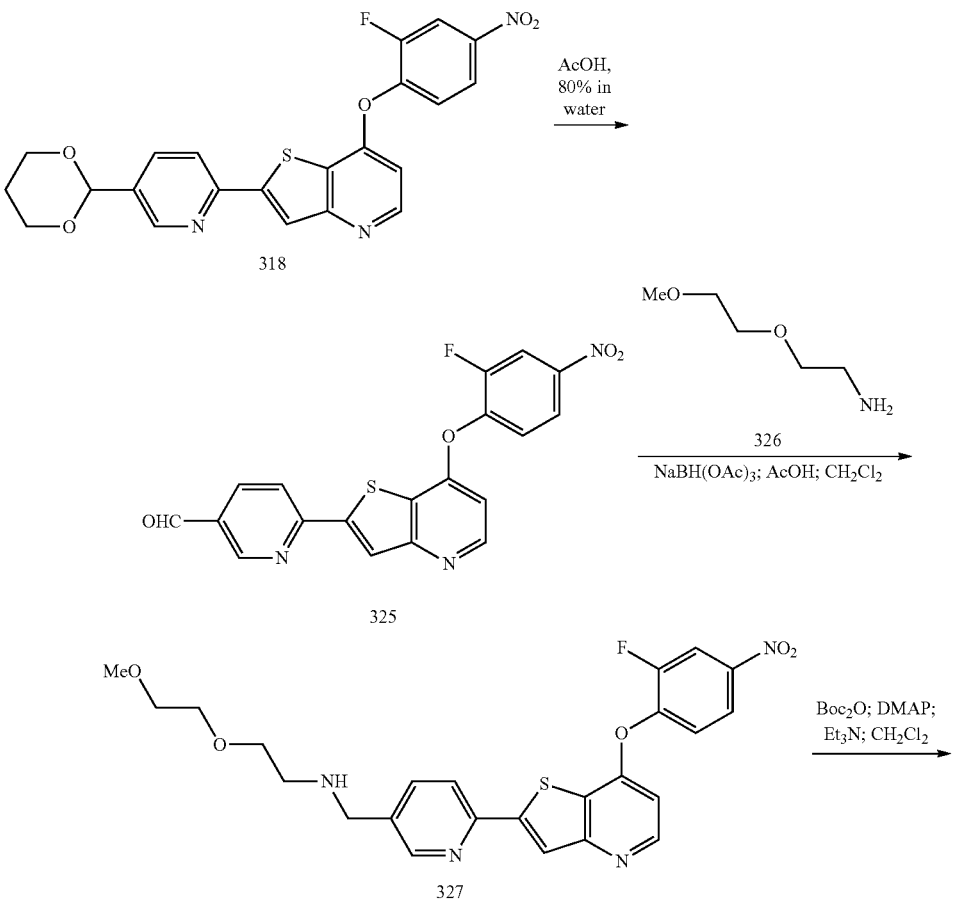

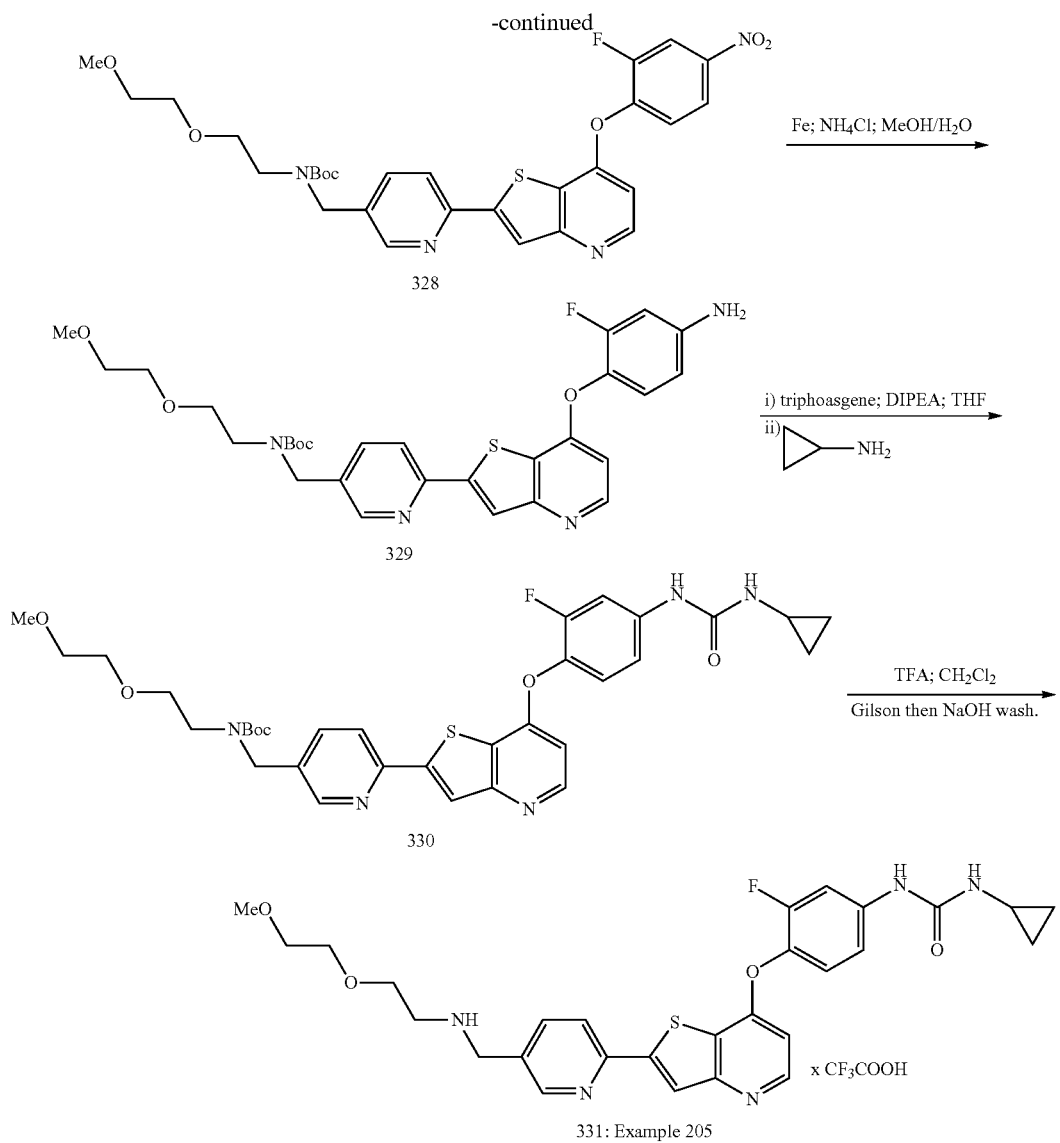

Example 205

1-Cyclopropyl-3-(3-fluoro-4-(2-(5-((2-(2-methoxyethoxy)ethylamino)methyl)pyridin-2-yl)thieno[3,2-b]pyridin-7-yloxy)phenyl)urea

Step 1: 6-(7-(2-fluoro-4-nitrophenoxy)thieno[3,2-b]pyridin-2-yl)nicotinaldehyde (325)

A suspension of 318 (2.64 g, 5.82 mmol) in 80% aqueous acetic acid (42 mL) was heated at 90° C. for 18 h. The reaction mixture was cooled to r.t. and diluted with water. The resulting precipitate was collected by suction filtration. The solid was transferred to a round-bottomed flask, the remaining water was removed by azeotropic distillation with toluene (4 times), and the solid dried in vacuo yielding 325 (1.76 g, 76%). LRMS (M+H): 396.3

Step 2: 2-(2-methoxyethoxy)ethanamine (326)

Diethylene glycol monomethyl ether (9.8 mL, 83 mmol), phthalimide (14.7 g, 100 mmol), and triphenylphosphine (26.2 g, 100 mmol) were suspended in dry tetrahydrofuran (200 mL) to give a colorless suspension (see scheme 18, step 3). Diethyl azodicarboxylate (15.8 mL, 100 mmol) was added dropwise by syringe, and the mixture was stirred at r.t. for 18 h. Then ethanol (50 mL) was added, the mixture was stirred for a further 30 min and then concentrated under reduced pressure. The residue was dissolved in 1:1 ethyl acetate/hexanes (100 mL), stirred at 0° C. for 2 h, and the resulting white precipitate was removed by suction filtration. The filtrate was concentrated and used in the next step without further purification.

The above crude product was dissolved in ethanol (200 mL) to give a colorless solution. Hydrazine hydrate (5.1 mL, 104 mmol) was added and the mixture was heated to reflux for 4 h. It was then cooled, concentrated HCl (16 mL) was added, and the mixture refluxed for 1 hour more. It was then was cooled to r.t., the white precipitate removed by suction filtration, and the filtrate concentrated. The residue was partitioned between water and ethyl acetate. The aqueous phase was extracted with ethyl acetate (organic phase, containing mostly PPh$_3$O by MS, was discarded), then basified with 3M NaOH (50 mL) to pH=13. The aqueous phase was saturated with sodium chloride and extracted repeatedly with dichloromethane (~10×50 mL). The organic extract was dried (MgSO$_4$) and concentrated to yield 326 (6.6 g, 56 mmol, 67% yield over 2 steps). This was used without further purification in subsequent reaction. MS (m+1)=120.2.

Step 3: N-((6-(7-(2-fluoro-4-nitrophenoxy)thieno[3,2-b]pyridin-2-yl)pyridin-3-yl)methyl)-2-(2-methoxyethoxy)ethanamine (327)

A suspension of carbaldehyde 325 (0.50 g, 1.3 mmol), amine 326 (0.30 g, 2.5 mmol) and acetic acid (0.14 ml, 2.5 mmol) in dichloromethane (20 ml) was stirred for 1 h at room temperature. Then sodium triacetoxyborohydride (0.80 g, 3.8 mmol) was added and stirred at r.t. for 16 h. A further amount of sodium triacetoxyborohydride (1.0 g) was then added, and stirring continued for 2 h. The reaction mixture was partitioned between dichloromethane and 1N NaOH. The yellow suspension was removed by filtration and rinsed with dichloromethane and 1N NaOH. The organic extract was dried over anhydrous sodium sulfate, filtered, and concentrated. The residue was purified via Biotage (linear gradient 0-20%, methanol/dichloromethane; Snap 100 g column) to yield 327 (280 mg, 0.562 mmol, 44%) as a yellow solid. LRMS (M+H): 499.4

Step 4: tert-butyl(6-(7-(2-fluoro-4-nitrophenoxy)thieno[3,2-b]pyridin-2-yl)pyridin-3-yl)methyl(2-(2-methoxyethoxy)ethyl)carbamate (328)

To compound 327 (0.28 g, 0.56 mmol) in dichloromethane (100 mL) at room temperature was added triethylamine (0.25 mL, 1.7 mmol), DMAP (0.017 g, 0.14 mmol) and Boc$_2$O (0.26 g, 1.1 mmol). The reaction mixture was stirred at room temperature for 2 h, then the mixture was washed sequentially with water, saturated ammonium chloride, and brine, dried over anhydrous magnesium sulfate, filtered, and concentrated. The residue was purified by silica gel chromatography (ethyl acetate) to afford compound 328 (0.20 g, 60% yield). LRMS (M+H): 599.5

Step 5: tert-butyl(6-(7-(4-amino-2-fluorophenoxy)thieno[3,2-b]pyridin-2-yl)pyridin-3-yl)methyl(2-(2-methoxyethoxy)ethyl)carbamate (329)

To nitro compound 328 (0.20 g, 0.33 mmol) in MeOH (75 mL) was added iron dust (0.37 g, 6.7 mmol) and ammonium chloride (0.089 g, 1.7 mmol) in water (5 mL). The resulting mixture was heated to reflux for 4 h, then cooled, filtered through celite and concentrated. The residue was partitioned between ethyl acetate and water, washed with brine, dried over anhydrous magnesium sulfate, filtered, and concentrated. The product 329 (0.18 g, 95%) was used crude in the next step. LRMS (M+H): 569.5

Step 6: tert-butyl(6-(7-(4-(3-cyclopropylureido)-2-fluorophenoxy)thieno[3,2-b]pyridin-2-yl)pyridin-3-yl)methyl(2-(2-methoxyethoxy)ethyl)carbamate (330)

To amine 330 (0.17 g, 0.30 mmol) and DIPEA (0.16 mL, 0.12 g, 0.90 mmol) in tetrahydrofuran (25 mL) at 0° C. was added triphosgene (0.035 g, 0.12 mmol) and the resulting solution was stirred for 1 h at 0° C. Cyclopropylamine (0.26 g, 4.6 mmol) was added and the mixture was warmed to room temperature and stirred for 18 h, then concentrated under reduced pressure. The residue was partitioned between dichloromethane and water, the organic phase was washed with sat. NH$_4$Cl$_{(aq)}$ and brine, dried over MgSO$_4$, filtered and concentrated, yielding crude 330 (0.15 g, 77% yield). LRMS (M+H): 652.6

Step 7: 1-Cyclopropyl-3-3-fluoro-4-(2-(5-((2-(2-methoxyethoxy)ethylamino)methyl)pyridin-2-yl)thieno[3,2-b]pyridin-7-yloxy)phenyl)urea (331)

Compound 330 (0.15 g, 0.23 mmol) was dissolved in dichloromethane (20 mL) and trifluoroacetic acid (0.9 mL) and the reaction mixture was stirred for 12 h at r.t. The mixture was concentrated and the residue was purified by Gilson reverse phase HPLC (40-80% MeOH/H$_2$O, Aquasil C$_{18}$, 30 min) and lyophilized. The purified product (containing some formic acid from the HPLC) was partitioned between warm dichloromethane and 1M NaOH. The organic phase was dried (MgSO$_4$), filtered and concentrated to give title compound 331 (0.110 g, 72% yield) (a mono-TFA salt despite the treatment with NaOH). $^1$H NMR (DMSO-d$_6$) δ(ppm) $^1$H: 8.84 (s, 1H); 8.65 (d, J=1.3, 1H); 8.53 (d, J=5.5, 1H); 8.37 (s, 1H); 8.30 (d, J=8.2, 1H); 7.99 (dd, J=8.2, 2.0, 1H); 7.73 (dd, J=13.7, 2.5, 1H); 7.38 (t, J=9.0, 1H); 7.22-7.18 (m, 1H); 6.68-6.64 (m, 2H); 4.03 (s, 2H); 3.60-3.52 (m, 4H); 3.48-3.44 (m, 2H); 3.25 (s, 3H); 2.92-2.88 (m, 2H); 2.55 (septet, J=3.1, 1H); 0.69-0.62 (m, 2H); 0.44-0.40 (m, 2H). LRMS: (M+H): 552.5.

Scheme 21

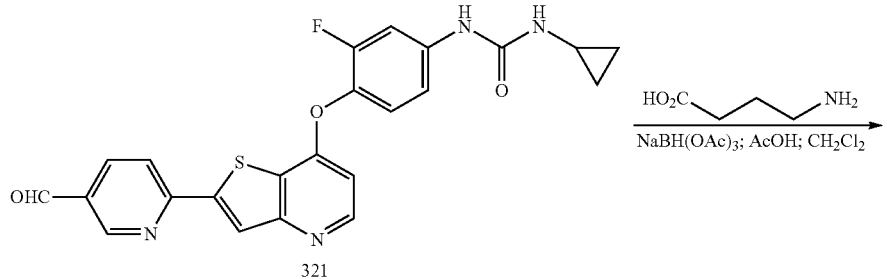

321

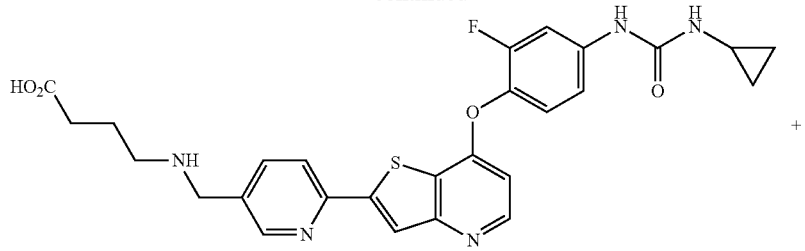

332: Example 206

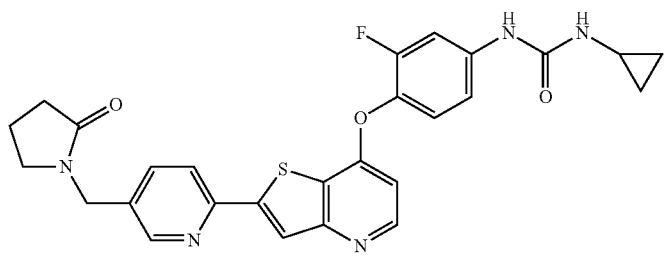

333: Example 207

Examples 206 and 207

4-((6-(7-(4-(3-Cyclopropylureido)-2-fluorophenoxy)thieno[3,2-b]pyridin-2-yl)pyridin-3-yl)methylamino)butanoic acid (332), and 1-cyclopropyl-3-(3-fluoro-4-(2-(5-((2-oxopyrrolidin-1-yl)methyl)pyridin-2-yl)thieno[3,2-b]pyridin-7-yloxy)phenyl)urea (333)

To a suspension of carbaldehyde 321 (0.20 g, 0.45 mmol) and 4-aminobutyric acid (1.0 g, 9.7 mmol) in dichloromethane (75 mL) and was added acetic acid (0.051 mL, 0.89 mmol). The reaction mixture was stirred for 1 h, then sodium triacetoxyborohydride (0.38 g, 1.8 mmol) was added and the resulting mixture stirred for 18 h. The mixture was then partitioned between water and dichloromethane, and the solid precipitate removed by suction filtration through celite. MS analysis indicated the cyclized product 333 was in the filtrate, while the acid product 332 was mostly in the solid filter cake. The organic phase from the filtrate was concentrated and the residue purified by silica gel chromatography (10% MeOH/ethyl acetate) to provide purified 333 (35 mg, 15% yield). The product in the celite filter cake was solubilized by washing with 1:1 dichloromethane/methanol. This solution was concentrated and the residue was purified by Gilson reverse phase HPLC (35-75% MeOH/H$_2$O, Aquasil C$_{18}$, 30 min) and lyophilized to afford acid 332 (44 mg, 69% yield). Characterization of compounds 332 and 333 is provided below.

Compound 332 (example 206): $^1$H NMR (DMSO-d$_6$) δ(ppm) $^1$H: 9.23 (s, 1H); 8.58 (s, 1H); 8.51 (d, J=5.4, 1H); 8.36 (s, 1H); 8.32 (s, 1H); 8.24 (d, J=8.2, 1H); 7.91 (dd, J=8.4, 2.0, 1H); 7.74 (dd, J=13.7, 2.3, 1H); 7.37 (t, J=9.0, 1H); 7.22 (d, J=9.0, 1H); 6.63 (d, J=5.3, 1H); 3.79 (s, 2H); 2.56 (t, J=5.1, 2H); 2.47-2.43 (m, 1H); 2.27 (t, J=7.2, 2H); 1.65 (quint, J=6.7, 2H); 0.66-0.61 (m, 2H); 0.44-0.40 (m, 2H). LRMS: (M+H) 536.4.

Compound 333 (example 207): $^1$H NMR (DMSO-d$_6$) δ(ppm) $^1$H: 8.76 (s, 1H); 8.52 (s, 1H); 8.52 (d, J=5.5, 1H); 8.35 (s, 1H); 8.26 (d, J=8.2, 1H); 7.79 (dd, J=8.2, 2.1, 1H); 7.73 (dd, J=13.5, 2.5, 1H); 7.38 (t, J=9.2, 1H); 7.20 (d, J=8.4, 1H); 6.65 (d, J=5.3, 1H); 6.62 (s, 1H); 4.46 (s, 2H); 3.30-3.20 (t, 2H, obscured by water peak?); 2.55 (quint, J=3.3, 1H); 2.31 (t, J=7.8, 2H); 1.95 (quint, J=7.6, 2H); 0.67-0.62 (m, 2H); 0.45-0.40 (m, 2H). LRMS: (M+H) 518.4

Scheme 22

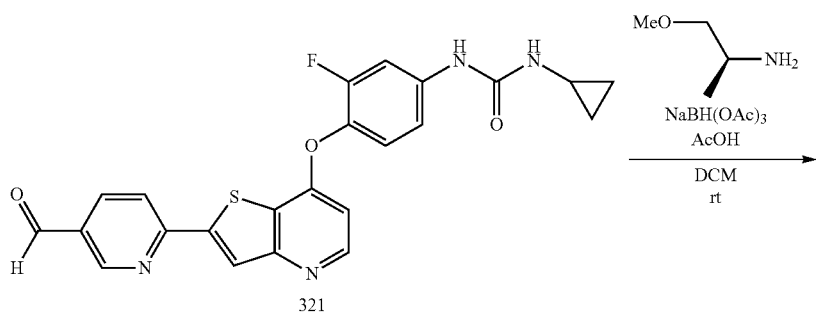

321

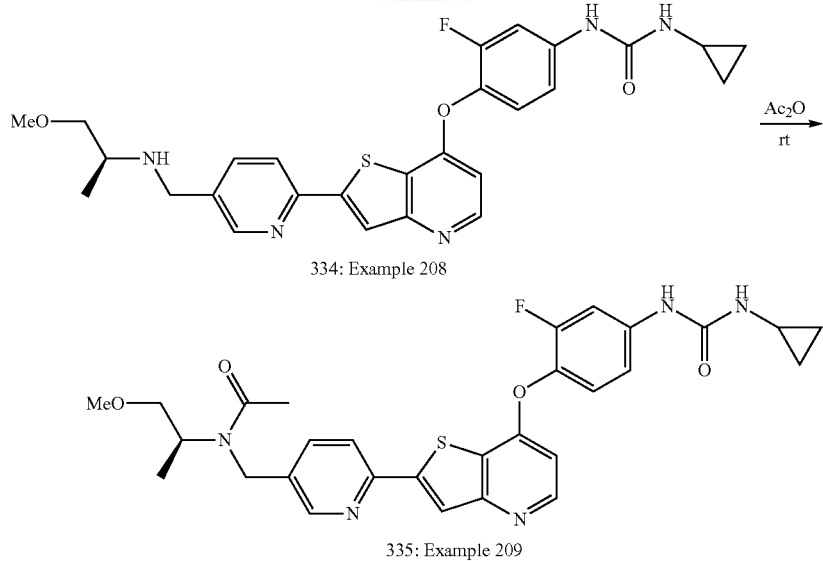

334: Example 208

335: Example 209

Examples 208 and 209

Step 1. (S)-1-cyclopropyl-3-(3-fluoro-4-(2-(5-((1-methoxypropan-2-ylamino)methyl)-pyridin-2-yl)thieno[3,2-b]pyridin-7-yloxy)phenyl)urea (334)

To a stirred suspension of carbaldehyde 321 (336 mg, 0.749 mmol), (S)-1-methoxy-2-aminopropane (200 mg, 2.248 mmol) and acetic acid (68 mg, 1.124 mmol) in DCM (20 ml) at rt under nitrogen was added NaBH(OAc)$_3$ (418 mg, 1.873 mmol). The reaction mixture was stirred at rt overnight and quenched with a solution of 10% HCl. The layers were separated; the aqueous layer was collected, washed twice with DCM and basified with 4N NaOH (pH 12) to form a suspension that was stirred for 30 min. The solid was collected by filtration, rinsed with water and air-dried and purified by flash column chromatography on silica gel (eluent 2% of ammonium hydroxyde in MeOH/DCM: 10/90) to afford the title compound 334 (182 mg, 0.35 mmol, 46% yield) as a yellow fluffy solid. $^1$H NMR (400 MHz, DMSO-d$_6$) δ (ppm): 8.71 (s, 1H), 8.58 (d, J=1.6 Hz, 1H). 8.51 (d, J=5.5 Hz, 1H), 8.31 (s, 1H), 8.23 (d, J=8.2 Hz, 1H), 7.91 (dd, J=8.2, 2.2 Hz, 1H), 7.73 (dd, J=13.6, 2.4 Hz, 1H), 7.38 (t, J=9.0 Hz, 1H), 7.23-7.17 (m, 1H), 6.64 (d, J=5.5 Hz, 1H), 6.57 (bd, J=2.7 Hz, 1H), 3.84 (d, J=14.5 Hz, 1H), 3.78 (d, J=14.5 Hz, 1H), 3.27 (dd, J=9.4, 6.3 Hz, 1H), 3.24 (s, 3H), 3.19 (dd, J=9.2, 5.5 Hz, 1H), 2.81-2.71 (m, 1H), 2.59-2.51 (m, 1H), 2.36-2.10 (m, 1H), 0.98 (d, J=6.3 Hz, 3H), 0.69-0.62 (m, 2H), 0.46-0.40 (m, 2H). MS (m/z): 522.4 (M+H).

Step 2. (S)—N-((6-(7-(4-(3-cyclopropylureido)-2-fluorophenoxy)thieno[3,2-b]pyridin-2-yl)pyridin-3-yl)methyl)-N-(1-methoxypropan-2-yl)acetamide (335)

A suspension of urea 334 (66 mg, 0.127 mmol) in acetic anhydride (2 ml) was stirred at rt for 2 days. The reaction mixture was quenched by addition of methanol and water, and partitioned with AcOEt. After separation, the organic layer was collected, washed with water, 1N NaOH (×4), water and brine, dried over anhydrous magnesium sulfate, filtered and concentrated. The crude solid was purified by flash column chromatography on silica gel (eluent 2% of ammonium hydroxyde in MeOH/DCM: 05/90 to 10/90) to afford the title compound 335 (46 mg, 0.08 mmol, 64% yield) as an off-white fluffy solid. $^1$H NMR (400 MHz, DMSO-d$_6$) δ (ppm): mixture of rotamers, 8.70 (s, 1H), 8.58-8.48 (m, 2H), 8.34 and 8.30 (2s, 1H), 8.27 and 8.19 (2d, J=8.3 Hz, 1H), 7.85-7.69 (m, 2H), 7.38 (t, J=9.0 Hz, 1H), 7.20 (bd, J=9.0 Hz, 1H), 6.67-6.54 (m, 2H), 4.74-4.16 (m, 3H), 3.41-3.22 (m, 2H), 3.15 and 3.13 (2s, 3H), 2.59-2.52 (m, 1H), 2.16 and 1.96 (2s, 3H), 1.09 and 1.04 (2d, J=6.9 Hz, 3H), 0.72-0.58 (m, 2H), 0.50-0.36 (m, 2H). MS (m/z): 564.4 (M+H).

Scheme 23

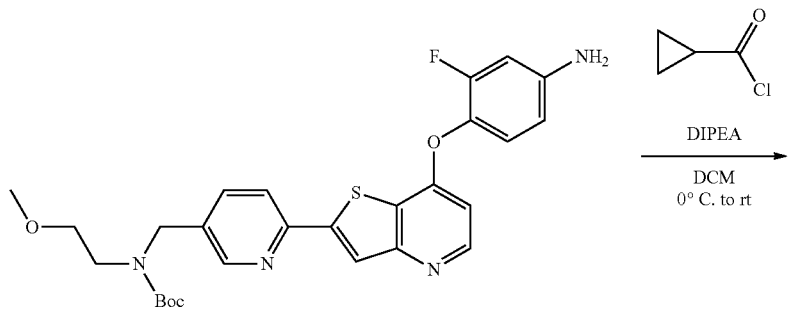

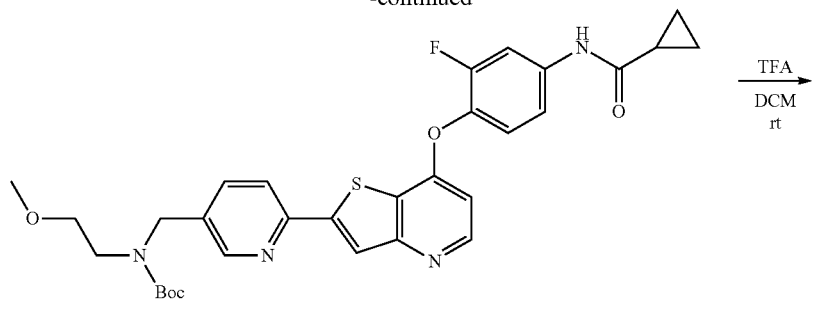

336

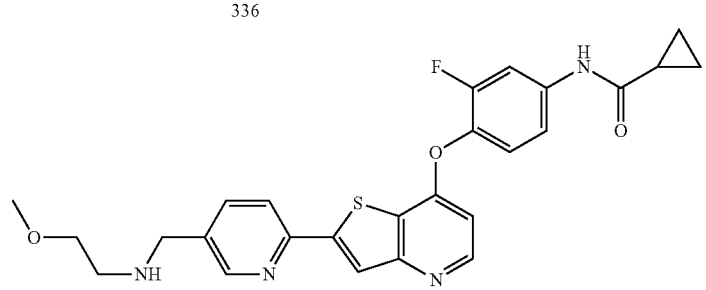

337: Example 210

Example 210

N-(3-Fluoro-4-(2-(5-((2-methoxyethylamino)methyl)pyridin-2-yl)thieno[3,2-b]pyridin-7-yloxy)phenyl)cyclopropanecarboxamide (337)

Step 1. tert-Butyl(6-(7-(4-(cyclopropanecarboxamido)-2-fluorophenoxy)thieno[3,2-b]pyridin-2-yl)pyridin-3-yl)methyl(2-methoxyethyl)carbamate (336)

To a solution of aniline 126 (200 mg, 0.36 mmol) in DCM (10 mL) under nitrogen at 0° C. were added DIPEA (127 µl, 0.72 mmol) and cyclopropylcarbonyl chloride (50 □l, 0.54 mmol). The reaction mixture was allowed to warm-up to room temperature slowly and stirred overnight at room temperature. The reaction mixture was diluted in AcOEt, and successively washed with a saturated aqueous solution of ammonium chloride (×4), 1N NaOH (×2), water and brine, dried over anhydrous magnesium sulfate, filtered, and concentrated. The crude residue was coprecipitated in a minimum of AcOEt in hexanes. The solid was collected by filtration, rinsed with hexanes, air-dried and dried under high vacuum to afford the title compound A (quantitative yield) as a pale brown solid. MS (m/z): 593.4 (M+H).

Step 2. N-(3-Fluoro-4-(2-(5-((2-methoxyethylamino)methyl)pyridin-2-yl)thieno[3,2-b]pyridin-7-yloxy)phenyl)cyclopropanecarboxamide (337)

To a solution of amide 336 (215 mg, crude mixture) in DCM (10 mL) was added TFA (2 ml). The reaction mixture was stirred at room temperature for 2 h., concentrated, partitioned between water and AcOEt, and basified with 1N NaOH solution. After separation of layers, the organic layer was collected, washed with 1N NaOH (×2), water and brine, dried over anhydrous magnesium sulfate, filtered and concentrated. The residue was purified by flash column chromatography on silica gel (eluent 2% of ammonium hydroxyde in MeOH/DCM: 05/95 to 15/95) to afford the title compound 336 (87 mg, 0.177 mmol, 48% yield) as a salmon sticky solid. $^1$H NMR (400 MHz, DMSO-$d_6$) δ (ppm): 10.57 (s, 1H), 8.57 (d, J=1.6 Hz, 1H), 8.52 (d, J=5.5 Hz, 1H), 8.32 (s, 1H), 8.23 (d, J=8.0 Hz, 1H), 7.93-7.83 (m, 2H), 7.47 (t, J=8.9 Hz, 1H), 7.41 (dd, J=8.9, 2.0, 1H), 6.66 (d, J=5.3 Hz, 1H), 3.78 (s, 2H), 3.41 (t, J=5.6 Hz, 2H), 3.24 (s, 3H), 2.66 (t, J=5.7 Hz, 2H), 1.79 (quint., J=6.2 Hz, 1H), 0.90-0.80 (m, 4H), one NH is missing. MS (m/z): 493.4 (M+H).

Scheme 24

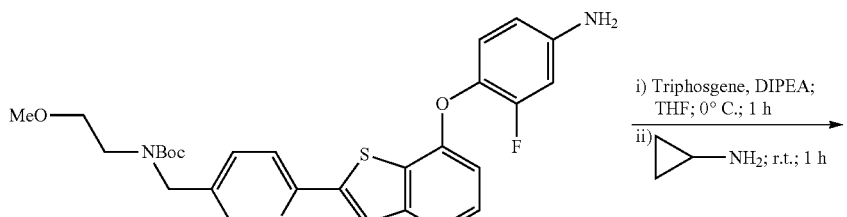

126

-continued
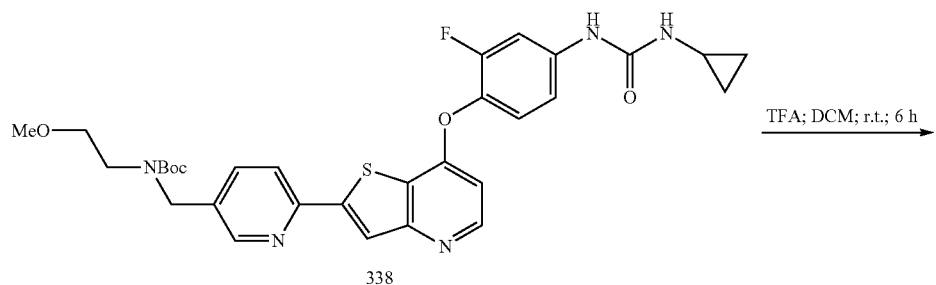
338
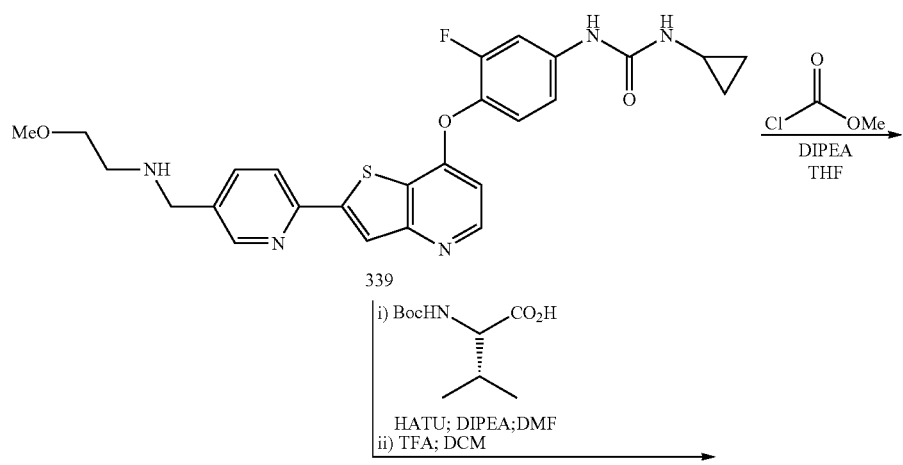
339
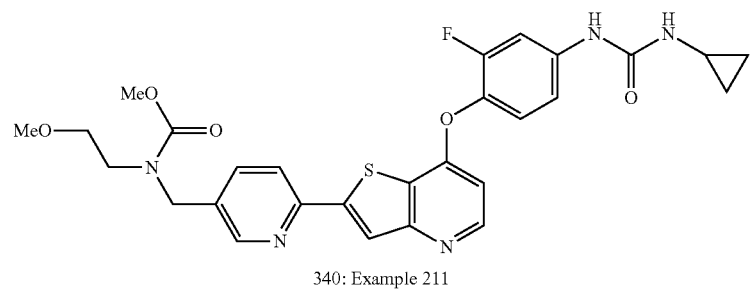
340: Example 211
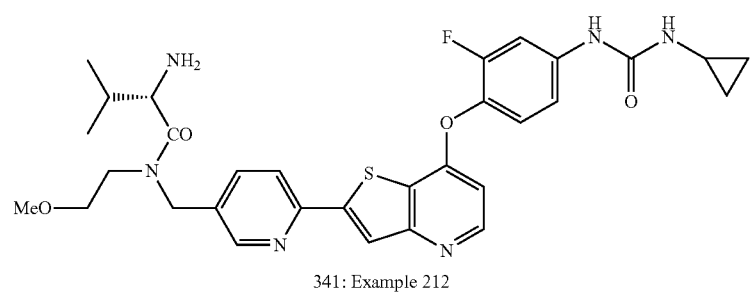
341: Example 212

Examples 340 and 341

Methyl(6-(7-(4-(3-cyclopropylureido)-2-fluorophenoxy)thieno[3,2-b]pyridin-2-yl)pyridin-3-yl)methyl (2-methoxyethyl)carbamate (340) and (R)-2-amino-N-((6-(7-(4-(3-cyclopropylureido)-2-fluorophenoxy)thieno[3,2-b]pyridin-2-yl)pyridin-3-yl)methyl)-N-(2-methoxyethyl)-3-methylbutanamide (341)

Step 1: tert-Butyl(6-(7-(4-(3-cyclopropylureido)-2-fluorophenoxy)thieno[3,2-b]pyridin-2-yl)pyridin-3-yl)methyl(2-methoxyethyl)carbamate (338)

To amine 126 (0.24 g, 0.46 mmol) in tetrahydrofuran (60 mL) at 0° C. was added triphosgene (0.054 g, 0.18 mmol) and the resulting solution was stirred for 1 h at 0° C. DIPEA (0.40 mL, 0.30 g, 2.3 mmol) and cyclopropylamine (0.26 g, 4.6 mmol) were sequentially added and the mixture was warmed to room temperature and stirred for 3 h, then concentrated under reduced pressure. The residue was partitioned between dichloromethane and water, the organic phase was collected, washed with sat. $NH_4Cl_{(aq)}$ and brine, dried over $MgSO_4$, filtered and concentrated. The residue was purified by flash chromatography on silica gel (ethyl acetate to 5% methanol/ethyl acetate), yielding 338 (0.19 g, 67% yield). MS (m/z): 608.4 (M+H).

Step 2: 1-cyclopropyl-3-(3-fluoro-4-(2-(5-((2-methoxyethylamino)methyl)pyridin-2-yl)thieno[3,2-b]pyridin-7-yloxy)phenyl)urea (339)

To 338 (0.19 g, 0.31 mmol) in dichloromethane (40 mL) was added TFA (3 mL). The solution was stirred for 6 h, then concentrated. The residue was partitioned between 98:2 dichloromethane/methanol mixture and 1M NaOH(aq), washed with brine, dried over $MgSO_4$, filtered and concentrated. The resulting oil was triturated with diethyl ether and ethyl acetate providing 339 (0.13 g, 82% yield). $^1H$ NMR (400 MHz, DMSO-$d_6$) δ (ppm): $^1H$: 8.80 (s, 1H); 8.57 (s, 1H); 8.51 (d, J=5.5, 1H); 8.31 (s, 1H); 8.23 (d, J=8.0, 1H); 7.89 (dd, J=8.0, 1.5, 1H); 7.73 (dd, J=13.5, 2.2, 1H); 7.38 (t, J=9.0, 1H); 7.20 (d, J=8.2, 1H); 6.66-6.62 (m, 2H); 3.78 (s, 2H); 3.41 (t, J=5.7, 2H); 3.24 (s, 3H); 2.65 (d, J=5.7, 2H); 2.57-2.51 (m, 1H); 0.66-0.62 (m, 2H); 0.44-0.41 (m, 2H). MS (m/z): 508.3 (M+H).

Step 3. Methyl(6-(7-(4-(3-cyclopropylureido)-2-fluorophenoxy)thieno[3,2-b]pyridin-2-yl)pyridin-3-yl)methyl(2-methoxyethyl)carbamate (340)

To a solution of compound 339 (220 mg, 0.433 mmol) and methyl chloroformate (50.2 μl, 0.65 mmol) in THF (4 ml) was added DIPEA (227 μl, 1.30 mmol) and the mixture was stirred at room temperature for 18 h. The solvent was removed under reduced pressure, the residue was triturated with MeOH and the solid suspension was collected by filtration and purified via Biotage (linear gradient 0-20%, methanol/dichloromethane; Snap 25 g column) to afford compound 340 (123.1 mg, 0.218 mmol, 50.2% yield) as a beige solid. $^1H$ NMR (400 MHz, DMSO-$d_6$) δ (ppm): 8.70 (s, 1H), 8.56-8.50 (m, 2H), 8.33 (s, 1H), 8.25 (d, J=8.0 Hz, 1H), 7.84-7.77 (m, 1H), 7.73 (dd, J=13.6, 2.4 Hz, 1H), 7.38 (t, J=9.2 Hz, 1H), 7.20 (dd, J=8.8, 1.2 Hz, 1H), 6.65 (d, J=5.6 Hz, 1H), 6.56 (d, J=2.8 Hz, 1H), 4.54 (s, 2H), 3.64 (s, 2H), 3.44 (s, 3H), 3.22 (s, 2H), 2.59-2.51 (m, 1H), 0.69-0.62 (m, 2H), 0.46-0.40 (m, 2H). MS (m/z): 566.1 (M+H).

Step 4: (R)-2-amino-N-((6-(7-(4-(3-cyclopropylureido)-2-fluorophenoxy)thieno[3,2-b]pyridin-2-yl)pyridin-3-yl)methyl)-N-(2-methoxyethyl)-3-methylbutanamide (341)

To a solution of 339 (48 mg, 0.095 mmol), N-Boc-valine (41 mg, 0.19 mmol), and DIPEA (0.083 mL, 0.47 mmol) in DMF (20 mL) was added HATU (90 mg, 0.236 mmol). The resulting solution was stirred at r.t. for 3 h. The reaction mixture was partitioned between ethyl acetate and water, washed with 1M HCl and brine, dried ($MgSO_4$), filtered and concentrated to yield the crude, BOC-protected product. This material was dissolved in dichloromethane (75 mL) and trifluoroacetic acid (3 mL), and stirred at r.t. for 3 h. The mixture was then concentrated and the residue was purified by Gilson reverse phase HPLC (35-95% MeOH/$H_2O$, Aquasil $C_{18}$, 30 min) and lyophilized. The residue (containing some formic acid from the HPLC) was partitioned between dichloromethane and 1M NaOH. The organic phase was dried ($MgSO_4$), filtered and concentrated to give 341 (18 mg, 50% yield) as a 7:3 mixture of rotamers by $^1H$ NMR. $^1H$ NMR (DMSO-$d_6$) δ(ppm) $^1H$: 8.73 (s, 1H); 8.57-8.51 (m, 2H); 8.36 (s, 0.3H); 8.32 (s, 0.7H); 8.29-8.24 (m, 1H); 7.84-7.71 (m, 2H); 7.38 (t, J=8.8, 1H); 7.21 (d, J=8.3, 1H); 6.66-6.64 (m, 1H); 6.59 (s, 1H); 4.90 (d, J=17.6, 0.3H); 4.73 (d, J=15.6, 0.7H); 4.64 (d, J=17.1, 0.3H); 4.53 (d, J=15.6, 0.7H); 3.73-3.39 (m, 5H); 3.25 (s, 2.2H); 3.22 (s, 1.1H); 2.58-2.52 (m, 1H); 1.80-1.70 (m, 1H); 0.89-0.84 (m, 6H); 0.68-0.64 (m, 2H); 0.45-0.41 (m, 2H). LRMS: (M+H) 607.5.

Scheme 25

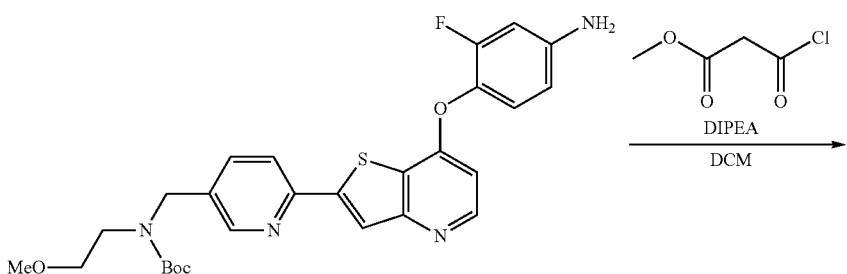

126

-continued
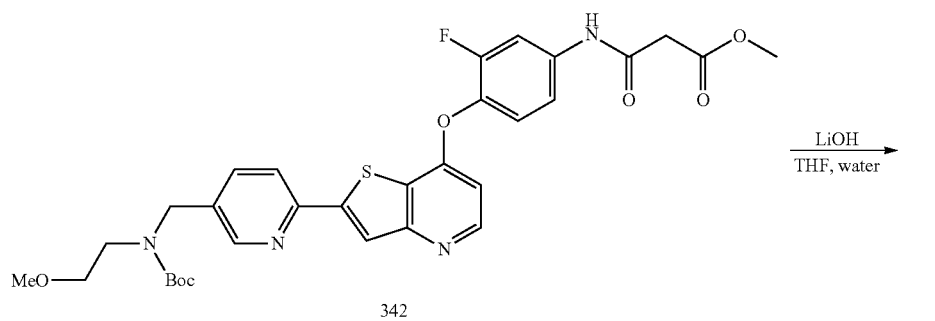
342
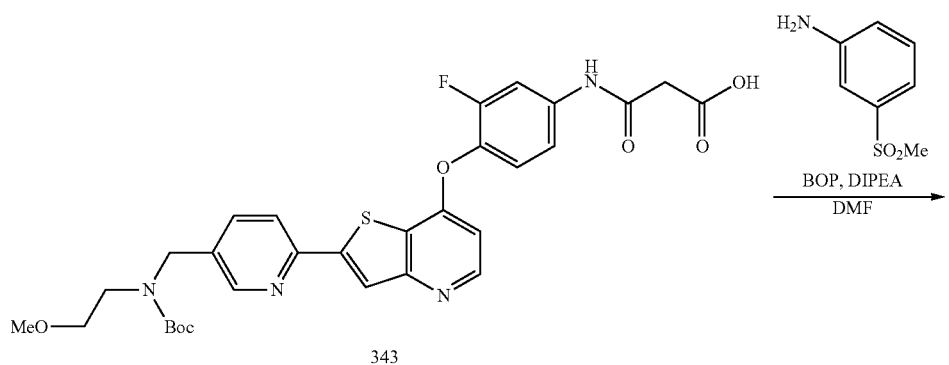
343
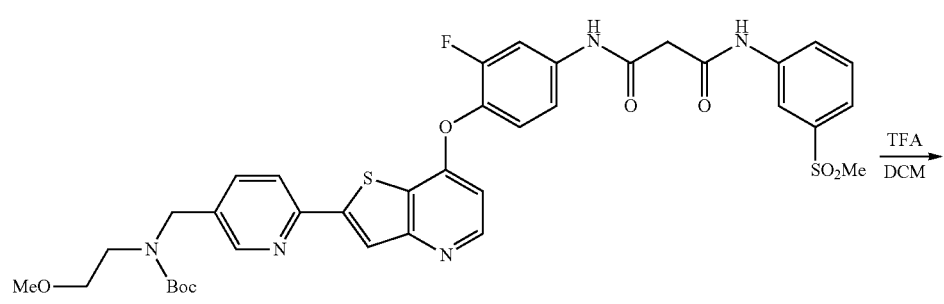
344
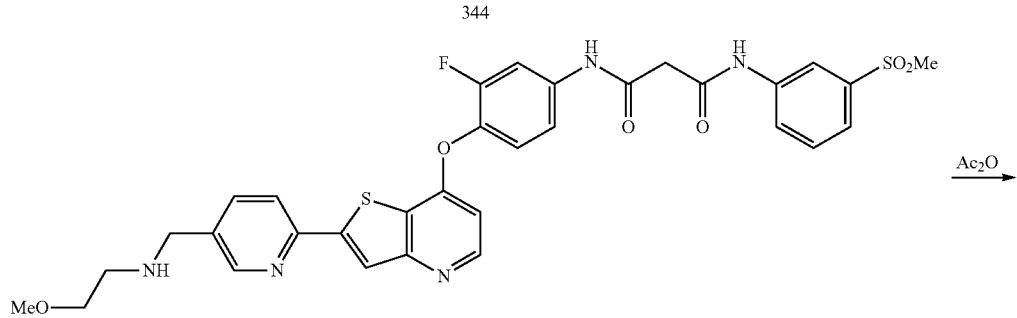
345: Example 213
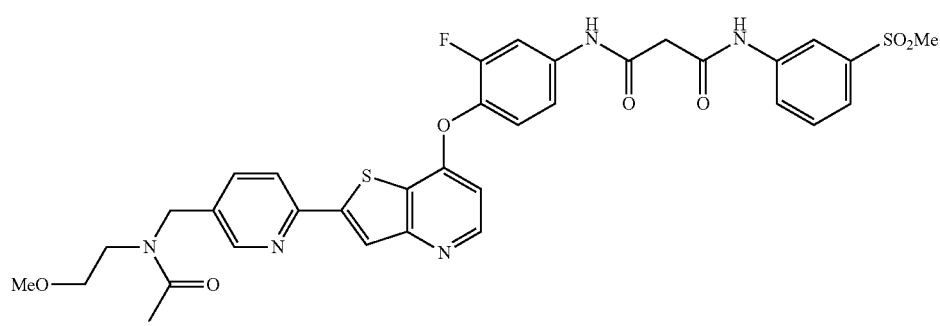
346: Example 214

Examples 213 and 214

N¹-(3-Fluoro-4-(2-(5-((2-methoxyethylamino)methyl)pyridin-2-yl)thieno[3,2-b]pyridin-7-yloxy)phenyl)-N³-(3-(methylsulfonyl)phenyl)malonamide (345) and N¹-(3-fluoro-4-(2-(5-((N-(2-methoxyethyl)acetamido)methyl)pyridin-2-yl)thieno[3,2-b]pyridin-7-yloxy)phenyl)-N³-(3-(methylsulfonyl)phenyl)malonamide (346)

Step 1: methyl 3-(4-(2-(5-(((tert-butoxycarbonyl(2-methoxyethyl)amino)methyl)pyridin-2-yl)thieno[3,2-b]pyridin-7-yloxy)-3-fluorophenylamino)-3-oxopropanoate (342)

To a solution of compound 126 (480 mg, 0.915 mmol) and DIPEA (479 µl, 2.74 mmol) in DCM (9 ml) at room temperature was added methyl malonyl chloride (196 µl, 1.83 mmol). The mixture was stirred for 18 h. A saturated aqueous solution of ammonium chloride was added and the aqueous phase extracted twice with DCM. The combined organic layers were dried over anhydrous sodium sulfate and concentrated. The residue was purified via Biotage (linear gradient 0-20%, methanol/dichloromethane; Snap 50 g column) to afford compound 342 (540 mg, 0.86 mmol, 94% yield) as a yellow oil. MS (m/z): 625.5 (M+H).

Step 2. 3-(4-(2-(5-(((tert-butoxycarbonyl(2-methoxyethyl)amino)methyl)pyridin-2-yl)thieno[3,2-b]pyridin-7-yloxy)-3-fluorophenylamino)-3-oxopropanoic acid (343)

To a solution of compound 342 (540 mg, 0.864 mmol) in THF (12 ml) and water (6 ml) was added LiOH monohydrate (363 mg, 8.64 mmol). The mixture was stirred 48 h at room temperature and THF was removed under reduced pressure. The aqueous solution was diluted with water (10 ml) and acidified to pH 4 using 1N HCl. The suspension was filtered and the precipitate was dried under high vacuum to afford compound 343 (485 mg, 0.79 mmol, 92% yield) as a beige solid. MS (m/z): 611.5 (M+H).

Steps 3 and 4. N¹-(3-fluoro-4-(2-(5-((2-methoxyethylamino)methyl)pyridin-2-yl)thieno[3,2-b]pyridin-7-yloxy)phenyl)-N³-(3-(methylsulfonyl)phenyl)malonamide (345)

To a solution of compound 343 (120 mg, 0.197 mmol), 3-methylsulfonylaniline hydrochloride (82 mg, 0.393 mmol) and DIPEA (172 µl, 0.983 mmol) in DMF (4 ml) was added BOP reagent (261 mg, 0.59 mmol) and the mixture was stirred at room temperature for 18 h. A saturated aqueous solution of ammonium chloride was added and the aqueous phase extracted twice with ethyl acetate. The combined organic extracts were washed with brine, dried over anhydrous sodium sulfate and the solvent was removed under reduced pressure. The residue was purified via Biotage (linear gradient 0-20%, methanol/dichloromethane; Snap 25 g column) to afford compound 344 as yellow solid (not characterized) which was dissolved in DCM (10 ml) and treated with TFA (4.5 mL, 59 mmol). The mixture was stirred for 18 h at room temperature. The solvent was removed under reduced pressure, the residue was diluted with ethyl acetate and the organic layer was extracted with 1N NaOH. The aqueous phase was extracted 3 times with ethyl acetate and the combined organic layers were concentrated. The residue was purified via Biotage (linear gradient 0-30%, methanol/dichloromethane; Snap 50 g column) to afford compound 345 (39 mg, 0.059 mmol, 29.9% yield) as a beige solid. ¹H NMR (400 MHz, DMSO-$d_6$) δ (ppm): 10.65 (s, 1H), 10.61 (s, 1H), 8.57 (d, J=1.6 Hz, 1H), 8.52 (d, J=5.2 Hz, 1H), 8.33 (s, 1H), 8.28 (s, 1H), 8.24 (d, J=8.0 Hz, 1H), 7.92-7.85 (m, 3H), 7.66-7.60 (m, 2H), 7.51 (t, J=8.8 Hz, 1H), 7.45 (dd, J=9.2, 1.6 Hz, 1H), 6.68 (dd, J=5.2, 0.8 Hz, 1H), 3.79 (s, 2H), 3.57 (s, 2H), 3.41 (t, J=5.6 Hz, 2H), 3.24 (s, 3H), 3.21 (s, 3H), 2.66 (t, J=5.6 Hz, 2H). MS (m/z): 664.5 (M+H).

Step 5. N¹-(3-fluoro-4-(2-(5-((N-(2-methoxyethyl)acetamido)methyl)pyridin-2-yl)thieno[3,2-b]pyridin-7-yloxy)phenyl)-N³-(3-(methylsulfonyl)phenyl)malonamide (346)

A solution of compound 345 (18.5 mg, 0.028 mmol) in acetic anhydride (1.31 ml, 13.9 mmol) was stirred at room temperature for 60 h. The solvent was removed under reduced pressure and the residue was triturated with water for 3 h. The solid suspension was filtered, the precipitate was rinsed with water and dried under high vacuum to afford compound 346 (6.4 mg, 9.07 µmol, 32.5%) as a beige solid. ¹H NMR (400 MHz, DMSO-$d_6$) δ (ppm): mixture of rotamers, 10.64 (s, 1H), 10.60 (s, 1H), 8.55-8.49 (m, 2H), 8.38-8.21 (m, 3H), 7.91-7.86 (m, 2H), 7.78 (td, J=8.8, 2.0 Hz, 1H), 7.66-7.60 (m, 2H), 7.51 (t, J=8.8 Hz, 1H), 7.44 (dd, J=9.2, 1.6 Hz, 1H), 6.71-6.67 (m, 1H), 4.71 and 4.59 (2s, 2H), 3.58-3.23 (m, 14H), 3.21 (s, 3H), 2.13 and 2.05 (2s, 3H). MS (m/z): 706.5 (M+H).

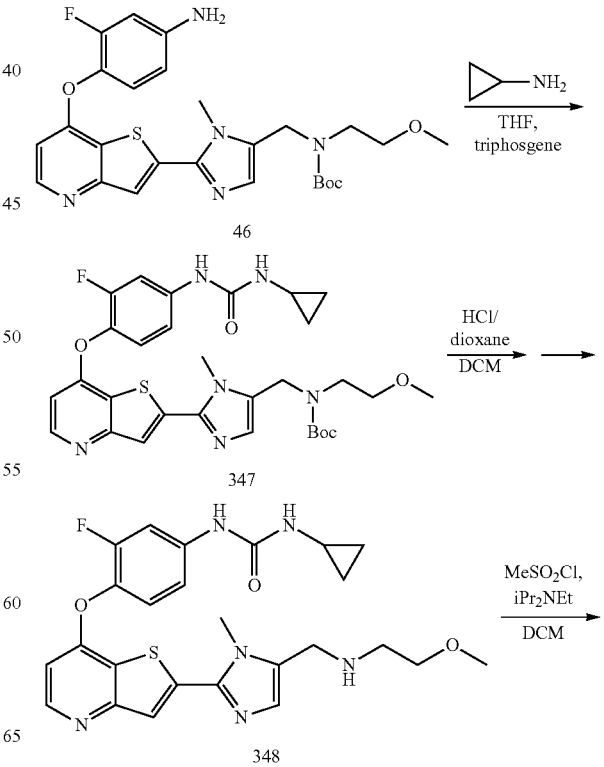

Scheme 26

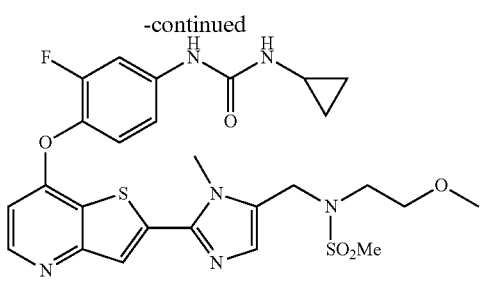

349: Example 215

Example 215

N-((2-(7-(4-(3-Cyclopropylureido)-2-fluorophenoxy)thieno[3,2-b]pyridin-2-yl)-1-methyl-1H-imidazol-5-yl)methyl)-N-(2-methoxyethyl)methanesulfonamide (349)

Step 1: tert-Butyl(2-(7-(4-(3-cyclopropylureido)-2-fluorophenoxy)thieno[3,2-b]pyridin-2-yl)-1-methyl-1H-imidazol-5-yl)methyl(2-methoxyethyl)carbamate (347)

To a solution of the aniline 46 (400 mg, 0.758 mmol) was added triphosgene (1125 mg, 5 eq, 3.79 mmol) and iPr$_2$NEt (490 mg, 5 eq, 3.79 mmol) and the reaction mixture was stirred at RT for an hour. Cyclopropylamine (6103 mg, 141 eq, 107 mmol) was added and the reaction mixture was stirred at RT overnight. The mixture was concentrated then diluted with DCM and washed with water. The organic phase was collected, dried over Na$_2$SO$_4$, filtered and evaporated. The residue was purified by column chromatography (eluent 20% MeOH in EtOAc) to afford the desired compound 347 as a yellow oil (426 mg, 92% yield). MS (m/z)=611.4 (M+H).

Step 2: 1-Cyclopropyl-3-(3-fluoro-4-(2-(54(2-methoxyethylamino)methyl)-1-methyl-1H-imidazol-2-yl)thieno[3,2-b]pyridin-7-yloxy)phenyl)urea (348)

To a solution of the 347 (426 mg, 0.698 mmol) in DCM (10 ml) was added HCl in dioxane (0.7 ml, 4.01 eq, 2.80 mmol, 4M in dioxane) and the reaction mixture was stirred at RT for 3 hours. The mixture wad diluted with water and solid NaHCO$_3$ was added. The reaction mixture was extracted well with EtOAc then the organic phase was collected, dried over Na$_2$SO$_4$, filtered and concentrated. The residue was purified by column chromatography (eluent 25% MeOH in EtOAc to 50% MeOH in EtOAc) to afford the desired compound 348 as a yellow powder (211 mg, 59% yield). MS (m/z)=511.4 (M+H).

Step 3: N-((2-(7-(4-(3-Cyclopropylureido)-2-fluorophenoxy)thieno[3,2-b]pyridin-2-yl)-1-methyl-1H-imidazol-5-yl)methyl)-N-(2-methoxyethyl)methanesulfonamide (349)

To a suspension of the amine 348 (61 mg, 0.119 mmol) in DCM (5 ml) was added methanesulfonyl chloride (20.53 mg, 1.5 eq, 0.179 mmol) and iPr$_2$NEt (46.3 mg, 3 eq, 0.358 mmol) and the reaction mixture was stirred at RT for 3 hours. The mixture was diluted with EtOAc then washed with saturated NH$_4$Cl solution, saturated NaHCO$_3$ solution and brine. The organic phase was collected, dried over Na$_2$SO$_4$, filtered and concentrated. The residue was purified by column chroma-tography (eluent 25% MeOH in EtOAc) to afford the desired compound 349 as a pale yellow solid (34 mg, 48%). $^1$H NMR (d$_6$ DMSO) 8.27 (s, 1H), 8.10 (d, J=5.48 Hz, 1H), 7.53 (s, 1H), 7.25 (m, 1H), 6.95 (t, J=9.0 Hz, 1H), 6.76 (m, 1H), 6.71 (s, 1H), 6.24 (d, J=5.48 Hz, 1H), 6.14 (s, 1H), 4.06 (s, 2H), 3.49 (s, 3H), 2.72 (s, 3H), 2.63 (s, 3H), 2.12 (m, 3H), 0.23 (m, 2H), 0.00 (s, 2H).

Scheme 27

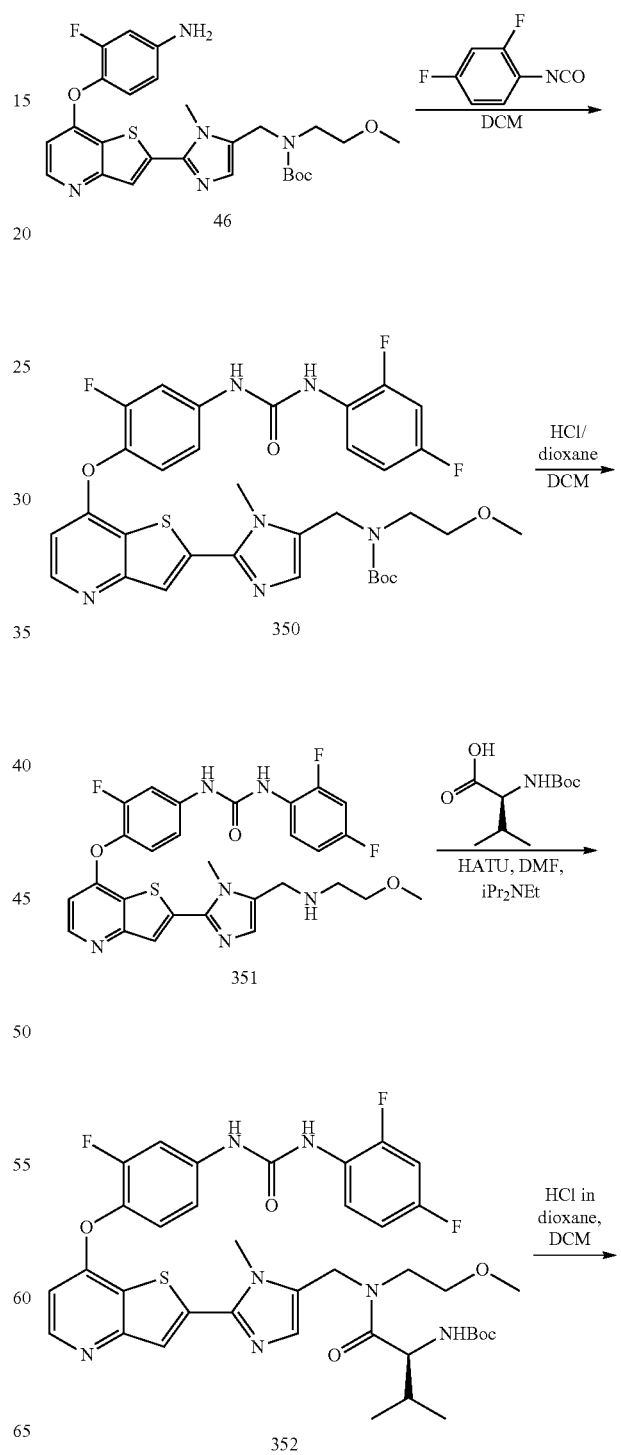

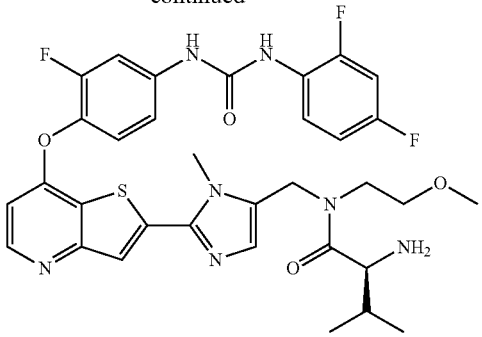

353: Example 216

Example 216

Step 1: tert-butyl(2-(7-(4-(3-(2,4-difluorophenyl)ureido)-2-fluorophenoxy)thieno[3,2-b]pyridin-2-yl)-1-methyl-1H-imidazol-5-yl)methyl(2-methoxyethyl)carbamate (350)

To a solution of aniline 46 (500 mg, 0.948 mmol) in DCM (10 ml) was added 2,4-difluoro-1-isocyanatobenzene (441 mg, 3 eq, 2.84 mmol) and the reaction mixture was stirred at RT for 24 hours. The mixture was concentrated and purified via column chromatography (eluent 10% MeOH in EtOAc) to afford 350 (600 mg, 93%) as a white solid. MS (m/z)=683.7 (M+H)

Step 2: 1-(2,4-difluorophenyl)-3-(3-fluoro-4-(2-(5-((2-methoxyethylamino)methyl)-1-methyl-1H-imidazol-2-yl)thieno[3,2-b]pyridin-7-yloxy)phenyl)urea (351)

To a solution of 350 (600 mg, 0.879 mmol) in DCM (15 ml) was added HCl in dioxane (2 ml, 7.17 eq, 8 mmol, 4M in dioxane) and the reaction mixture was stirred at RT for 3 hours. The mixture wad diluted with water and solid NaHCO$_3$ was added. The reaction mixture was extracted with EtOAc then the organic phase was collected, dried over Na$_2$SO$_4$, filtered and concentrated. Trituration of the residue with EtOAc afforded the desired compound 351 as an off-white solid (314 mg, 61% yield). $^1$H NMR (d$_6$-DMSO): 10.90 (s, 1H), 8.89 (s, 1H), 8.50 (d, J=5.48 Hz, 1H), 7.98 (m, 1H), 7.95 (s, 1H), 7.72 (m, 1H), 7.41 (m, 1H), 7.28-7.20 (m, 3H), 7.04 (m, 1H), 6.68 (d, J=5.28 Hz, 1H), 4.28 (s, 2H), 3.92 (s, 3H), 3.61 (m, 2H), 3.27 (s, 3H), 3.13 (m, 2H).

Step 3: (S)-tert-butyl 1-(((2-(7-(4-(3-(2,4-difluorophenyl)ureido)-2-fluorophenoxy)thieno[3,2-b]pyridin-2-yl)-1-methyl-1H-imidazol-5-yl)methyl)(2-methoxyethyl)amino)-3-methyl-1-oxobutan-2-ylcarbamate (352)

To a solution of the compound 351 (280 mg, 0.481 mmol) in DMF (10 ml) was added (S)-2-(tert-butoxycarbonylamino)-3-methylbutanoic acid (209 mg, 2 eq, 0.961 mmol), iPr$_2$NEt (0.252 ml, 3 eq, 0.1.442 mmol) and HATU (365 mg, 2 eq, 0.961 mmol) and the reaction mixture was stirred overnight. The reaction mixture was diluted with EtOAc and washed with water, saturated NAHCO$_3$ solution then brine. The organic phase was collected, dried over Na$_2$SO$_4$, filtered then concentrated. Purification of the residue by column chromatography (eluent 20% MeOH in EtOAc) afforded the desired compound 352 as an off-white solid (200 mg, 53% yield). MS (m/z)=782.7 (M+H).

Step 4: (S)-2-amino-N-((2-(7-(4-(3-(2,4-difluorophenyl)ureido)-2-fluorophenoxy)thieno[3,2-b]pyridin-2-yl)-1-methyl-1H-imidazol-5-yl)methyl)-N-(2-methoxyethyl)-3-methylbutanamide (353)

To a suspension of the compound 352 (200 mg, 0.256 mmol) in DCM (10 ml) was added HCl in dioxane (0.7 ml, 10.95 eq, 2.80 mmol, 4M in dioxane) and the reaction mixture was stirred at RT for 3 hours. The mixture wad diluted with water and solid NaHCO$_3$ was added. The reaction mixture was extracted with EtOAc then the organic phase was collected, dried over Na$_2$SO$_4$, filtered and concentrated. Purification of the residue by column chromatography (eluent 30% MeOH in EtOAc) afforded the desired compound 353 as pale yellow powder (155 mg, 89% yield). $^1$H NMR (d$_6$-DMSO) 9.36 (s, 1H), 8.60 (s, 1H), 8.49 (m, 1H), 8.01 (m, 1H), 7.87 (s, 1H), 7.71 (m, 1H), 7.41 (t, J=8.99 Hz, 1H), 7.31 (m, 1H), 7.20 (m, 1H), 7.02 (m, 1H), 6.98 (s, 1H), 6.65 (d, J=5.09 Hz, 1H), 4.83 (d, J=15.65 Hz, 1H), 4.48 (d, J=15.65 Hz, 1H), 3.81 (s, 1H), 3.80 (s, 2H), 3.40 (m, 1H), 3.39-3.295 (m, 6H), 1.71 (m, 2H), 0.81 (m, 6H).

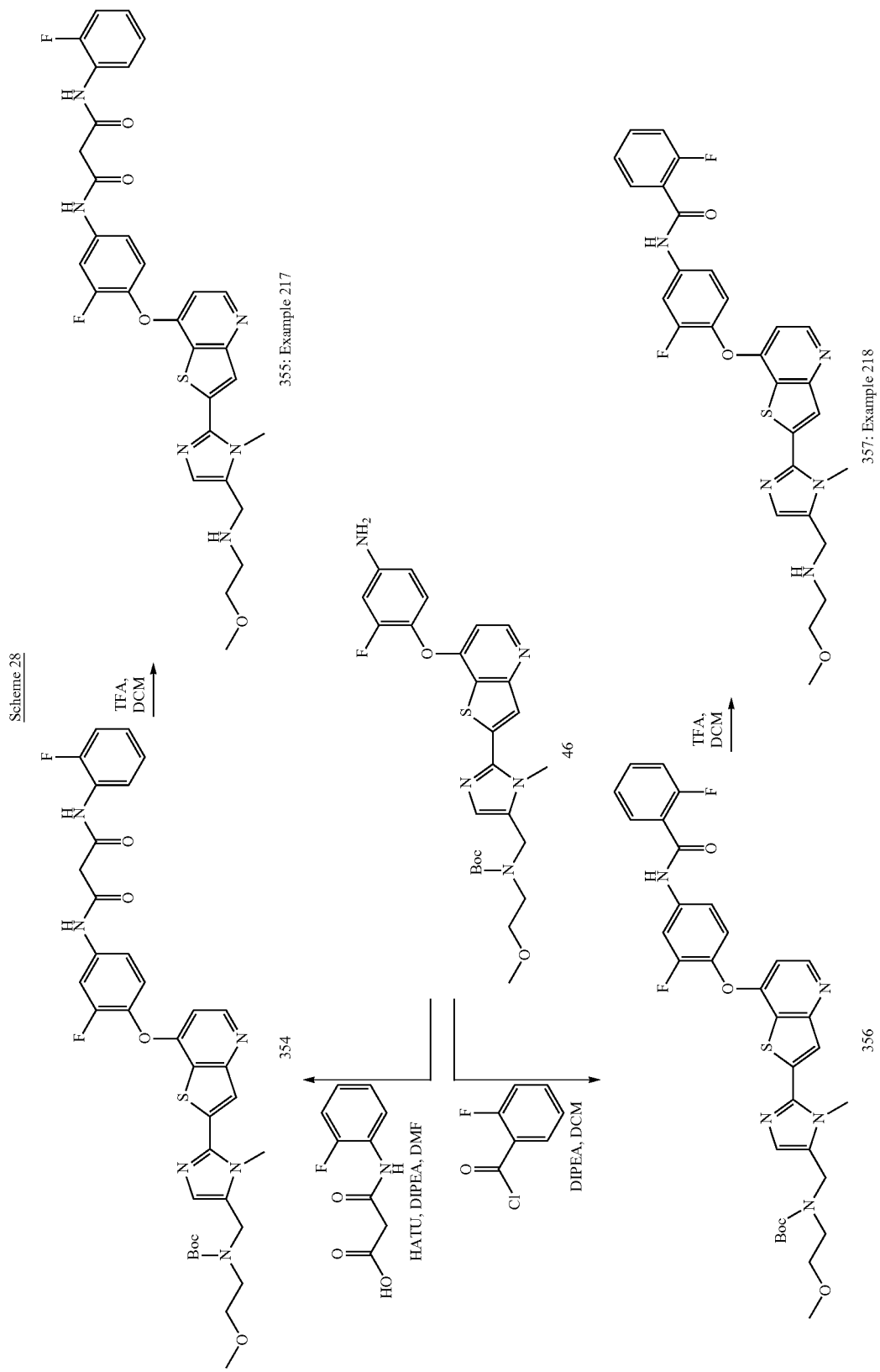

Example 217

N1-(3-Fluoro-4-(2-(5-((2-methoxyethylamino)methyl)-1-methyl-1H-imidazol-2-yl)thieno[3,2-b]pyridin-7-yloxy)phenyl)-N3-(2-fluorophenyl)malonamide (355)

Step 1. tert-Butyl(2-(7-(2-fluoro-4-(3-(2-fluorophenylamino)-3-oxopropanamido)phenoxy)thieno[3,2-b]pyridin-2-yl)-1-methyl-1H-imidazol-5-yl)methyl(2-methoxyethyl)carbamate (354)

To a solution of aniline 46 (300 mg, 0.569 mmol), acid 2 (224 mg, 1.137 mmol), and DIPEA (0.397 mL, 2.274 mmol) in DMF (15 mL) was added HATU (540 mg, 1.422 mmol). The reaction mixture was stirred for 16 h at rt, then partitioned between ethyl acetate and water; the organic layer was collected, washed with water, 1M NaOH, and brine, dried (Na$_2$SO$_4$) then filtered and concentrated. The residue was purified by Biotage(eluent 1-30% MeOH/EA, Silicycle 12 g column) to give 354 (230 mg, 0.325 mmol, 57.2% yield) as a beige solid. TLC: R$_f$=0.35 (eluent 10% MeOH/EtOAc),

Step 2. N1-(3-Fluoro-4-(2-(5-((2-methoxyethylamino)methyl)-1-methyl-1H-imidazol-2-yl)thieno[3,2-b]pyridin-7-yloxy)phenyl)-N3-(2-fluorophenyl)malonamide (355)

To a solution of 354 (230 mg, 0.325 mmol) in DCM (3 mL) was added TFA (0.5 mL). The reaction mixture was stirred at room temperature overnight then concentrated. The residue was partitioned between EtOAc and NaHCO$_3$ saturated solution. The organic layer was collected, dried and concentrated. The residue was purified via Biotage (0-50% MeOH/EA; 10 g SNAP column) to afford a reddish solid which was purified again by flash column chromatography (eluent MeOH/EA, 20-25%) to give a yellowish solid which was triturated with ether to afford the title compound 355 (80 mg, 0.132 mmol, 40.5% yield) as an off-white solid. HNMR (dmso) d(ppm) 1H: 10.53 (s, 1H), 10.01 (s, 1H), 8.47 (d, 1H, J=5.5 Hz), 7.95 (m, 1H), 7.85-7.81 (m, 2H), 7.46 (t, 1H, J=8.8 Hz), 7.39 (d, 1H, J=10.9 Hz), 7.15-7.09 (m, 2H), 6.91 (s, 1H), 6.65 (d, 1H, J=5.5 Hz), 3.81 (s, 3H), 3.72 (s, 2H), 3.58 (s, 2H), 3.35 (t, 2H, J=5.6 Hz), 3.20 (s, 3H), 2.64 (t, 2H, J=5.6 Hz). MS: 607.2 (MH)$^+$.

Example 218

2-fluoro-N-(3-fluoro-4-(2-(5-((2-methoxyethylamino)methyl)-1-methyl-1H-imidazol-2-yl)thieno[3,2-b]pyridin-7-yloxy)phenyl)benzamide (357)

Step 1. tert-Butyl(2-(7-(2-fluoro-4-(2-fluorobenzamido)phenoxy)thieno[3,2-b]pyridin-2-yl)-1-methyl-1H-imidazol-5-yl)methyl(2-methoxyethyl)carbamate (356)

To a solution of aniline 46 (300 mg, 0.569 mmol) in DCM (10 mL) at 0° C. was added DIPEA (0.199 mL, 1.137 mmol) and 2-fluorobenzoyl chloride (135 mg, 0.853 mmol) and the suspension was stirred overnight at room temperature. The reaction mixture was concentrated and the residue was partitioned between EtOAc and water. The organic layer was collected, dried and concentrated. The residue was purified using Biotage (eluent EtOAc, 25 g Silicycle HR column) to provide the title compound 356 (400 mg, 0.616 mmol, quantitative yield) as a white solid.

MS: 650(MH)+.

Step 2. 2-Fluoro-N-(3-fluoro-4-(2-(5-((2-methoxyethylamino)methyl)-1-methyl-1H-imidazol-2-yl)thieno[3,2-b]pyridin-7-yloxy)phenyl)benzamide (357)

A solution of of 356 (400 mg, 0.616 mmol) and TFA (0.047 mL, 0.616 mmol) in DCM (15 mL) was stirred overnight at room temperature then concentrated. The residue was partitioned between EtOAc and NaHCO$_3$ saturated solution. The product was found in both layers. The layers were combined and concentrated. The residue was extracted with MeOH and the inorganic solid was filtered off. The filtrate was concentrated and the residue was purified using Biotage (eluent MeOH/EtOAc, 10-50%, 25 g Silicycle column) to provide a solid that was triturated with a mixture EtOAc/ether to afford 358 (40 mg, 0.073 mmol, 11.82% yield) as a white solid. HNMR: (dmso) d(ppm) 1H:10.77 (s, 1H), 8.51 (d, 1H, J=5.5 Hz), 7.94-7.91 (m, 2H), 7.68-7.63 (m, 1H), 7.60-7.56 (m, 2H), 7.49 (t, 1H), J=8.8 Hz), 7.36-7.30 (m, 2H), 7.15 (s, 1H), 6.70 (d, 1H, J=5.5 Hz), 4.13 (s, 2H), 3.89 (s, 3H), 3.51 (t, 2H, J=5.3 Hz), 3.26 (s, 3H), 3.01 (m, 2H). MS: 550 (MH)$^+$ Scheme 29

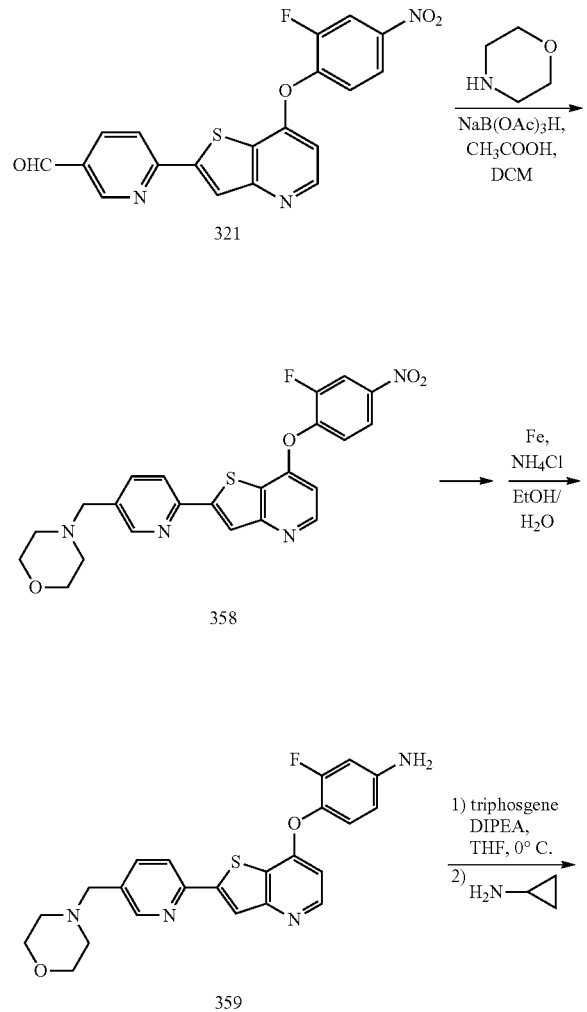

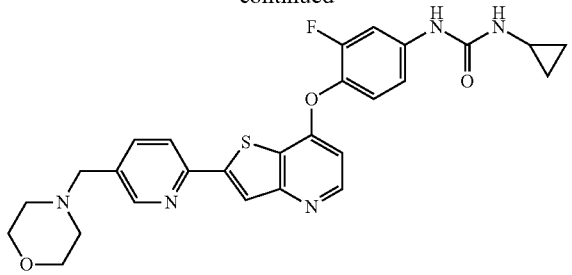

360: Example219

Example 219

1-Cyclopropyl-3-(3-fluoro-4-(2-(5-(morpholinomethyl)pyridin-2-yl)thieno[3,2-b]pyridin-7-yloxy)phenyl)urea (360)

Step 1. 4-((6-(7-(2-Fluoro-4-nitrophenoxy)thieno[3,2-b]pyridin-2-yl)pyridin-3-yl)methyl)morpholine (358)

To a suspension of carbaldehyde 321 (0.5 g, 1.265 mmol) in DCM (12.65 ml) were added morpholine (0.220 ml, 2.53 mmol) and acetic acid (0.145 ml, 2.53 mmol), and the mixture was stirred for 1 h at room temperature before sodium triacetoxy borohydride (0.804 g, 3.79 mmol) was added. Stirring was continued overnight. The mixture was then partitioned between DCM and 1N NaOH. The phases were separated; the organic layer was collected, dried over sodium sulfate and concentrated. The residue was purified via Biotage (linear gradient 0-20%, MeOH/EtOAc; 10 g SNAP column) to afford the title compound 358 (341 mg, 0.731 mmol, 57.8% yield) as a beige solid. MS: 467 (MH)+.

Step 2. 3-Fluoro-4-(2-(5-(morpholinomethyl)pyridin-2-yl)thieno[3,2-b]pyridin-7-yloxy)aniline (359)

A mixture of the nitro compound 358 (432 mg, 0.926 mmol), iron powder (440 mg, 7.87 mmol), and ammonium chloride (42.6 mg, 0.796 mmol) in a mixture of water (3.00 mL) and ethanol (6 mL) was heated to 80° C. for 30 min. The reaction mixture was then filtered while hot through a pad of Celite. The filtrate was concentrated and the residue was purified using Biotage (eluent 0-20% EtOAc/MeOH, 10 g SNAP column) to afford the amine 359 (136 mg, 0.312 mmol, 33.6% yield) as a white solid. MS: 437 (MH)+.

Step 3. 1-Cyclopropyl-3-(3-fluoro-4-(2-(5-(morpholinomethyl)pyridin-2-yl)thieno[3,2-d]pyridin-7-yloxy)phenyl)urea (360)

The solution of aniline 359 (136 mg, 0.312 mmol) and DIPEA (0.218 mL, 1.246 mmol) in THF (6 mL) was cooled to 0° C., and then triphosgene (46.2 mg, 0.156 mmol) was added and the reaction mixture was stirred for 1 h at 0° C. followed by an addition of cyclopropylamine (89 mg, 1.558 mmol). The reaction mixture was stirred at r.t. for an additional 3 hrs then concentrated, partitioned between water and ethyl acetate. A thick solid was formed which was isolated by suction filtration, rinsed with water and ethyl acetate, and dried in vacuo. This material was then purified using Gilson (eluent 20-95% MeOH/H$_2$O, 1 h) to give the title compound 360 (30 mg, 0.058 mmol, 18.53% yield) as a white solid. $^1$HNMR (DMSO-d$_6$) d(ppm) $^1$H:HNMR 9.16 (s, br, 1H), 8.16 (d, 1H, J=1.6 HZ), 8.11 (d, 1H, J=5.4 Hz), 7.91 (s, 1H), 7.83 (d, 1H, J=8.2 Hz), 7.46 (dd, 1H, J1=2.1 Hz, J2=8.2 Hz), 7.34 (dd, 1H, J1=2.6 Hz, J2=13.9 Hz), 6.97-7.45 (m, 2H), 6.84-6.81 (m, 1H), 6.23 (d, 1H, J=4.7 Hz), 3.18 (t, 4H), 3.14 (s, 2H), 2.15-2.12 (m, 1H), 1.98 (m, 4H), 0.23-0.19 (m, 2H), 0.02-0.005 (m, 2H). MS: 520.4 (MH)+.

Scheme 30

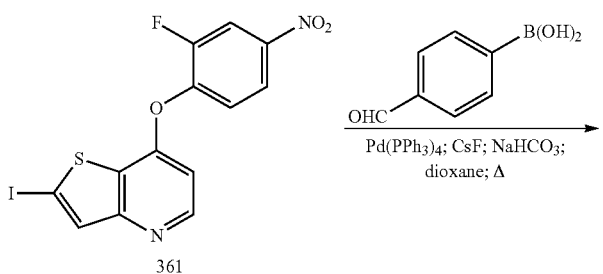

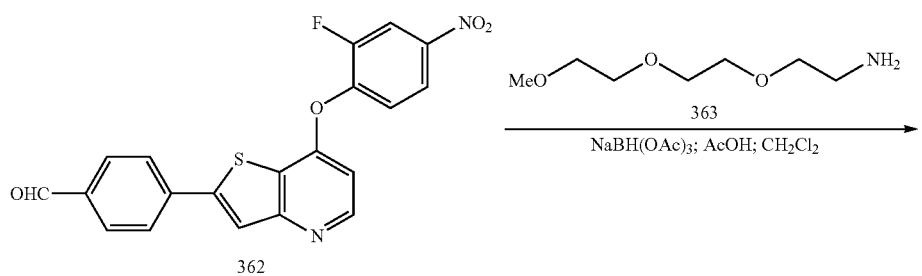

-continued
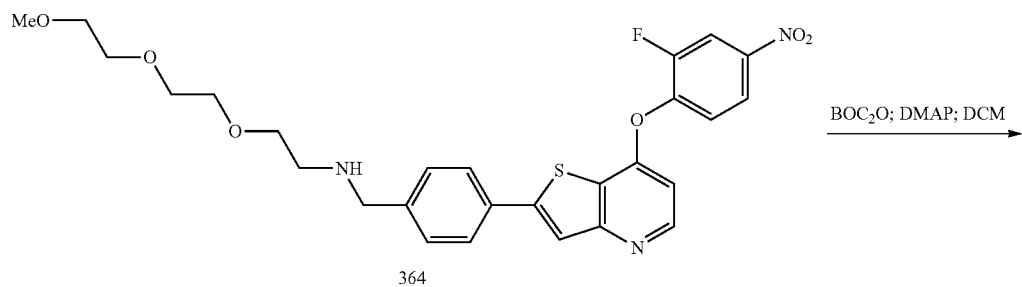
364
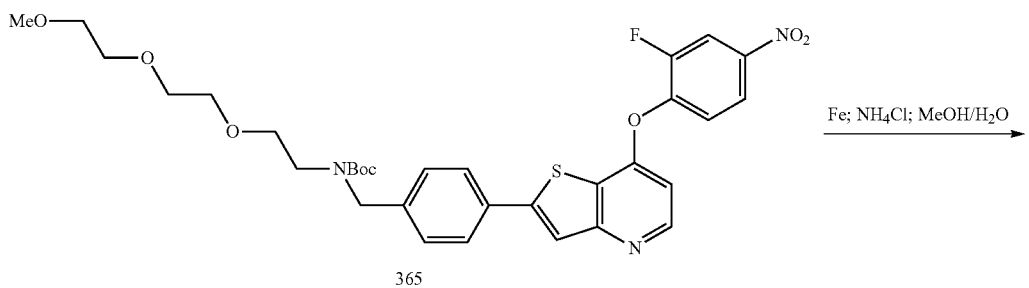
365
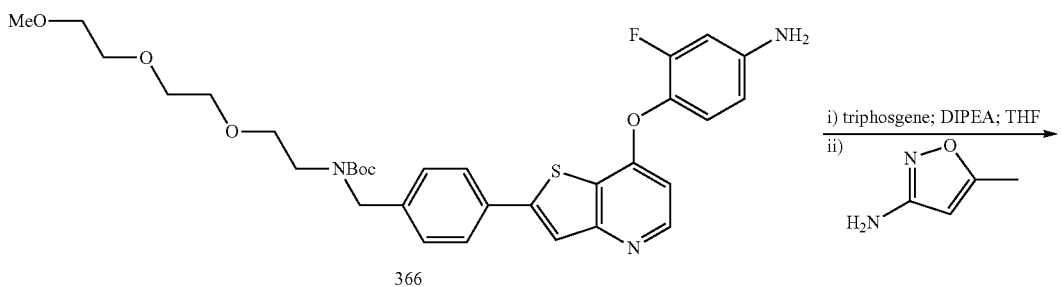
366
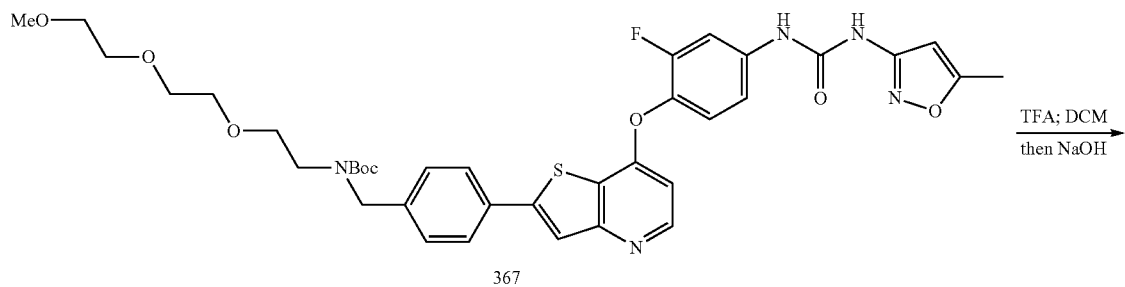
367
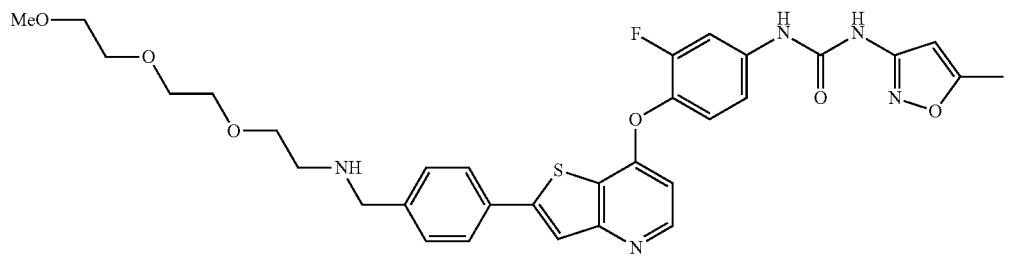
368: Example 220

Example 220

1-(4-(2-(4-5,8,11-Trioxa-2-azadodecylphenyl)thieno [3,2-b]pyridin-7-yloxy)-3-fluorophenyl)-3-(5-methylisoxazol-3-yl)urea (368)

Step 1: 4-(7-(2-fluoro-4-nitrophenoxy)thieno[3,2-b]pyridin-2-yl)benzaldehyde (362)

Iodothienopyridine 361 (US 2006/0287343) (2.10 g, 5.05 mmol), 4-formylphenylboronic acid (1.51 g, 10.1 mmol), and tetrakis(triphenylphosphine)palladium (0.29 g, 0.25 mmol) were dissolved in dry dioxane (80 mL). Cesium fluoride (0.92 g, 6.1 mmol) and sodium bicarbonate (2.12 g, 25.2 mmol) were dissolved in water (5 ml each) and added to the reaction mixture, which was degassed with a stream of $N_2$, then heated to reflux for 3 h, cooled, and concentrated. The residue was partitioned between ethyl acetate and water, resulting in a thick precipitate. This was isolated by suction filtration and rinsed with water and ethyl acetate to afford 362 (1.92 g, 96%). LRMS (M+H): 395.2

Step 2: N N-(4-(7-(2-fluoro-4-nitrophenoxy)thieno [3,2-b]pyridin-2-yl)benzyl)-2-(2-(2-methoxyethoxy) ethoxy)ethanamine (364)

A suspension of 362 (0.90 g, 2.3 mmol), amine 363 (0.93 g, 5.7 mmol) [amine 363 has been synthesized according to the procedures used for the synthesis of amines 322 (scheme 18) and 326 (scheme 20)] and acetic acid (0.26 ml, 4.6 mmol) in dichloromethane (50 ml) was stirred for 1 h at room temperature. Then sodium triacetoxyborohydride (1.45 g, 6.85 mmol) was added and the mixture was stirred at r.t. for 16 h. A further amount of sodium triacetoxyborohydride (1.5 g) was then added, and stirring continued for 2 h. The reaction mixture was partitioned between dichloromethane and 1N HCl. The organic phase was discarded. The aqueous phase was basified (pH=13) with 3M NaOH, and extracted with dichloromethane. The organic extract was dried over anhydrous sodium sulfate, filtered, and concentrated to yield 364 (0.72 g, 58%) as a yellow solid. LRMS (M+H): 542.4

Step 3: tert-butyl 4-(7-(2-fluoro-4-nitrophenoxy) thieno[3.2-b]pyridin-2-yl)benzyl(2-(2-(2-methoxyethoxy)ethoxy)ethyl)carbamate (365)

To a solution of 364 (0.72 g, 1.3 mmol) in dichloromethane (100 mL) at room temperature was added DMAP (0.041 g, 0.33 mmol) and $Boc_2O$ (0.58 g, 2.7 mmol). The reaction mixture was stirred at room temperature for 2 h then the mixture was washed sequentially with water, brine, dried over anhydrous magnesium sulfate, filtered, and concentrated. The residue was purified by silica gel chromatography (eluent EtOAc then 1% MeOH in EtOAc) to afford compound 365 (0.51 g, 60% yield). LRMS (M+H): 642.5

Step 4: tert-butyl 4-(7-(4-amino-2-fluorophenoxy) thieno[3,2-b]pyridin-2-ylbenzyl(2-(2-(2-methoxyethoxy)ethoxy)ethyl)carbamate (366)

To a solution of 365 (0.49 g, 0.76 mmol) in MeOH (100 mL) was added iron dust (0.43 g, 7.6 mmol) and ammonium chloride (0.12 g, 2.3 mmol) in water (5 mL). The resulting mixture was heated to reflux for 4 h, then cooled, filtered through a celite pad and concentrated. The residue was partitioned between dichloromethane and water; the organic phase was collected, washed with brine, dried over anhydrous magnesium sulfate, filtered, and concentrated. The residue was purified by silica gel chromatography (eluent 2% MeOH in EtOAc) to give 366 (0.41 g, 88% yield). LRMS (M+H): 612.6

Step 5: tert-butyl 4-(7-(2-fluoro-4-(3-(5-methylisoxazol-3-yl)ureido)phenoxy)thieno[3,2-b]pyridin-2-yl) benzyl(2-(2-(2-methoxyethoxy)ethoxy)ethyl)carbamate (367)

To a solution of 366 (0.15 g, 0.25 mmol) and DIPEA (0.11 mL, 0.080 g, 0.61 mmol) in tetrahydrofuran (50 mL) at 0° C. was added triphosgene (0.029 g, 0.098 mmol) and the resulting solution was stirred for 1 h at 0° C. 3-Amino-5-methylisoxazole (0.025 g, 0.25 mmol) was added and the mixture was warmed to room temperature and stirred for 3 h, then quenched with 1 mL of water and concentrated under reduced pressure. The residue was partitioned between ethyl acetate and water; the organic phase was collected, washed with brine, dried over $MgSO_4$, filtered and concentrated. The product was purified by silica gel chromatography (eluent 2% MeOH in EtOAc) to give 367 (0.074 g, 4% yield).

Step 7: 1-(4-(2-(4-5,8,11-trioxa-2-azadodecylphenyl) thieno[3,2-b]pyridin-7-yloxy)-3-fluorophenyl)-3-(5-methylisoxazol-3-yl)urea (368)

To a solution of 367 (0.074 g, 0.10 mmol) in dichloromethane (50 mL) was added trifluoroacetic acid (1.0 mL). The reaction mixture was stirred for 3 h at r.t. then concentrated and the residue was partitioned between dichloromethane and sat. $NaHCO_3$. The organic phase was collected, washed with brine, dried over $MgSO_4$, filtered and concentrated. The residue was purified by Gilson reverse phase HPLC (35-75% MeOH/$H_2O$, Aquasil $C_{18}$, 30 min) and lyophilized. The purified product (containing some formic acid from the HPLC) was partitioned between dichloromethane and 1M NaOH). The organic phase was collected, dried ($MgSO_4$), filtered and concentrated to give compound 368 (0.033 g, 0.052 mmol, 52% yield).
$^1$H NMR (DMSO-$d_6$) δ(ppm) $^1$H: 9.71 (s, 1H); 9.31 (s, 1H); 8.48 (d, J=5.5, 1H); 8.01 (s, 1H); 7.82-7.79 (m, 2H); 7.73 (dd, J=13.1, 2.5, 1H) 7.46-7.41 (m, 3H); 7.28-7.26 (m, 1H); 6.60 (d, J=5.5, 1H); 6.54 (d, J=0.8, 1H); 3.75 (s, 2H); 3.51-3.45 (m, 8H); 3.41-3.35 (m, 2H); 3.20 (s, 3H); 2.63 (t, J=5.7, 2H); 2.35 (d, J=0.6, 3H). LRMS (M+H): 636.5

Scheme 31

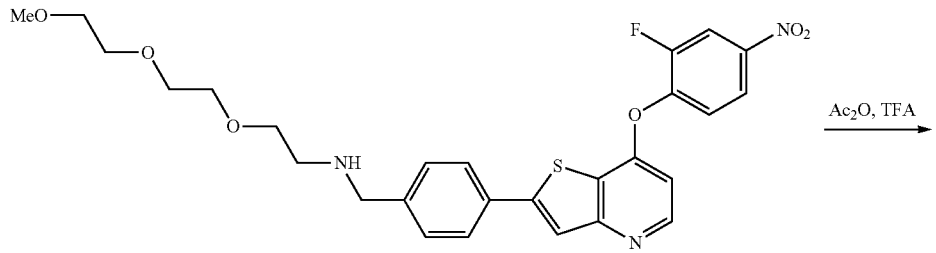

364

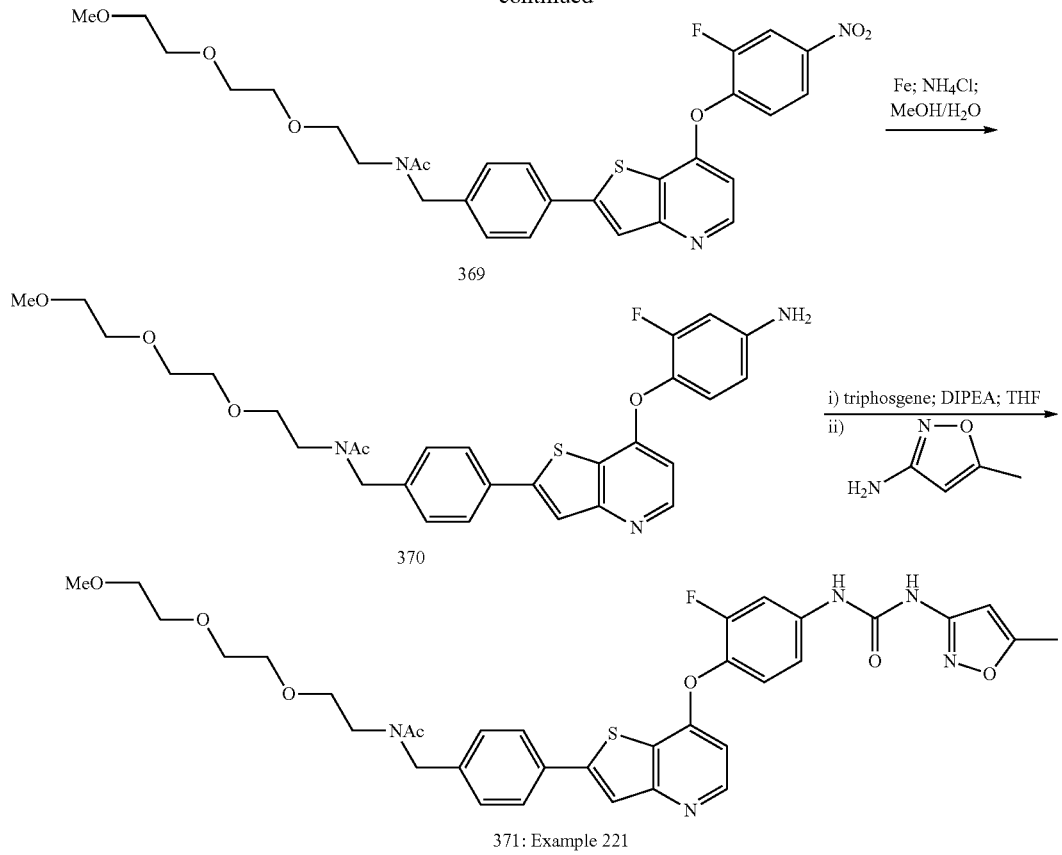

369

370

371: Example 221

Example 221

N-(4-(7-(2-Fluoro-4-(3-(5-methylisoxazol-3-yl)ureido)phenoxy)thieno[3,2-b]pyridin-2-yl)benzyl)-N-(2-(2-(2-methoxyethoxy)ethoxy)ethyl)acetamide (371)

Step 1: N-(4-(7-(2-fluoro-4-nitrophenoxy)thieno[3,2-b]pyridin-2-yl)benzyl)-N-(2-(2-(2-methoxyethoxy)ethoxy)ethyl)acetamide (369)

To a solution of 364 (0.50 g, 0.92 mmol) in dry tetrahydrofuran (50 mL) was added acetic anhydride (1.0 mL, 11 mmol). The reaction mixture was stirred for 24 h at room temperature then concentrated. The residue was partitioned between ethyl acetate and water; the organic phase was collected, washed with sat. NaHCO$_3$, brine, dried (MgSO$_4$), filtered and concentrated. The residue was purified by silica gel chromatography (eluent EtOAc) giving 369 (0.36 g, 67% yield). LRMS (M+H): 584.4

Step 2: N-(4-(7-(4-amino-2-fluorophenoxy)thieno[3,2-b]pyridin-2-yl)benzyl)-N-(2-(2-(2-methoxyethoxy)ethoxy)ethyl)acetamide, (370)

To a solution of 369 (0.36 g, 0.62 mmol) in MeOH (100 mL) was added iron dust (0.68 g, 12 mmol) and ammonium chloride (0.13 g, 2.5 mmol) in water (5 mL). The resulting mixture was heated to reflux for 4 h, then cooled, filtered through celite and concentrated. The residue was partitioned between dichloromethane and water; the organic phase was collected, washed with brine, dried over anhydrous magnesium sulfate, filtered, and concentrated. The product was purified by silica gel chromatography (eluent 2% MeOH in EtOAc) to give 370 (0.35 g, 100% yield). LRMS (M+H): 554.4

Step 3: N-(4-(7-(2-fluoro-4-(3-(5-methylisoxazol-3-yl)ureido)phenoxy)thieno[3,2-b]pyridin-2-yl)benzyl)-N-(2-(2-(2-methoxyethoxy)ethoxy)ethyl)acetamide (371)

To a solution of 370 (0.14 g, 0.25 mmol) and DIPEA (0.11 mL, 0.080 g, 0.61 mmol) in tetrahydrofuran (50 mL) at 0° C. was added triphosgene (0.030 g, 0.10 mmol) and the resulting solution was stirred for 0.5 h at 0° C. 3-Amino-5-methylisoxazole (0.074 g, 0.76 mmol) was added and the mixture was warmed to room temperature and stirred for 3 h, then quenched with 1 mL of water and concentrated under reduced pressure. The residue was partitioned between ethyl acetate and water; the organic phase was collected, washed with brine, dried over MgSO$_4$, filtered and concentrated. The product was purified by silica gel chromatography (10% MeOH in EtOAc), followed by Gilson reverse phase HPLC (35-65% acetonitrile/H$_2$O, Aquasil C$_{18}$, 30 min) and lyophilized. The residue (containing some formic acid from the HPLC) was partitioned between dichloromethane and 1M NaOH. The organic phase was dried (MgSO$_4$), filtered and concentrated to give 371 (65 mg, 38% yield) as a 2:1 mixture of rotamers by $^1$H NMR. $^1$H NMR (DMSO-d$_6$) δ (ppm) $^1$H: 9.64 (s, 1H); 9.19 (s, 1H); 8.50-8.48 (m, 1H); 8.04 (s, 0.4H); 8.01 (s, 0.6H); 7.89 (d, J=8.2, 0.4H); 7.82 (d, J=8.2, 0.6H); 7.72 (dd, J=12.9, 2.5, 1H); 7.45 (t, J=9.2, 1H); 7.33 (d, J=8.4, 2H); 7.27-7.24 (m, 1H); 6.61-6.59 (m, 1H); 6.54 (d, J=0.8, 1H); 4.68 (s, 0.4H); 4.59 (s, 0.6H); 3.52-3.38 (m, 12H); 3.21 (s, 1.8H); 3.20 (s, 1.2H); 2.35 (d, J=0.4, 3H); 2.12 (s, 1.8H); 2.00 (1.2H). LRMS (M+H): 678.8 sodium sulfate and concentrated to dryness. The residue was purified by flash chromatography (Biotage, Snap 10 column, gradient: 3% 10 CV, 3% to 5% 2 CV, and 5% 10 CV MeOH in DCM) affording 372 (0.1097 g, 0.169 mmol, 59.0% yield) as light brown solid. m/z: 651.4 (M+H)$^+$.

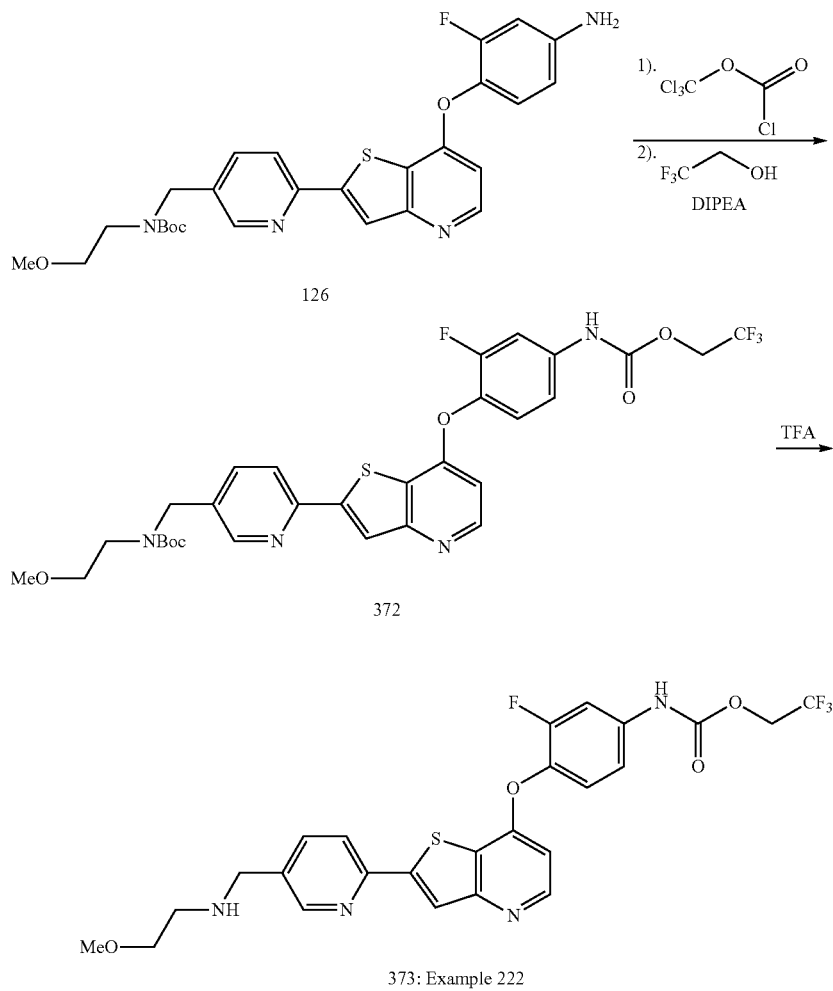

Example 222

2,2,2-Trifluoroethyl 3-fluoro-4-(2-(5-((2-methoxyethylamino)methyl)pyridin-2-yl)thieno[3,2-b]pyridin-7-yloxy)phenylcarbamate (373)

Step 1. 4-(2-(5-(((tert-Butoxycarbonyl(2-methoxyethyl)amino)methyl)pyridin-2-yl)thieno[3,2-b]pyridin-7-yloxy)-3-fluorophenyl 2,2,2-trifluoroethyl methylcarbamate (372)

Diphosgene (0.017 ml, 0.143 mmol) was added to a solution of aniline 126 (0.15 g, 0.286 mmol) in THF (2.86 ml) and the reaction mixture was stirred vigorously for 2 hrs. To the reaction mixture was added 2,2,2-trifluoroethanol (0.042 ml, 0.572 mmol) and a solution of DIPEA (0.100 ml, 0.572 mmol) in THF (2.86 ml). The reaction mixture was stirred vigorously overnight, diluted with DCM, washed with saturated ammonium chloride solution, dried over anhydrous

Step 2. 2,2,2-Trifluoroethyl 3-fluoro-4-(2-(5-((2-methoxyethylamino)methyl)pyridin-2-yl)thieno[3,2-b]pyridin-7-yloxy)phenylcarbamate (373)

To a suspension of 372 (0.1097 g, 0.169 mmol) in DCM (1.0 ml) was added TFA (1.0 ml, 12.98 mmol) and the reaction mixture was stirred at room temperature for 2 hrs. The reaction mixture was concentrated under reduced pressure, the residue dissolved in DCM, washed with 1N NaOH solution, water, dried over anhydrous sodium sulfate and concentrated under reduced pressure affording 373 (0.0543 g, 0.097 mmol, 57.3% yield) as white solid. $^1$H-NMR (DMSO-D$_6$, 400 MHz) 10.55 (s, 1H), 8.57 (s, 1H), 8.52 (d, J=5.62 Hz, 1H), 8.32 (s, 1H), 8.23 (d, J=8.1 Hz, 1H), 7.90 (d, J=8.10 Hz, 1H), 7.63 (d, J=9 Hz, 1H), 7.52 (d, J=13.5 Hz, 1H), 7.39 (t, J=9.0 Hz, 1H), 6.66 (d, J=6.7 Hz, 1H), 4.85 (q, J=9.0 Hz, 2H), 3.79 (s, 2H), 3.41 (t, J=5.5 Hz, 2H), 3.24 (s, 3H), 2.66 (t, J=5.5 Hz, 2H). m/z: (M+H)$^+$ 551.4.

Scheme 33

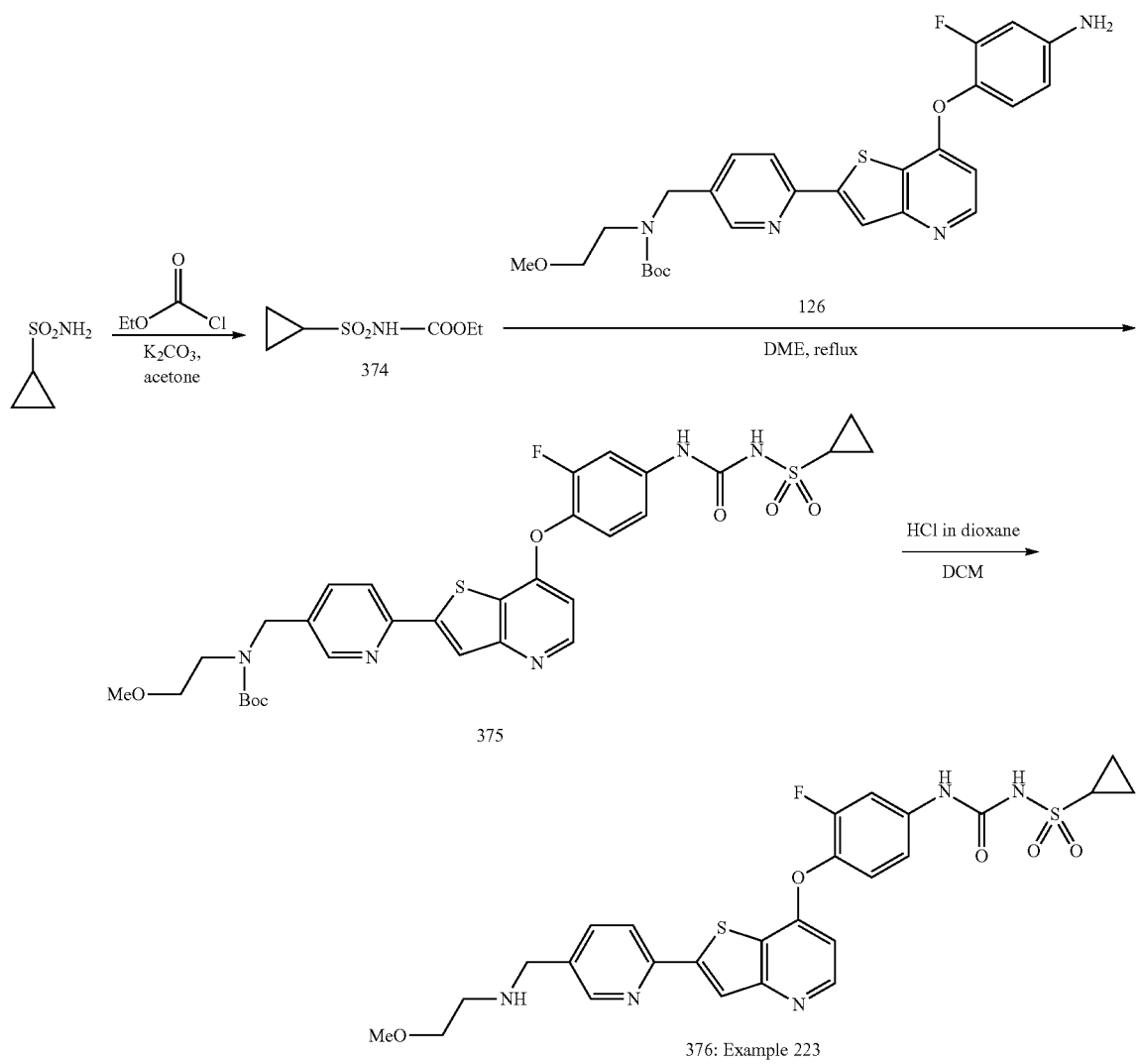

Example 223

N-(3-fluoro-4-(2-(5-((2-methoxyethylamino)methyl)pyridin-2-yl)thieno[3,2-b]pyridin-7-yloxy)phenylcarbamoyl)cyclopropanesulfonamide (376)

Step 1: ethyl cyclopropylsulfonylcarbamate (374)

To a solution of cyclopropanesulfonamide (Li, J. et al; Synlett 2006, 5, 725-728) (800 mg, 6.60 mmol) in acetone (25 ml) was added potassium carbonate (2.738 g, 3 eq, 19.81 mmol) and ethyl chloroformate (1.075 g, 1.5 eq, 9.90 mmol) and the reaction mixture was stirred at RT overnight. The reaction mixture was poured into water and made acidic (pH 1) with conc HCl then extracted with EtOAc. The extract was collected, dried over $Na_2SO_4$, filtered and concentrated. Purification of the residue by column chromatography (eluent 30% EtOAc in hexanes) afforded 374 as a colourless oil (800 mg, 63%). $^1$H NMR (DMSO, $d_6$) 11.47 (s, 1H), 4.10 (q, J=10.27 Hz, 2H), 2.90 (m, 1H), 1.19 (t, J=7.24 Hz, 3H), 1.039 (m, 4H).

Step 2: tert-butyl(6-(7-(4-(3-(cyclopropylsulfonyl)ureido)-2-fluorophenoxy)thieno[3,2-b]pyridin-2-yl)pyridin-3-yl)methyl(2-methoxyethyl)carbamate (375)

To a solution of the amine 126 (500 mg, 0.953 mmol) in DME (4 ml) was added the carbamate 374 (460 mg, 2.5 eq, 2.383 mmol) and the reaction mixture was heated to 120° C. for 1 day. The mixture was cooled to RT, diluted with EtOAc and water and the organic phase was collected, dried over $Na_2SO_4$, filtered and concentrated. Purification of the residue by column chromatography (eluent EtOAc to 50% Acetone in EtOAc) afforded 375 as a brown oil (130 mg, 55%). MS (m/z)=672.5 (M+H)

Step 3: N-(3-fluoro-4-(2-(5-((2-methoxyethylamino)methyl)pyridin-2-yl)thieno[3,2-b]pyridin-7-yloxy)phenylcarbamoyl)cyclopropanesulfonamide (376)

To a solution of the 375 (140 mg, 0.208 mmol) in DCM (5 ml) was added HCl in dioxane (0.5 ml, 2 mmol, 9.6 eq, 4M in dioxane) and the reaction mixture was stirred for 4 hours. The mixture was diluted with EtOAc, made basic with NaHCO₃ solution and extracted with EtOAc/acetone. The organic phase was collected and discarded. The aqueous phase was concentrated and the residue was suspended in a mixture of DCM and acetone. The solution phase was collected, dried with Na₂SO₄, filtered and concentrated to afford 376 as a beige solid after further trituration with Et₂O (yield 8 mg, 7%). ¹H NMR (DMSO-d6): 8.67 (s, 1H), 8.56 (s, 1H), 8.47 (d, J=5.28, 1H), 8.27 (s, 1H), 8.19 (d, J=8.02 Hz, 1H), 7.85 (m, 2H), 7.80 (s, 1H), 7.22 (m, 2H), 6.59 (d, J=5.28 Hz, 1H), 3.76 (s, 2H), 3.40 (m, 2H), 3.20 (s, 3H), 2.76 (m, 1H), 2.60 (m, 2H), 0.75 (m, 2H), 0.65 (m, 2H). LRMS(ESI): (calc.) 571.64 (found) 572.58 (MH)⁺.

Additional compounds according to the present invention include those in Table 2.

TABLE 2

| Cpd | Ex | Structure | Characterization |
|---|---|---|---|
| 377 | 224 | 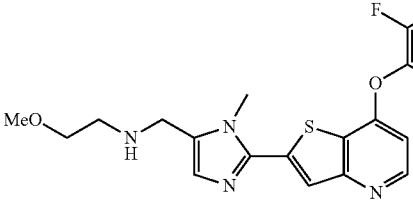 1-(3-(dimethylphosphoryl)phenyl)-3-(3-fluoro-4-(2-(5-((2-methoxyethylamino)methyl)-1-methyl-1H-imidazol-2-yl)thieno[3,2-b]pyridin-7-yloxy)phenyl)urea | ¹H NMR (DMSO-d₆) δ (ppm): 1H: 8.50 (d, 1H, J = 5.5 Hz), 7.87 (s, 1H), 7.84 (s, 1H), 7.74 (dd, 1H, J1 = 2.4 Hz, J2 = 13.3 Hz), 7.62 (m, 1H), 7.44-7.26 (m, 4H), 6.93 (s, 1H), 6.66 (d, 1H, J = 5.5 Hz), 3.89 (s, 3H), 3.74 (m, 2H), 3.38 (t, 2H, J = 5.6 Hz), 3.22 (s, 3H), 2.66 (m, 2H), 1.98 (m, 1H), 1.62 (d, 6H, J = 13.3 Hz). LRMS(ESI): (calc.) 622.2 (found) 623.5 (MH)+ |
| 378 | 225 | 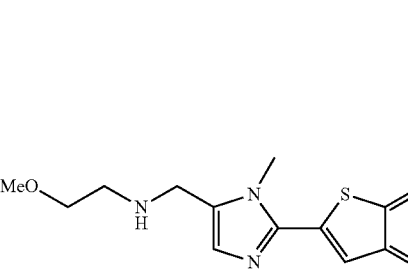 1-(3-fluoro-4-(2-(5-((2-methoxyethylamino)methyl)-1-methyl-1H-imidazol-2-yl)thieno[3,2-b]pyridin-7-yloxy)phenyl)-3-o-tolylurea | ¹H NMR (DMSO-d₆) δ (ppm): 1H: 9.37 (s, 1H), 8.48 (d, J = 5.48 Hz, 1H), 8.04 (s, 1H), 7.85 (s, 1H), 7.73 (m, 2H), 7.40 (m, 1H), 7.21-7.12 (m, 3H), 6.93 (m, 2H), 6.64 (d, J = 5.48 Hz, 1H), 3.87 (s, 3H), 3.72 (s, 2H), 3.36 (m, 2H), 3.21 (s, 3H), 2.65 (t, J = 5.48 Hz, 2H), 2.22 (s, 3H) LRMS(ESI): (calc.) 560.64 (found) 561.5 (MH)+ |
| 379 | 226 | 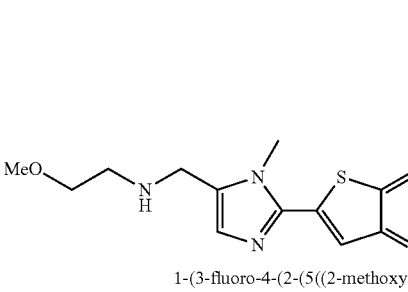 1-(3-fluoro-4-(2-(5((2-methoxyethylamino)methyl)-1-methyl-1H-imidazol-2-yl)thieno[3,2-b]pyridin-7-yloxy)phenyl)-3-(2-fluoro-5-(trifluoromethyl)phenyl)urea | ¹H NMR (DMSO-d₆) δ (ppm): 9.56 (s, 1H), 9.03 (s, 1H), 8.55 (d, 1H, J = 7.3 Hz), 8.48 (d, 1H, J = 5.3 Hz), 7.85 (s, 1H), 7.73 (dd, J1 = 13.1 Hz, J2 = 2.3 Hz), 7.50-7.21 (m, 3H), 7.22 (d, 1H, J = 8.8 Hz), 6.92 (s, 1H), 6.64 (d, 1H, J = 5.5 Hz), 3.87 (s, 3H), 3.72 (s, 2H), 3.36 (t, 2H, J = 5.7 Hz), 2.65 (t, 2H, J = 5.7 Hz), 2.02 (s, br, 1H). LRMS(ESI): (calc.) 632.2 (found) 633.5 (MH)+ |
| 380 | 227 | 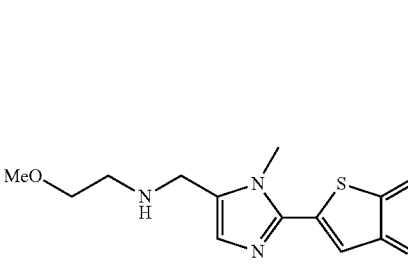 1-(2,5-difluorophenyl)-3-(3-fluoro-4-(2-(5-((2-methoxyethylamino)methyl)-1-methyl-1H-imidazol-2-yl)thieno[3,2-b]pyridin-7-yloxy)phenyl)urea | ¹H NMR (DMSO-d₆) δ (ppm): 9.55 (s, 1H), 8.92 (s, 1H), 8.48 (m, 1H), 8.0 (m, 1H), 7.85 (s, 1H), 7.72 (m, 1H), 7.42 (t, J = 8.9 Hz, 1H), 7.30-7.20 (m, 2H), 6.91 (s, 1H), 6.81 (m, 1H), 6.64 (d, J = 5.48 Hz, 1H), 3.87 (s, 3H), 3.72 (s, 2H), 3.36 (t, J = 5.67 hz, 2H), 3.20 (s, 3H), 2.64 (t, J = 5.67 Hz, 2H). LRMS(ESI): (calc.) 582.60 (found) 583.5 (MH)+ |

TABLE 2-continued

| Cpd | Ex | Structure | Characterization |
|---|---|---|---|
| 381 | 228 | 1-(3-fluoro-4-(2-(5-((2-methoxyethylamino)methyl)-1-methyl-1H-imidazol-2-yl)thieno[3,2-b]pyridin-7-yloxy)phenyl)-3-(4-methoxyphenyl)urea | $^1$H NMR (DMSO-$d_6$) δ (ppm): 8.96 (s, 1H), 8.59 (s, 1H), 8.47 (d, 1H, J = 5.5 Hz), 7.85 (s, 1H), 7.70 (dd, 1H, J1 = 2.3 Hz, J2 = 13.3 Hz), 7.38 (t, 1H, J = 9.0 Hz), 7.33-7.31 (m, 2H), 7.21-7.18 (m, 1H), 6.91 (s, 1H), 6.85-6.83 (m, 2H), 6.63 (d, 1H, J = 5.3 Hz), 3.87 (s, 3H), 3.72 (s, 2H), 3.67 (s, 3H), 3.36 (t, 2H, J = 5.6 Hz), 3.19 (s, 3H), 2.65 (t, 2H, J = 5.5 Hz). LRMS(ESI): (calc.) 576.2 (found) 577.5 (MH)+ |
| 382 | 229 | 1-(3-bromophenyl)-3-(3-fluoro-4-(2-(5-((2-methoxyethylamino)methyl)-1-methyl-1H-imidazol-2-yl)thieno[3,2-b]pyridin-7-yloxy)phenyl)urea | $^1$H NMR (DMSO-$d_6$) δ (ppm): 9.15 (s, 1H), 9.02 (s, 1H), 8.48 (d, J = 5.28 Hz, 1H), 7.86 (s, 1H), 7.81 (m, 1H), 7.70 (m, 1H), 7.41 (t, J = 8.99 Hz, 1H), 7.31 (m, 1H), 7.24 (m, 3H), 7.14 (m, 1H), 6.94 (s, 1H), 6.64 (d, J = 5.28 Hz, 1H), 3.87 (s, 3H), 3.77 (s, 2H), 3.375 (t, J = 5.48 hz, 2H), 3.20 (s, 3H), 2.69 (t, J = 5.48 Hz, 2H) LRMS(ESI): (calc.) 625.51 (found) 625.4/627.4 (MH)+ |
| 383 | 230 | 1-(4-chloro-3-(trifluoromethyl)phenyl)-3-(3-fluoro-4-(2-(5-((2-methoxyethylamino)methyl)-1-methyl-1H-imidazol-2-yl)thieno[3,2-b]pyridin-7-yloxy)phenyl)urea | $^1$H NMR (DMSO-$d_6$) δ (ppm): 9.35 (s, 1H), 9.29 (s, 1H), 8.47 (d, J = 5.48 Hz, 1H), 8.06 (m, 1H), 7.84 (s, 1H), 7.70 (m, 1H), 7.59 (m, 2H), 7.41 (t, J = 8.99 Hz, 1H), 7.25 (m, 1H), 6.91 (s, 1H), 6.63 (d, J = 5.48 Hz, 1H), 3.86 (s, 3H), 3.72 (s, 2H), 3.35 (t, J = 5.67 Hz, 2H), 3.19 (s, 3H), 2.64 (t, J = 5.67 Hz, 2H) LRMS(ESI): (calc.) 649.06 (found) 649.5 (M)+ |
| 384 | 231 | 3-(3-(3-fluoro-4-(2-(5-((2-methoxyethylamino)methyl)-1-methyl-1H-imidazol-2-yl)thieno[3,2-b]pyridin-7-yloxy)phenyl)ureido)benzamide | $^1$H NMR (DMSO-$d_6$) δ (ppm): 10.16 (s, br, 1H), 9.94 (s, br, 1H), 8.52 (d, 1H, J = 5.4 Hz), 7.98-7.90 (m, 3H), 7.81 (dd, 1H, J1 = 2.5 Hz, J2 = 13.2 Hz), 7.67-7.65 (m, 1H), 7.47-7.42 (m, 2H), 7.36-7.32 (m, 3H), 6.96 (s, 1H), 6.69 (d, 1H, J = 5.4 Hz), 3.92 (s, 3H), 3.77 (s, 2H), 3.40 (t, 2H, J = 5.4 Hz), 3.35 (s, 3H), 2.69 (t, 2H, J = 5.2 Hz), 1.81 (s, 1H). LRMS(ESI): (calc.) 589.2 (found) 590.5 (MH)+ |

TABLE 2-continued

| Cpd | Ex | Structure | Characterization |
|---|---|---|---|
| 385 | 232 | 4-(3-(3-fluoro-4-(2-(5-((2-methoxyethylamino)methyl)-1-methyl-1H-imidazol-2-yl)thieno[3,2-b]pyridin-7-yloxy)phenyl)ureido)benzamide | $^1$H NMR (DMSO-d$_6$) δ (ppm): 9.16 (s, 1H), 9.07 (s, 1H), 8.47 (d, J = 5.48 hz, 1H), 7.85 (s, 1H), 7.73 (m, 2H), 7.70 (m, 1H), 7.45 (m, 2H), 7.41 (t, J = 8.99 hz, 1H), 7.22 (m, 1H), 7.17 (s, 1H), 6.91 (s, 1H), 6.64 (d, J = 5.28 hz, 1H), 3.87 (s, 3H), 3.73 (s, 2H), 3.36 (t, J = 5.67 Hz, 2H), 3.2 (s, 3H), 2.65 (t, J = 5.67 Hz, 2H) LRMS(ESI): (calc.) 589.64 (found) 590.4 (MH)+ |
| 386 | 233 | N1-(3-fluoro-4-(2-(5-((2-methoxyethylamino)methyl)-1-methyl-1H-imidazol-2-yl)thieno[3,2-b]pyridin-7-yloxy)phenyl)-N3-(3-(oxazol-5-yl)phenyl)malonamide | $^1$H NMR (DMSO-d$_6$) δ (ppm): 10.55 (s, 1H), 10.35 (s, 1H), 8.47 (d, J = 5.48 Hz, 1H), 8.42 (s, 1H), 8.0 (s, 1H), 7.83 (m, 2H), 7.61 (s, 1H), 7.53-7.39 (m, 5H), 6.92 (s, 1H), 6,65 (d, J = 5.28 Hz, 1H), 3.87 (s, 3H), 3.72 (s, 2H), 3.51 (s, 2H), 3.34 (t, J = 6.26 Hz, 2H), 3.2 (s, 3H), 2.65 (t, J = 5.67 Hz, 2H). LRMS(ESI): (calc.) 655.70 (found) 656.6 (MH)+ |

Additional compounds according to the present invention include those in Table 3.

TABLE 3

| Cpd | Ex | Structure | Characterization |
|---|---|---|---|
| 387 | 234 | 1-(3-(dimethylphosphoryl)phenyl)-3-(3-fluoro-4-(2-(6-((2-methoxyethylamino)methyl)pyridin-2-yl)thieno[3,2-b]pyridin-7-yloxy)phenyl)urea | $^1$H NMR (DMSO-d$_6$) δ (ppm): 9.10 (s, 1H), 9.02 (s, 1H), 8.50 (d, 1H, J = 5.5 Hz), 8.32 (s, 1H), 8.10 (d, 1H, J = 7.9 Hz), 7.89 (t, 1H, J = 7.9 Hz), 7.84 (d, 1H, J = 12.7 Hz), 7.74 (dd, 1H, J = 2.6 Hz, J = 13.3 Hz), 7.62 (d, 1H, J = 8.0 Hz), 7.4-7.5 (m, 3H), 7.33 (m, 1H), 7.26 (m, 1H), 6.62 (d, 1H, J = 5.7 Hz), 3.85 (s, 2H), 3.22 (s, 3H), 2.72 (t, 2H, J = 5.5 Hz), 1.64 (s, 3H), 1.60 (s, 3H) LRMS(ESI): (calc.) 619.2 (found) 620.4 (MH)+ |

TABLE 3-continued

| Cpd | Ex | Structure | Characterization |
|---|---|---|---|
| 388 | 235 | 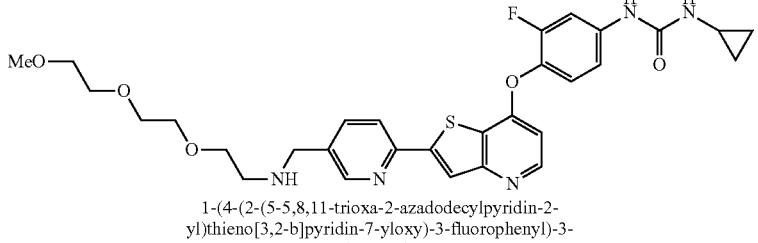<br>1-(4-(2-(5-5,8,11-trioxa-2-azadodecylpyridin-2-yl)thieno[3,2-b]pyridin-7-yloxy)-3-fluorophenyl)-3-cyclopropylurea | $^1$H NMR (DMSO-$d_6$) δ (ppm): 8.80 (s, 1H); 8.57 (s, 1H); 8.51 (d, J = 5.5, 1H); 8.31 (s, 1H); 8.23 (d, J = 8.0, 1H); 7.89 (dd, J = 8.0, 1.5, 1H); 7.73 (dd, J = 13.5, 2.2, 1H); 7.38 (t, J = 9.0, 1H); 7.20 (d, J = 8.2, 1H); 6.67 (d, J = 2.7, 1H); 6.64 (d, J = 5.5, 1H); 3.78 (s, 2H); 3.56-45 (m, 12H); 3.41 (t, J = 5.7, 2H); 3.21 (s, 3H); 2.66 (d, J = 5.7, 2H); 2.58-2.51 (m, 1H); 0.66-0.62 (m, 2H); 0.44-0.41 (m, 2H).<br>LRMS(ESI): (calc.) 595.7 (found) 596.4 (MH)+ |
| 389 | 236 | 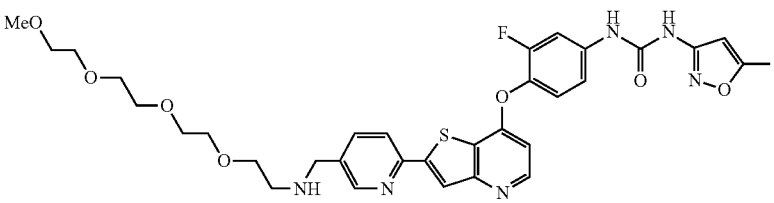 [SMILES: COCCOCCOCCOCCNCc1ccc(-c2cc3nccc(Oc4ccc(NC(=O)Nc5cc(C)on5)cc4F)c3s2)nc1]<br>1-(4-(2-(5-5,8,11,14-tetraoxa-2-azapentadecylpyridin-2-yl)thieno[3,2-b]pyridin-7-yloxy)-3-fluorophenyl)-3-(5-methylisoxazol-3-yl)urea | $^1$H NMR (DMSO-$d_6$) δ (ppm): 9.66 (s, 1H); 9.23 (s, 1H); 8.57 (s, 1H); 8.52 (d, J = 5.3, 1H); 8.32 (s, 1H); 8.23 (d, J = 8.0, 1H); 7.90 (dd, J = 8.2, 2.2, 1H); 7.74 (dd, J = 13.1, 2.5, 1H); 7.47 (t, J = 9.0, 1H); 7.30-7.26 (m, 1H); 6.66 (d, J = 5.9, 1H); 6.56 (d, J = 0.9, 1H); 3.78 (s, 2H); 3.52-3.47 (m, 12H); 3.40-3.36 (m, 2H); 3.21 (s, 3H); 2.65 (t, J = 5.7, 2H); 2.37 (s, 3H).<br>LRMS(ESI): (calc.) 680.8 (found) 681.6 (MH)+ |
| 390 | 237 | 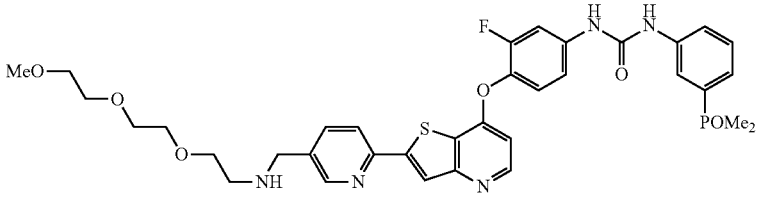<br>1-(4-(2-(5-5,8,11-trioxa-2-azadodecylpyridin-2-yl)thieno[3,2-b]pyridin-7-yloxy)-3-fluorophenyl)-3-(3-(dimethylphosphoryl)phenyl)urea | $^1$H NMR (DMSO-$d_6$) δ (ppm): 9.16 (s, 1H), 9.08 (s, 1H), 8.58 (d, J = 2.0 Hz, 1H), 8.53 (d, J = 5.2 Hz, 1H), 8.33 (s, 1H), 8.24 (d, J = 8.4 Hz, 1H), 7.93-7.84 (m, 2H), 7.77 (dd, J = 12.8, 2.4 Hz, 1H), 7.64 (d, J = 8.0 Hz, 1H), 7.49-7.41 (m, 2H), 7.37 (dd, J = 10.8, 7.6 Hz, 1H), 7.31-7.26 (m, 1H), 6.67 (d, J = 5.6 Hz, 1H), 3.80 (s, 2H), 3.53-3.46 (m, 8H), 3.44-3.39 (m, 2H), 3.22 (s, 3H), 2.67 (t, J = 5.6 Hz, 2H), 1.64 (d, J = 13.2 Hz, 6H).<br>LRMS(ESI): (calc.) 707.23 (found) 708.7 (MH)+ |

TABLE 3-continued

| Cpd | Ex | Structure | Characterization |
|---|---|---|---|
| 391 | 238 | 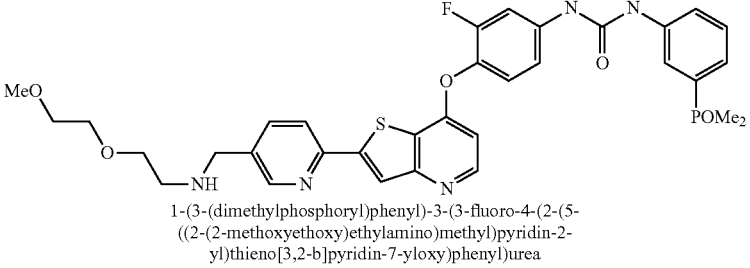<br>1-(3-(dimethylphosphoryl)phenyl)-3-(3-fluoro-4-(2-(5-((2-(2-methoxyethoxy)ethylamino)methyl)pyridin-2-yl)thieno[3,2-b]pyridin-7-yloxy)phenyl)urea | $^1$H NMR (DMSO-$d_6$) δ (ppm): 9.12 (s, 1H), 9.05 (s, 1H), 8.58 (d, J = 2.0 Hz, 1H), 8.53 (d, J = 5.6 Hz, 1H), 8.33 (s, 1H), 8.24 (d, J = 8.4 Hz, 1H), 7.92-7.83 (m, 2H), 7.77 (dd, J = 13.2, 2.4 Hz, 1H), 7.64 (d, J = 8.4 Hz, 1H), 7.49-7.41 (m, 2H), 7.37 (dd, J = 10.8, 7.0 Hz, 1H), 7.29 (dd, J = 8.8, 1.2 Hz, 1H), 6.67 (d, J = 5.2 Hz, 1H), 3.79 (s, 2H), 3.52-3.40 (m, 6H), 3.24 (s, 3H), 2.66 (t, J = 5.6 Hz, 2H), 1.64 (d, J = 13.2 Hz, 6H).<br>LRMS(ESI): (calc.) 663.21 (found) 664.4 (MH)+ |
| 392 | 239 | 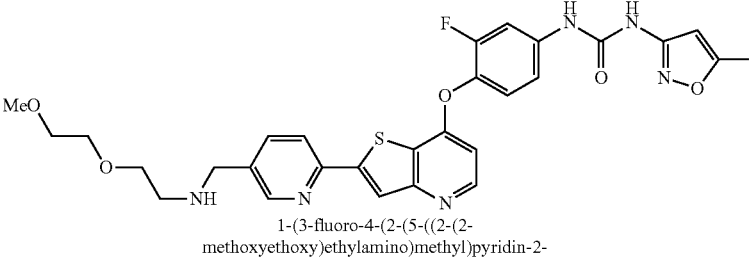<br>1-(3-fluoro-4-(2-(5-((2-(2-methoxyethoxy)ethylamino)methyl)pyridin-2-yl)thieno[3,2-b]pyridin-7-yloxy)phenyl)-3-(5-methylisoxazol-3-yl)urea | $^1$H NMR (DMSO-$d_6$) δ (ppm): 9.64 (s, 1H), 9.23 (bs, 1H), 8.58 (d, J = 1.6 Hz, 1H), 8.53 (d, J = 5.2 Hz, 1H), 8.33 (s, 1H), 8.24 (d, J = 8.0 Hz, 1H), 7.90 (dd, J = 8.0, 1.6 Hz, 1H), 7.74 (dd, J = 13.0, 2.4 Hz, 1H), 7.47 (t, J = 8.8 Hz, 1H), 7.31-7.26 (m, 1H), 6.67 (d, J = 5.2 Hz, 1H), 6.56 (s, 1H), 3.80 (s, 2H), 3.53-3.40 (m, 6H), 3.24 (s, 3H), 2.67 (t, J = 5.6 Hz, 2H), 2.38 (s, 3H).<br>LRMS(ESI): (calc.) 592.19 (found) 593.5 (MH)+ |
| 393 | 240 | 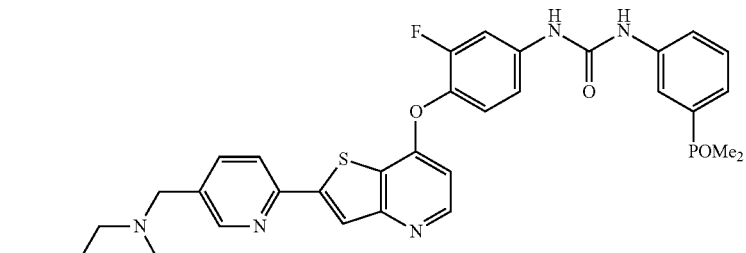<br>N-((6-(7-(4-(3-(3-(dimethylphosphoryl)phenyl)ureido)-2-fluorophenoxy)thieno[3,2-b]pyridin-2-yl)pyridin-3-yl)methyl)-N-(2-methoxyethyl)acetamide | $^1$H NMR (DMSO-$d_6$) δ (ppm): (mixture of rotamers) 9.22 (s, 1H), 9.14 (s, 1H), 8.56-8.48 (m, 2H), 8.38-8.32 (2s, 1H), 8.29 and 8.23 (2d, J = 8.0 Hz, 1H), 7.87 (d, J = 12.8 Hz, 1H), 7.82-7.73 (m, 2H), 7.64 (d, J = 7.6 Hz, 1H), 7.49-7.41 (m, 2H), 7.40-7.33 (m, 1H), 7.29 (d, J = 10 Hz, 1H), 6.70-6.65 (m, 1H), 7.71 and 4.59 (2s, 2H), 3.54-3.36 (m, 4H), 3.24 and 3.21 (2s, 3H), 2.13 and 2.05 (2s, 3H), 1.64 (d, J = 13.6 Hz, 6H).<br>LRMS(ESI): (calc.) 661.19 (found) 662.6 (MH)+ |

TABLE 3-continued

| Cpd | Ex | Structure | Characterization |
|---|---|---|---|
| 394 | 241 | 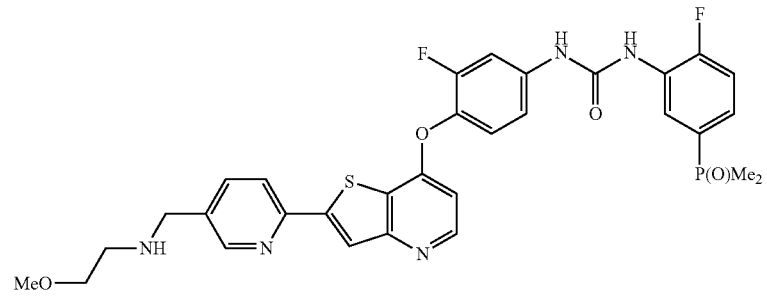<br>1-(5-(dimethylphosphoryl)-2-fluorophenyl)-3-(3-fluoro-4-(2-(5-((2-methoxyethylamino)methyl)pyridin-2-yl)thieno[3,2-b]pyridin-7-yloxy)phenyl)urea | $^{1}$H NMR (MeOH-d$_{4}$) δ (ppm): two NH urea are missing, 8.73 (s, 1H), 8.62 (ddd, J = 12.9, 7.7, 1.9 Hz, 1H), 8.49 (d, J = 5.3 Hz, 1H), 8.34 (bs, 1H, formate salt), 8.19 (d, J = 8.2 Hz, 1H), 8.15 (s, 1H), 8.07 (d, J = 6.7 Hz, 1H), 7.78 (dd, J = 12.9, 2.3 Hz, 1H), 7.55-7.45 (m, 1H), 7.41-7.31 (m, 2H), 7.25 (dd, J = 8.9, 1.4 Hz, 1H), 6.68 (d, J = 5.5 Hz, 1H), 4.34 (s, 2H), 3.70 (t, J = 5.0 Hz, 2H), 3.35 (s, 3H), 3.30 (t, J = 5.1 Hz, 2H), 1.82 (d, J = 13.5 Hz, 6H), one NH is missing.<br>LRMS(ESI): (calc.) 637.64 (found) 638.5 (MH)+ |
| 395 | 242 | 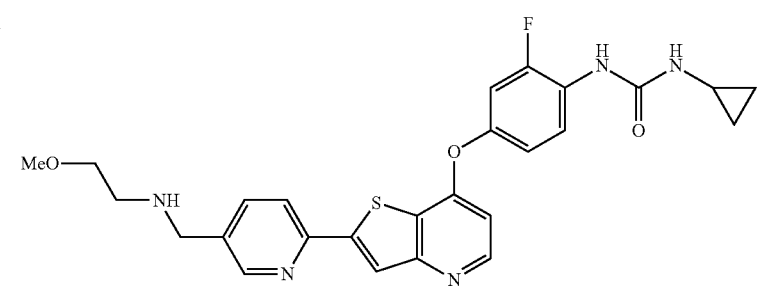 [SMILES: COCCNCc1ccc(-c2cc3nccc(Oc4ccc(NC(=O)NC5CC5)c(F)c4)c3s2)nc1]<br>1-cyclopropyl-3-(2-fluoro-4-(2-(5-((2-methoxyethylamino)methyl)pyridin-2-yl)thieno[3,2-b]pyridin-7-yloxy)phenyl)urea | $^{1}$H NMR (DMSO-d$_{6}$) δ (ppm): 8.56 (s, 1H); 8.52 (d, J = 8.5, 1H); 8.30 (s, 1H); 8.25-8.18 (m, 2H); 7.89 (dd, J = 8.0, 2.1, 1H); 7.34 (dd, J = 11.7, 2.5, 1H); 7.09 (dd, J = 8.8, 1.8, 1H); 6.82 (d, J = 2.7, 1H); 6.69 (d, J = 5.5, 1H); 3.77 (s, 2H); 3.41 (t, J = 5.7, 2H); 3.24 (s, 3H); 2.65 (t, J = 5.7, 2H); 2.56 (septet, J = 3.3, 1H); 0.67-0.62 (m, 2H); 0.43-0.40 (m, 2H).<br>LRMS(ESI): (calc.) 507.6 (found) 508.4 (MH)+ |
| 396 | 243 | 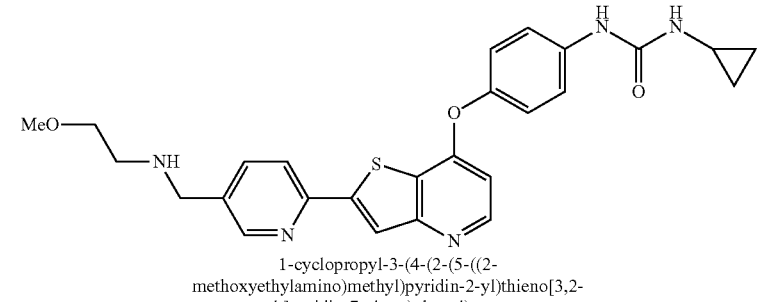<br>1-cyclopropyl-3-(4-(2-(5-((2-methoxyethylamino)methyl)pyridin-2-yl)thieno[3,2-b]pyridin-7-yloxy)phenyl)urea | $^{1}$H NMR (DMSO-d$_{6}$) δ (ppm): 8.59 (s, 1H), 8.56 (d, J = 2.0 Hz, 1H), 8.49 (d, J = 5.6 Hz, 1H), 8.29 (s, 1H), 8.22 (d, J = 8.4 Hz, 1H), 7.88 (dd, J = 8.4, 2.0 Hz, 1H), 7.54 (d, J = 9.0 Hz, 2H), 7.18 (d, J = 9.0 Hz, 2H), 6.61 (d, J = 5.6 Hz, 1H), 6.56 (bs, 1H), 3.77 (s, 2H), 3.41 (t, J = 5.6 Hz, 2H), 3.24 (s, 3H), 2.65 (t, J = 5.6 Hz, 2H), 2.58-2.50 (m 1H), 2.26 (bs, 1H), 0.68-0.60 (m, 2H), 0.44-0.39 (m, 2H).<br>LRMS(ESI): (calc.) 489.18 (found) 490.5 (MH)+ |

TABLE 3-continued

| Cpd | Ex | Structure | Characterization |
|---|---|---|---|
| 397 | 244 | 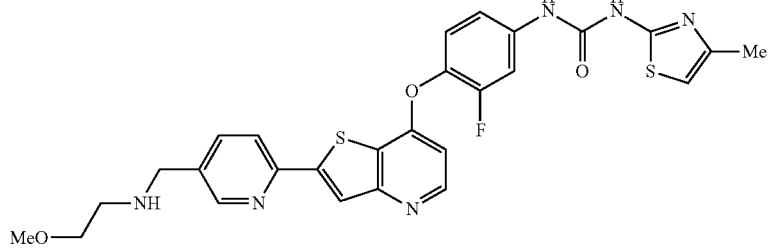<br>1-(3-fluoro-4-(2-(5-((2-methoxyethylamino)methyl)pyridin-2-yl)thieno[3,2-b]pyridin-7-yloxy)phenyl)-3-(4-methylthiazol-2-yl)urea | $^1$H NMR (DMSO-$d_6$) δ (ppm): 9.40 (s, 1H), one NH urea is missing, 8.58 (bs, 1H), 8.53 (d, J = 5.5 Hz, 1H), 8.33 (s, 1H), 8.24 (d, J = 8.0 Hz, 1H), 7.91 (dd, J = 8.3, 1.7 Hz, 1H), 7.78 (dd, J = 13.0, 2.2 Hz, 1H), 7.47 (t, J = 9.0 Hz, 1H), 7.35 (bd, J = 10.3, 1H), 6.67 (d, J = 5.3 Hz, 1H), 6.64 (s, 1H), 3.81 (s, 2H), one CH2 is masked by water, 3.25 (s, 3H), 2.69 (t, J = 5.6 Hz, 2H), 2.23 (s, 3H), one NH is missing. LRMS(ESI): (calc.) 564.65 (found) 565.4 (MH)+ |
| 398 | 245 | 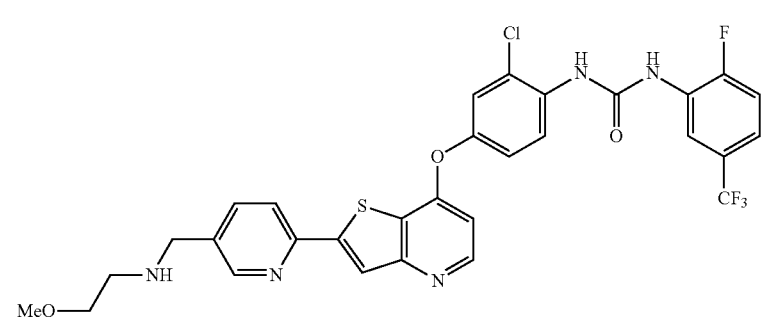 [SMILES: COCCNCc1ccc(-c2cc3nccc(Oc4ccc(NC(=O)Nc5cc(C(F)(F)F)ccc5F)c(Cl)c4)c3s2)nc1]<br>1-(2-chloro-4-(2-(5-((2-methoxyethylamino)methyl)pyridin-2-yl)thieno[3,2-b]pyridin-7-yloxy)phenyl)-3-(2-fluoro-5-(trifluoromethyl)phenyl)urea | $^1$H NMR (DMSO-$d_6$) δ (ppm): 9.7 (d, J = 2.6 Hz, 1H), 9.03 (s, 1H), 8.65 (dd, J = 2.1 Hz, J = 7.3 Hz, 1H), 8.56 (d, J = 1.9 Hz, 1H), 8.54 (d, J = 5.4 Hz, 1H), 8.32 (s, 1H), 8.26 (d, J = 9.1 Hz, 1H), 8.23 (d, J = 8.2 Hz, 1H), 7.89 (dd, J = 2.1 Hz, J = 8.2 Hz, 1H), 7.6 (d, J = 2.9 Hz, 1H), 7.53 (dd, J = 8.5 Hz, J = 10.6 Hz, 1H), 7.44-7.42 (m, 1H), 7.32 (dd, J = 2.6 Hz, J = 9.1 Hz, 1H), 6.74 (d, J = 5.5 Hz, 1H), 3.78 (s, 2H), 3.41 (t, J = 5.8 Hz, 2H), 3.24 (s, 3H), 2.65 (t, J = 5.8 Hz, 2H)<br>m/z: (M + 2) + 2 /2 323.7 (100%), (MH)+ 646.5 (32%) |
| 399 | 246 | 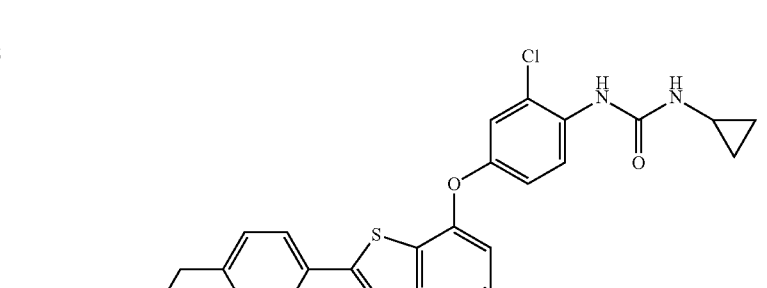<br>1-(2-chloro-4-(2-(5-((2-methoxyethylamino)methyl)pyridin-2-yl)thieno[3,2-b]pyridin-7-yloxy)phenyl)-3-cyclopropylurea | $^1$H NMR (DMSO-$d_6$) δ (ppm): 8.56 (d, J = 2.0 Hz, 1H), 8.52 (d, J = 5.4 Hz, 1H), 8.29 (s, 1H), 8.25 (d, J = 9.3 Hz, 1H), 8.21 (d, J = 8.4 Hz, 1H), 7.99 (s, 1H), 7.89 (dd, J = 2.1 Hz, J = 8.3 Hz, 1H), 7.50 (d, J = 2.9 Hz, 1H), 7.25 (dd, J = 2.9 Hz, J = 9.2 Hz, 1H), 7.20 (d, J = 2.9 Hz, 1H), 6.69 (d, J = 5.3 Hz, 1H), 3.77 (s, 2H), 3.40 (t, J = 5.8 Hz, 2H), 3.24 (s, 3H), 2.65 (t, J = 5.8 Hz, 2H), 2.59-2.55 (m, 1H), 0.67-0.66 (m, 2H), 0.44-0.42 (m, 2H)<br>m/z: (M + 2) + 2 /2 262.7 (100%), 263.5 (42%); (M + 1)+ 524.4 (50%), 526.4 (20%) |

TABLE 3-continued

| Cpd | Ex | Structure | Characterization |
|---|---|---|---|
| 400 | 247 | 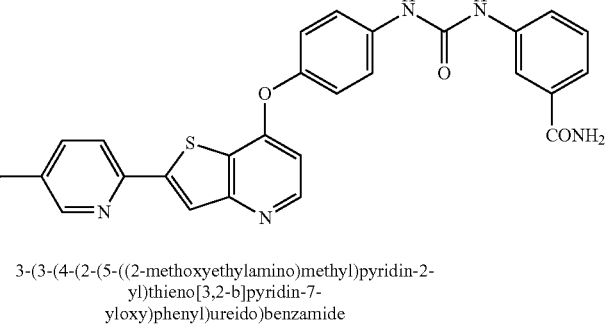<br>3-(3-(4-(2-(5-((2-methoxyethylamino)methyl)pyridin-2-yl)thieno[3,2-b]pyridin-7-yloxy)phenyl)ureido)benzamide | $^1$H NMR (DMSO-d$_6$) δ (ppm): 9.02 (s, 1H), 8.97 (s, 1H), 8.57 (d, J = 1.6 Hz, 1H), 8.51 (d, J = 5.6 Hz, 1H), 8.31 (s, 1H), 8.23 (d, J = 8.0 Hz, 1H), 7.96-7.87 (m, 3H), 7.65 (dd, J = 8.0, 2.0 Hz, 1H), 7.61 (d, J = 8.8 Hz, 2H), 7.47 (d, J = 7.6 Hz, 1H), 7.38-7.31 (m, 2H), 7.26 (d, J = 8.8 Hz, 2H), 6.65 (d, J = 5.6 Hz, 1H), 3.80 (s, 2H), 3.42 (t, J = 5.6 Hz, 2H), 3.24 (s, 3H), 2.67 (t, J = 5.6 Hz, 2H). LRMS(ESI): (calc.) 568.19 (found) 569.5 (MH)+ |
| 401 | 248 | 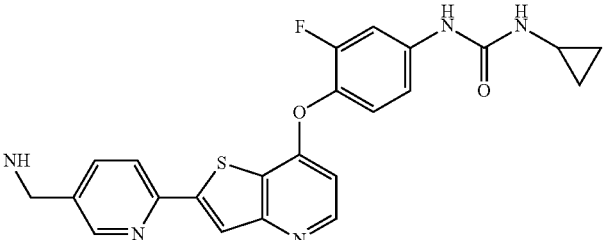<br>1-cyclopropyl-3-(3-fluoro-4-(2-(5-((3-methoxypropylamino)methyl)pyridin-2-yl)thieno[3,2-b]pyridin-7-yloxy)phenyl)urea | $^1$H NMR (DMSO-d$_6$) δ (ppm): 8.77 (s, 1H); 8.63 (d, J = 1.4, 1H); 8.52 (d, J = 5.3, 1H); 8.35 (s, 1H); 8.28 (d, J = 8.0, 1H); 7.97 (dd, J = 8.2, 2.0, 1H); 7.73 (dd, J = 13.7, 2.3, 1H); 7.38 (t, J = 9.2, 1H); 7.20 (d, J = 8.6, 1H); 6.65 (d, J = 5.3, 1H); 6.60 (d, J = 2.4, 1H); 3.94 (s, 2H); 3.38 (t, J = 6.3, 2H); 3.21 (s, 3H); 2.72-2.68 (m, 2H); 2.55 (septet, J = 3.1, 1H); 1.74 (quintet, J = 6.9, 2H); 0.68-0.63 (m, 2H); 0.45-0.40 (m, 2H); LRMS(ESI): (calc.) 521.6 (found) 522.4 (MH)+ |
| 402 | 249 | 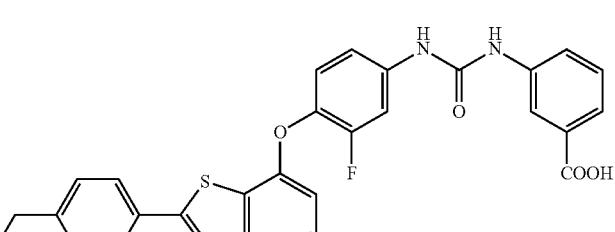<br>3-(3-(3-fluoro-4-(2-(5-((2-methoxyethylamino)methyl)pyridin-2-yl)thieno[3,2-b]pyridin-7-yloxy)phenyl)ureido)benzoic acid | $^1$H NMR (DMSO-d$_6$) δ (ppm): 9.85-9.68 (bs, 1H), 9.68-9.57 (bs, 1H), 8.59 (d, J = 1.2 Hz, 1H), 8.53 (d, J = 5.2 Hz, 1H), 8.33 (s, 1H), 8.25 (d, J = 8.0 Hz, 1H), 8.21 (s, 1H), 8.16 (s, 1H), 7.92 (dd, J = 8.0, 2.0 Hz, 1H), 7.80 (dd, J = 13.2, 2.4 Hz, 1H), 7.69 (d, J = 7.6 Hz, 1H), 7.57 (d, J = 7.6 Hz, 1H), 7.45 (t, J = 9.2 Hz, 1H), 7.40 (t, J = 8.0 Hz, 1H), 7.33 (d, J = 8.4 Hz, 1H), 6.68 (d, J = 5.6 Hz, 1H), 3.84 (s, 2H), 3.43 (t, J = 5.6 Hz, 2H), 3.25 (s, 3H), 2.71 (t, J = 5.6 Hz, 2H). LRMS(ESI): (calc.) 587.16 (found) 588.5 (MH)+ |

| Cpd | Ex | Structure | Characterization |
|---|---|---|---|
| 403 | 250 | 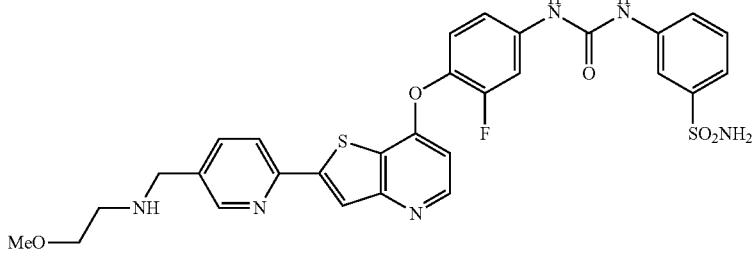<br>3-(3-(3-fluoro-4-(2-(5-((2-methoxyethylamino)methyl)pyridin-2-yl)thieno[3,2-b]pyridin-7-yloxy)phenyl)ureido)benzenesulfonamide | $^1$H NMR (DMSO-$d_6$) δ (ppm): 9.27 (s, 1H); 9.24 (s, 1H); 8.57 (d, J = 1.6, 1H); 8.53 (d, J = 5.5, 1H); 8.32 (s, 1H); 8.23 (d, J = 8.2, 1H); 8.09 (s, 1H); 7.89 (dd, J = 8.0, 2.0, 1H); 7.77 (dd, J = 13.1, 2.3, 1H); 7.58 (d, J = 8.0, 1H); 7.52-7.44 (m, 3H); 7.38 (s, 2H); 7.38-7.31 (m, 1H); 6.67 (d, J = 5.5, 1H); 3.78 (s, 2H); 3.41 (t, J = 5.7, 2H); 3.24 (s, 3H); 2.65 (t, J = 5.7, 2H); 2.33 (br s, 1H).<br>LRMS(ESI): (calc.) 622.7 (found) 623.3 (MH)+ |
| 404 | 251 | 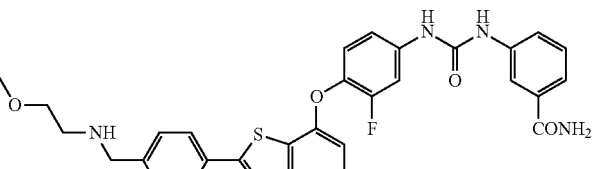<br>3-(3-(4-(2-(5-5,8,11-trioxa-2-azadodecylpyridin-2-yl)thieno[3,2-b]pyridin-7-yloxy)-3-fluorophenyl)ureido)benzamide | $^1$H NMR (DMSO-$d_6$) δ (ppm): 9.35 (s, 1H); 9.12 (s, 1H); 8.60 (d, J = 1.5, 1H); 8.53 (d, J = 5.5, 1H); 8.33 (s, 1H); 8.25 (d, J = 8.0, 1H); 7.94 (s, 1H); 7.91 (s, 2H); 7.77 (dd, J = 13.3, 2.5, 1H); 7.64 (dd, J = 8.0, 1.4, 1H); 7.49-7.43 (m, 2H); 7.38-7.33 (m, 2H); 7.29-7.26 (m, 1H); 6.68 (d, J = 5.3, 1H); 3.86 (s, 2H); 3.52-3.49 (m, 6H); 3.43-3.40 (m, 2H); 3.22 (s, 3H); 2.75-2.70 (m, 2H).<br>LRMS(ESI): (calc.) 674.7 (found) 675.5 (MH)+ |
| 405 | 252 | 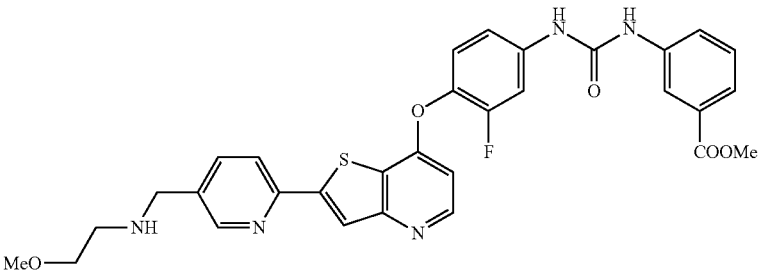 [SMILES: COCCNCc1ccc(-c2cc3nccc(Oc4ccc(NC(=O)Nc5cccc(C(=O)OC)c5)cc4F)c3s2)nc1]<br>methyl 3-(3-(3-fluoro-4-(2-(5-((2-methoxyethylamino)methyl)pyridin-2-yl)thieno[3,2-b]pyridin-7-yloxy)phenyl)ureido)benzoate | $^1$H NMR (DMSO-$d_6$) δ (ppm): 9.14 (s, 1H), 9.12 (s, 1H), 8.57 (d, J = 1.2 Hz, 1H), 8.53 (d, J = 5.6 Hz, 1H), 8.32 (s, 1H), 8.25-8.20 (m, 2H), 7.90 (dd, J = 8.0, 2.0 Hz, 1H), 7.77 (dd, J = 13.2, 2.4 Hz, 1H), 7.68-7.63 (m, 1H), 7.60 (dt, J = 8.0, 1.2 Hz, 1H), 7.49-7.42 (m, 2H), 7.32-7.27 (m, 1H), 6.67 (d, J = 5.6 Hz, 1H), 3.86 (s, 3H), 3.78 (s, 2H), 3.41 (t, J = 5.6 Hz, 2H), 3.24 (s, 3H), 2.65 (t, J = 5.6 Hz, 2H), 2.32 (bs, 1H).<br>LRMS(ESI): (calc.) 601.18 (found) 602.5 (MH)+ |

TABLE 3-continued

| Cpd | Ex | Structure | Characterization |
|---|---|---|---|
| 406 | 253 | 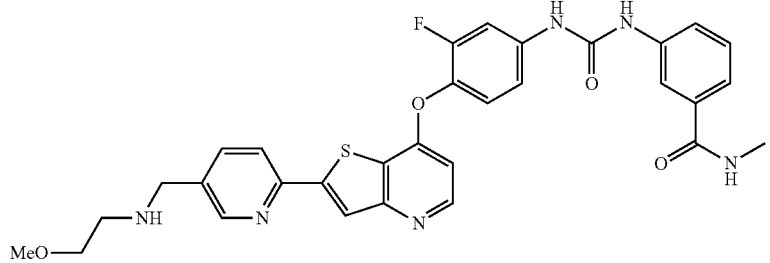 [SMILES: CNC(=O)c1cccc(NC(=O)Nc2ccc(Oc3ccnc4cc(-c5ccc(CNCCOC)cn5)sc34)c(F)c2)c1]<br>3-(3-(3-fluoro-4-(2-(5-((2-methoxyethylamino)methyl)pyridin-2-yl)thieno[3,2-b]pyridin-7-yloxy)phenyl)ureido)-N-methylbenzamide | $^1$H NMR (DMSO-d$_6$) δ (ppm): 9.16 (s, 1H), 9.03 (s, 1H), 8.61 (d, J = 2.0 Hz, 1H), 8.53 (d, J = 5.9 Hz, 1H), 8.44-8.40 (m, 1H), 8.36 (s, 1H), 8.27 (d, J = 8.3 Hz, 1H), 7.96-90 (m, 2H), 7.78 (dd, J = 13.2, 2.4 Hz, 1H), 7.62 (d, J = 6.8 Hz, 1H), 7.49-7.42 (m, 2H), 7.37 (t, J = 7.8 Hz, 1H), 7.28 (d, J = 8.8 Hz, 1H), 6.68 (d, J = 5.4 Hz, 1H), 3.89 (s, 2H), 3.45 (t, J = 5.4 Hz, 2H), 3.26 (s, 3H), 2.89-2.75 (m, 5H).<br>LRMS(ESI): (calc.) 600.20 (found) 601.5 (MH)+ |
| 407 | 254 | 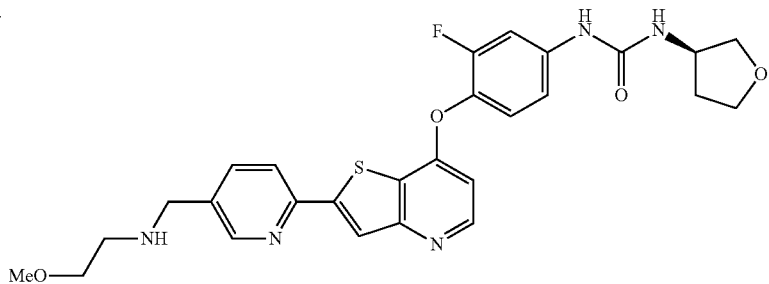 [SMILES: COCCNCc1ccc(-c2cc3nccc(Oc4ccc(NC(=O)N[C@@H]5CCOC5)cc4F)c3s2)nc1]<br>(R)-1-(3-fluoro-4-(2-(5-((2-methoxyethylamino)methyl)pyridin-2-yl)thieno[3,2-b]pyridin-7-yloxy)phenyl)-3-(tetrahydrofuran-3-yl)urea | $^1$H NMR (DMSO-d$_6$) δ (ppm): 8.83 (s, 1H), 8.69 (d, J = 2.0 Hz, 1H), 8.53 (d, J = 5.4 Hz, 1H), 8.41 (s, 1H), 8.34 (d, J = 8.3 Hz, 1H), 8.04 (dd, J = 8.3, 2.4 Hz, 1H), 7.72 (dd, J = 13.7, 2.4 Hz, 1H), 7.39 (t, J = 9.3 Hz, 1H), 7.18-7.14 (m, 1H), 6.69-6.64 (m, 2H), 4.25-4.18 (m, 1H), 4.16 (s, 2H), 3.83-3.68 (m, 3H), 3.55 (t, J = 5.4 Hz, 2H), 3.50 (dd, J = 8.8, 3.4 Hz, 1H), 3.30 (s, 3H), 3.08-3.02 (m, 2H), 2.18-2.09 (m, 1H), 1.78-1.70 (m, 1H) (presumably a mono-TFA salt)<br>LRMS(ESI): (calc.) 537.2 (found) 538.3 (MH)+ |
| 408 | 255 | 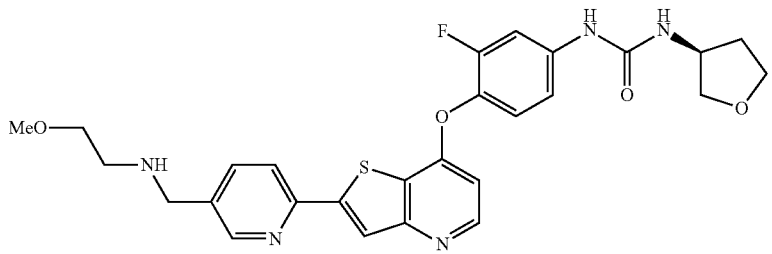 [SMILES: COCCNCc1ccc(-c2cc3nccc(Oc4ccc(NC(=O)N[C@H]5CCOC5)cc4F)c3s2)nc1]<br>(S)-1-(3-fluoro-4-(2-(5-((2-methoxyethylamino)methyl)pyridin-2-yl)thieno[3,2-b]pyridin-7-yloxy)phenyl)-3-(tetrahydrofuran-3-yl)urea | (DMSO-d6) d (ppm) 1H: 8.77 (s, 1H); 8.57 (s, 1H); 8.51 (d, J = 5.4, 1H); 8.31 (s, 1H); 8.22 (d, J = 8.3, 1H); 7.89 (dd, J = 8.3, 1.5, 1H); 7.70 (dd, J = 13.7, 2.4, 1H); 7.38 (t, J = 8.8, 1H); 7.17-7.14 (m, 1H); 6.64 (d, J = 5.4, 1H); 6.61 (s, 1H); 4.23-4.21 (m, 1H); 3.82-3.68 (m, 3H); 3.79 (s, 2H); 3.54-3.48 (m, 1H); 3.41 (t, J = 5.4, 2H); 3.24 (s, 3H); 2.66 (t, J = 5.4, 2H); 2.16-2.11 (m, 1H); 1.76-1.72 (m, 1H).<br>LRMS(ESI): (calc.) 537.2 (found) 538.4 (MH)+ |

TABLE 3-continued

| Cpd | Ex | Structure | Characterization |
|---|---|---|---|
| 409 | 256 | 3-(3-(3-fluoro-4-(2-(5-((N-(2-methoxyethyl)acetamido)methyl)pyridin-2-yl)thieno[3,2-b]pyridin-7-yloxy)phenyl)ureido)benzamide | $^1$H NMR (DMSO-d$_6$) δ (ppm): 9.09 (s, 1H), 8.93 (s, 1H), 8.60-8.48 (m, 2H), 8.40-8.18 (m, 2H), 7.92 (bs, 2H), 7.84-7.73 (m, 2H), 7.64 (d, J = 7.3 Hz, 1H), 7.49 (d, J = 7.3 Hz, 1H), 7.45 (t, J = 9.0 Hz, 1H), 7.37 (d, J = 7.8 Hz, 1H), 7.33 (s, 1H), 7.28 (d, J = 8.3 Hz, 1H), 6.73-6.64 (m, 1H), 4.71 and 4.59 (2s, 2H), 3.55-3.40 (m, 4H), 3.24 and 3.21 (2s, 3H), 2.13 and 2.05 (2s, 3H). LRMS(ESI): (calc.) 628.67 (found) 629.5 (MH)+ |
| 410 | 257 | N-((6-(7-(4-(3-cyclopropylureido)-2-fluorophenoxy)thieno[3,2-b]pyridin-2-yl)pyridin-3-yl)methyl)-N-(2,5,8,11-tetraoxatridecan-13-yl)acetamide | $^1$H NMR (DMSO-d$_6$) δ (ppm): 8.74 (s, 1H); 8.53-8.50 (m, 2H); 8.34 (s, 0.3H), 8.31 (s, 0.7H); 8.27 (d, J = 8.3, 0.3H); 8.21 (d, J = 8.3, 0.7H); 7.80-7.70 (m, 2H), 7.37 (t, J = 8.8, 1H), 7.20 (d, J = 8.8, 1H); 6.66-6.63 (m, 2H), 6.59 (s, 1H); 4.75 (s, 0.6H); 4.60 (s, 1.4H); 3.55-3.45 (m, 14H); 3.40 (t, J = 4.9, 2H); 3.21 (s, 3H); 2.56-2.50 (m, 1H); 2.14 (s, 2.2H); 2.06 (s, 0.8H); 0.67-0.64 (m, 2H); 0.44-0.40 (m, 2H). Mixture of rotamers, 7:3 by 1H NMR. LRMS(ESI): (calc.) 681.8 (found) 704.5 (MNa)+ |
| 411 | 258 | 1-(3-fluoro-4-(2-(5-((2-methoxyethylamino)methyl)pyridin-2-yl)thieno[3,2-b]pyridin-7-yloxy)phenyl)-3-(1-methyl-1H-pyrazol-3-yl)urea | $^1$H NMR (DMSO-d$_6$) δ (ppm): 9.32 (bs, 1H), 9.07 (s, 1H), 8.57 (d, J = 1.4 Hz, 1H), 8.52 (d, J = 5.5 Hz, 1H), 8.32 (s, 1H), 8.23 (d, J = 8.1 Hz, 1H), 7.90 (dd, J = 8.1, 2.2 Hz, 1H), 7.78 (dd, J = 13.3, 2.5 Hz, 1H), 7.55 (d, J = 2.3 Hz, 1H), 7.44 (t, J = 9.0 Hz, 1H), 7.27-7.23 (m, 1H), 6.66 (dd, J = 5.5, 0.8 Hz, 1H), 6.23 (d, J = 2.2, 1H), 3.79 (s, 2H), 3.74 (s, 3H), 3.41 (t, J = 5.7 Hz, 2H), 3.32 (s, 1H), 3.24 (s, 3H), 2.66 (t, J = 5.7 Hz, 2H). LRMS(ESI): (calc.) 547.6 (found) 548.4 (MH)+ |

TABLE 3-continued

| Cpd | Ex | Structure | Characterization |
|---|---|---|---|
| 412 | 259 | 3-(3-(3-fluoro-4-(2-(5-((2-methoxyethylamino)methyl)pyridin-2-yl)thieno[3,2-b]pyridin-7-yloxy)phenyl)ureido)-N,N-dimethylbenzamide | $^1$H NMR (DMSO-d$_6$) δ (ppm): 9.17 (s, 1H), 9.00 (s, 1H), 8.58 (d, J = 1.2 Hz, 1H), 8.53 (d, J = 5.8 Hz, 1H), 8.33 (s, 1H), 8.24 (d, J = 8.0 Hz, 1H), 7.90 (dd, J = 8.0, 2.0 Hz, 1H), 7.76 (dd, J = 13.2, 2.4 Hz, 1H), 7.58 (t, J = 1.2 Hz, 1H), 7.48-7.42 (m, 2H), 7.35 (t, J = 8.0 Hz, 1H), 7.28 (dt, J = 8.8, 1.2 Hz, 1H), 7.01 (dt, J = 7.6, 1.2 Hz, 1H), 6.67 (dd, J = 5.6, 0.8 Hz, 1H), 3.79 (s, 2H), 3.41 (t, J = 5.6 Hz, 2H), 3.24 (s, 3H), 2.99 (s, 3H), 2.92 (s, 3H), 2.66 (t, J = 5.6 Hz, 2H). LRMS(ESI): (calc.) 614.21 (found) 615.5 (MH)+ |
| 413 | 260 | N-((6-(7-(2-fluoro-4-(3-(3-(methylsulfonyl)phenyl)ureido)phenoxy)thieno[3,2-b]pyridin-2-yl)pyridin-3-yl)methyl)-N-(2-methoxyethyl)acetamide | $^1$H NMR (DMSO-d$_6$) δ (ppm): mixture of rotamers, 9.30 (bs, 1H), 9.23 (bs, 1H), 8.56-8.49 (m, 2H), 8.37 and 8.33 (2s, 1H), 8.29 and 8.23 (2d, J = 8.2 Hz, 1H), 8.18 (t, J = 1.8 Hz, 1H), 7.82-7.67 (m, 3H), 7.62-7.52 (m, 2H), 7.47 (t, J = 9.0 Hz, 1H), 7.34-7.28 (m, 1H), 6.71-6.66 (m, 1H), 4.71 and 4.59 (2s, 2H), 3.53-3.41 (m, 4H), 3.24 (s, 3H), 3.21 (s, 3H), 2.13 and 2.05 (2s, 3H). LRMS(ESI): (calc.) 663.74 (found) 664.4 (MH)+ |
| 414 | 261 | 1-cyclobutyl-3-(3-fluoro-4-(2-(5-((2-methoxyethylamino)methyl)pyridin-2-yl)thieno[3,2-b]pyridin-7-yloxy)phenyl)urea | $^1$H NMR (DMSO-d$_6$) δ (ppm): 8.77 (s, 1H), 8.56 (d, J = 1.8 Hz, 1H), 8.51 (d, J = 5.3 Hz, 1H), 8.28 (s, 1H), 8.20 (d, J = 7.9 Hz, 1H), 7.89 (dd, J = 1.9 Hz, J = 8.2 Hz, 1H), 7.68 (dd, J = 2.3 Hz, J = 10.1 Hz, 1H), 7.36 (t, J = 10.1 Hz, 1H), 7.15 (m, 1H), 6.36 (d, J = 5.4 Hz, 1H), 6.60 (J = 7.8 Hz, 1H), 4.13 (m, 1H), 3.77 (s, 2H), 3.52 (t, J = 5.5 Hz, 2H), 3.23 (s, 3H), 3.20 (t, J = 5.5 Hz, 2H), 2.22-2.17 (m, 2H), 1.89-1.85 (m, 2H), 1.64-1.58 (m, 2H) m/z: (M + 2) + 2 /2 261.7 (100%), (M + 1)+ 522.5 (5%). |

| Cpd | Ex | Structure | Characterization |
|---|---|---|---|
| 415 | 262 | 3-(3-(3-fluoro-4-(2-(5-((N-(2-methoxyethyl)acetamido)methyl)pyridin-2-yl)thieno[3,2-b]pyridin-7-yloxy)phenyl)ureido)-N,N-dimethylbenzamide | $^1$H NMR (DMSO-$d_6$) δ (ppm): (mixture of rotamers) 9.12 (s, 1H), 8.95 (s, 1H), 8.56-8.48 (m, 2H), 8.38-8.26 (m, 2H), 8.23 (d, J = 8.0 Hz, 1H), 7.82-7.72 (m, 3H), 7.58 (s, 1H), 7.50-7.41 (m, 2H), 7.36 (t, J = 8.0 Hz, 1H), 7.28 (d, J = 8.8 Hz, 1H), 7.01 (d, J = 7.2 Hz, 1H), 6.68 (d, J = 5.6 Hz, 1H), 4.71 and 4.59 (2s, 2H), 3.53-3.40 (m, 4H), 3.24 and 3.21 (2s, 3H), 2.98 and 2.93 (2s, 6H), 2.13 and 2.05 (2s, 3H). LRMS(ESI): (calc.) 656.22 (found) 657.6 (MH)+ |
| 416 | 263 | 1-(3-fluoro-4-(2-(5-((2-methoxyethylamino)methyl)pyridin-2-yl)thieno[3,2-b]pyridin-7-yloxy)phenyl)-3-isopropylurea | $^1$H NMR (DMSO-$d_6$) δ (ppm): 8.90 (s, 1H), 8.55 (d, 1H, J = 1.6 Hz), 8.49 (d, 1H, J = 5.5), 8.29 (s, 1H), 8.20 (d, 1H, J = 8.0 Hz), 7.87 (dd, 1H, J1 = 2.2 Hz, J2 = 8.3 Hz), 7.71 (dd, 1H, J1 = 2.3 Hz, J2 = 3.5 Hz), 7.34 (t, 1H, J = 9.0 Hz), 7.14-7.11 (m, 1H), 6,61 (d, 1H, J = 5.5 Hz), 6.36 (d, 1H, J = 7.4 Hz), 3,76 (m, 3H), 3.39 (t, 2H, J = 5.6 Hz), 3.22 (s, 3H), 2.62 (t, 2H, J = 5.7 Hz), 1.09 (s, 3H), 1.08 (s, 3H). LRMS(ESI): (calc.) 509.2 (found) 510.4 (MH)+ |
| 417 | 264 | 1-(2,4-difluorophenyl)-3-(3-fluoro-4-(2-(5-((2-methoxyethylamino)methyl)pyridin-2-yl)thieno[3,2-b]pyridin-7-yloxy)phenyl)urea | $^1$H NMR (DMSO-$d_6$) δ (ppm): 9.38 (s, 1H), 8.69 (d, 1H, J = 1.6 Hz), 8.62 (dd, 1H, J1 = 0.4 Hz, J2 = 2.3 Hz), 8.53 (d, 1H, J = 5.4 Hz), 8.40 (s, 1H), 8.35 (d, 1H, J = 7.8 Hz), 8.04-7.99 (m, 2H), 7.74 (dd, 1H, J1 = 2.6 Hz, J2 = 13.1 Hz), 7.44 (t, 1H, J = 9.0 Hz), 7.35-7.29 (m, 1H), 7.25-7.22 (m, 1H), 7.08-7.04 (m, 1H), 6,68 (dd, 1H, J1 = 0.8 Hz, J2 = 5.3 Hz), 4.22 (s, 2H), 3.57 (t, 2H, J = 5.2 Hz), 3.30 (s, 3H), 3.12 (m, 2H) (presumably a mono-TFA salt) LRMS(ESI): (calc.) 579.2 (found) 580.4 (MH)+ |

TABLE 3-continued

| Cpd | Ex | Structure | Characterization |
|---|---|---|---|
| 418 | 265 | 1-(4-(2-(5-(1,3-dioxan-2-yl)pyridin-2-yl)thieno[3,2-b]pyridin-7-yloxy)-3-fluorophenyl)-3-cyclopropylurea | $^1$H NMR (DMSO-d$_6$) δ (ppm): 8.78 (s, 1H), 8.65 (d, J = 2.2 Hz, 1H), 8.57 (d, J = 5.7 Hz, 1H), 8.37 (s, 1H), 8.31 (dd, J = 8.2, 0.6 Hz, 1H), 7.94 (dd, J = 8.4, 2.0 Hz, 1H), 7.74 (dd, J = 13.6, 2.4 Hz, 1H), 7.39 (t, J = 9.0 Hz, 1H), 7.21 (bd, J = 9.6 Hz, 1H), 6.72 (d, J = 4.9 Hz, 1H), 6.63-6.57 (m, 1H), 5.68 (s, 1H), 4.23-4.15 (m, 2H), 3.99 (td, J = 12.1, 2.5 Hz, 2H), 2.59-2.52 (m, 1H), 2.11-1.97 (m, 1H), 1.53-1.45 (m, 1H), 0.69-0.62 (m, 2H), 0.46-0.40 (m, 2H). LRMS(ESI): (calc.) 506.55 (found) 507.4 (MH)+ |
| 419 | 266 | methyl (6-(7-(4-(3-(3-carbamoylphenyl)ureido)-2-fluorophenoxy)thieno[3,2-b]pyridin-2-yl)pyridin-3-yl)methyl(2-methoxyethyl)carbamate | $^1$H NMR (DMSO-d$_6$) δ (ppm): 9.11 (s, 1H), 8.95 (s, 1H), 8.53 (d, J = 5.5 Hz, 2H), 8.34 (s, 1H), 8.25 (d, J = 8.2 Hz, 1H), 7.94 (bs, 1H), 7.92 (t, J = 1.9 Hz, 1H), 7.85-7.77 (m, 1H), 7.77 (dd, J = 13.3, 2.5 Hz, 1H), 7.67-7.62 (m, 1H), 7.52-7.42 (m, 2H), 7.37 (t, J = 7.8 Hz, 1H), 7.36 (bs, 1H), 7.31-7.25 (m, 1H), 6.68 (d, J = 5.4 Hz, 1H), 4.54 (s, 2H), 3.64 (bs, 3H), 3.44 (bs, 4H), 3.22 (s, 3H). LRMS(ESI): (calc.) 644.67 (found) 645.5 (MH)+ |
| 420 | 267 | methyl (6-(7-(2-fluoro-4-(3-(3-(methylsulfonyl)phenyl)ureido)phenoxy)thieno[3,2-b]pyridin-2-yl)pyridin-3-yl)methyl(2-methoxyethyl)carbamate | $^1$H NMR (DMSO-d$_6$) δ (ppm): 9.28 (s, 1H), 9.20 (s, 1H), 8.54 (d, J = 5.5 Hz, 2H), 8.35 (s, 1H), 8.25 (d, J = 8.2 Hz, 1H), 8.18 (t, J = 1.8 Hz, 1H), 7.86-7.77 (m, 1H), 7.77 (dd, J = 13.3, 2.5 Hz, 1H), 7.73-7.67 (m, 1H), 7.59 (t, J = 7.7 Hz, 1H), 7.55 (tt, J = 7.6, 1.6 Hz, 1H), 7.47 (t, J = 9.0 Hz, 1H), 7.34-7.28 (m, 1H), 6.68 (d, J = 5.3 Hz, 1H), 4.54 (s, 2H), 3.64 (bs, 3H), 3.44 (bs, 4H), 3.22 and 3.21 (2s, 6H). LRMS(ESI): (calc.) 679.74 (found) 680.3 |

TABLE 3-continued

| Cpd | Ex | Structure | Characterization |
|---|---|---|---|
| 421 | 268 | 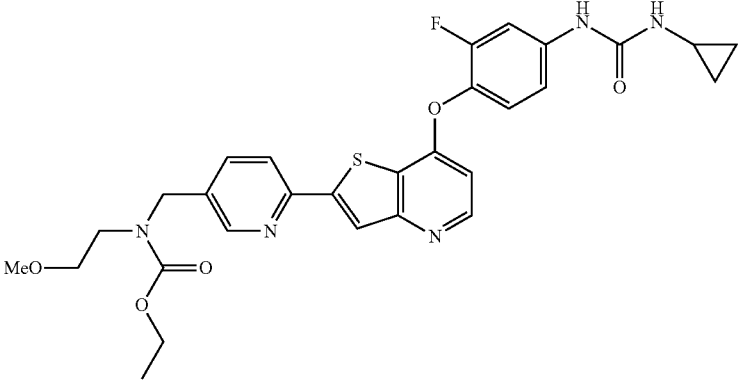 [SMILES: CCOC(=O)N(CCOC)Cc1ccc(-c2cc3nccc(Oc4ccc(NC(=O)NC5CC5)cc4F)c3s2)nc1]<br>ethyl (6-(7-(4-(3-cyclopropylureido)-2-fluorophenoxy)thieno[3,2-b]pyridin-2-yl)pyridin-3-yl)methyl(2-methoxyethyl)carbamate | $^1$H NMR (DMSO-d$_6$) δ (ppm): 8.70 (s, 1H), 8.54 (s, 1H), 8.52 (d, J = 5.6 Hz, 1H), 8.33 (s, 1H), 8.25 (d, J = 8.4 Hz, 1H), 7.81 (d, J = 8.0, 1H), 7.73 (dd, J = 13.6, 2.8 Hz, 1H), 7.38 (t, J = 8.8 Hz, 1H), 7.20 (d, J = 8.6 Hz, 1H), 6.64 (dd, J = 5.2, 0.8 Hz, 1H), 6.57 (d, J = 2.4 Hz, 1H), 4.53 (s, 2H), 4.13-4.03 (m, 2H), 3.45 (s, 4H), 3.22 (s, 3H), 2.59-2.52 (m, 1H), 1.26-1.08 (m, 3H), 0.69-0.62 (m, 2H), 0.46-0.40 (m, 2H).<br>LRMS(ESI): (calc.) 579.20 (found) 580.5 (MH)+ |
| 422 | 269 | 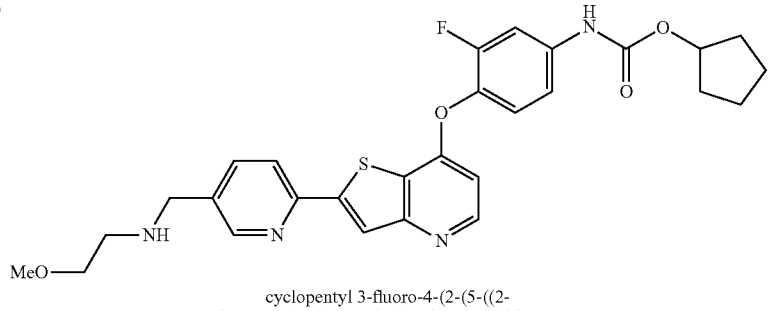<br>cyclopentyl 3-fluoro-4-(2-(5-((2-methoxyethylamino)methyl)pyridin-2-yl)thieno[3,2-b]pyridin-7-yloxy)phenylcarbamate | $^1$H NMR (DMSO-d$_6$) δ (ppm): 9.98 (s, 1H), 8.63 (s, 1H), 8.52 (d, J = 4.9 Hz, 1H), 8.36 (s, 1H), 8.28 (d, J = 7.8 Hz, 1H), 7.97 (d, J = 8.3 Hz, 1H), 7.65 (d, J = 12.5 Hz, 1H), 7.45 (t, J = 9.1 Hz, 1H), 7.34 (d, J = 9.1 Hz, 1H), 6.65 (d, J = 5.8 Hz, 1H), 5.12 (s, 1H), 3.98 (s, 2H), 3.50-3.48 (m, 2H), 3.27 (s, 3H), 2.87 (m, 2H), 1.89-1.88 (m, 2H), 1.70-1.60 (m, 6H)<br>m/z: (M + 2) + 2 /2 269.2 (100%), (M + 1)+ 537.5 (9%) |
| 423 | 270 | 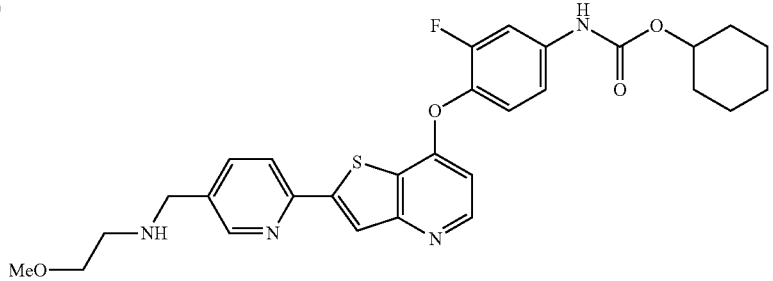 [SMILES: COCCNCc1ccc(-c2cc3nccc(Oc4ccc(NC(=O)OC5CCCCC5)cc4F)c3s2)nc1]<br>cyclohexyl 3-fluoro-4-(2-(5-((2-methoxyethylamino)methyl)pyridin-2-yl)thieno[3,2-b]pyridin-7-yloxy)phenylcarbamate | $^1$H NMR (DMSO-d$_6$) δ (ppm): 10.01 (s, 1H), 8.58 (s, 1H), 8.51 (d, J = 5.3 Hz, 1H), 8.32 (s, 1H), 8.24 (d, J = 8.0 Hz, 1H), 7.92 (m, 1H), 7.64 (m, 1H), 7.55 (t, J = 9.1 Hz, 1H), 7.38 (d, J = 8.3 Hz, 1H), 6.65 (d, 1H), 4.65 (m, 1H), 3.84 (m, 2H), 3.44 (m, 2H), 3.24 (s, 3H), 2.72 (m, 2H), 1.89 (m 2H), 1.72 (m, 2H), 1.51 (m, 1H), 1.43-1.39 (m, 4H), 1.22 (m, 1H)<br>m/z: (M + 2) + 2 /2 276.2 (100%), (M + 1)+ 551.5 (31%) |

| Cpd | Ex | Structure | Characterization |
|---|---|---|---|
| 424 | 271 | 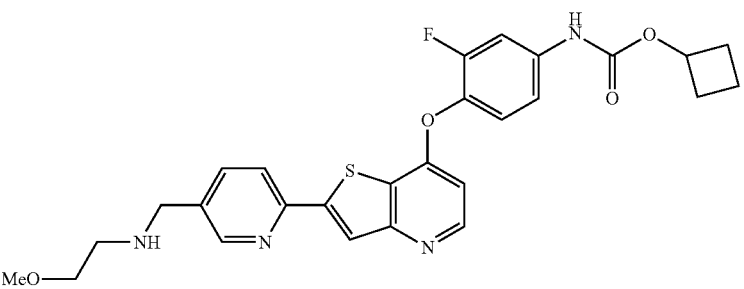 [SMILES: COCCNCc1ccc(-c2cc3nccc(Oc4ccc(NC(=O)OC5CCC5)cc4F)c3s2)nc1]<br>cyclobutyl 3-fluoro-4-(2-(5-((2-methoxyethylamino)methyl)pyridin-2-yl)thieno[3,2-b]pyridin-7-yloxy)phenylcarbamate | $^1$H NMR (DMSO-d$_6$) δ (ppm): 10.08 (s, 1H), 8.57 (s, 1H), 8.30 (s, 1H), 8.22 (d, J = 5.4 Hz, 1H), 8.30 (s, 1H), 8.22 (d, J = 8.2 Hz, 1H), 7.62 (d, J = 13.0 Hz, 1H), 7.44 (t, J = 8.7 Hz, 1H), 7.32 (d, J = 8.7 Hz, 1H), 6.63 (d, J = 5.4 Hz, 1H), 4.94 (m, 1H), 3.83 (s, 2H), 3.42 (t, J = 5.9 Hz, 2H), 3.23 (s, 3H), 2.70 (t, J = 5.9 Hz, 2H), 2.30 (m, 2H), 2.09-2.01 (m, 2H), 1.78-1.71 (m, 1H), 1.62-1.57 (m, 1H)<br>m/z: (M + 2) + 2 /2 262.2 (100%), (M + 1)+ 523.4 (31%) |
| 425 | 272 | 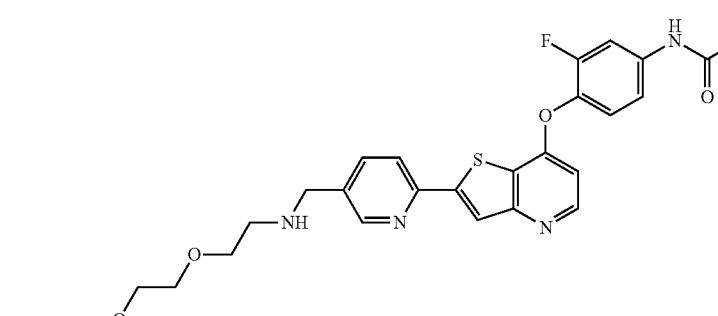<br>N-(4-(2-(5-5,8,11-trioxa-2-azadodecylpyridin-2-yl)thieno[3,2-b]pyridin-7-yloxy)-3-fluorophenyl)-N-(4-fluorophenyl)cyclopropane-1,1-dicarboxamide<br>$^1$H NMR (DMSO-d$_6$) δ (ppm): 10.39 (s, 1H); 10.00 (s, 1H); 8.55 (d, J = 1.6, 1H); 8.50 (d, J = 5.3, 1H); 8.31 (s, 1H); 8.22-8.18 (m, 1H); 7.91-7.86 (m, 2H); 7.64-7.60 (m, 2H); 7.51-7.42 (m, 2H); 7.17-7.11 (m, 2H); 6.63 (s, J = 5.5, 1H); 3.77 (s, 2H); 3.50-3.43 (m, 6H); 3.49 (s, 3H); 3.39-3.37 (m, 2H); 2.66-2.62 (m, 2H); 1.45 (s, 4H).<br>LRMS(ESI): (calc.) 717.8 (found) 718.5 (MH)+ | |
| 426 | 273 | 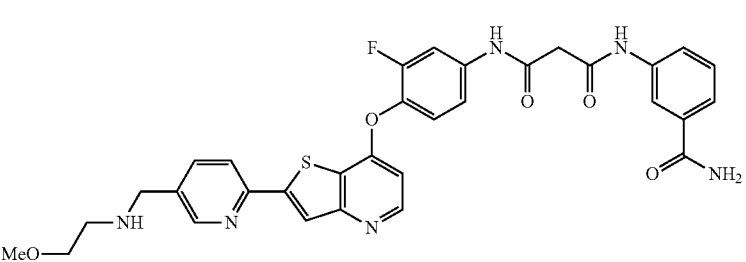 [SMILES: COCCNCc1ccc(-c2cc3nccc(Oc4ccc(NC(=O)CC(=O)Nc5cccc(C(N)=O)c5)cc4F)c3s2)nc1]<br>N1-(3-carbamoylphenyl)-N3-(3-fluoro-4-(2-(5-((2-methoxyethylamino)methyl)pyridin-2-yl)thieno[3,2-b]pyridin-7-yloxy)phenyl)malonamide | $^1$H NMR (DMSO-d$_6$) δ (ppm): 10.62 (s, 1H), 10.37 (s, 1H), 8.71 (d, J = 1.6 Hz, 1H), 8.42 (s, 1H), 8.36 (d, J = 7.6 Hz, 1H), 8.09-8.05 (m, 2H), 7.96 (s, 1H), 7.90 (dd, J = 12.8, 2.0 Hz, 1H), 7.81-7.76 (m, 1H), 7.56 (d, J = 8.0 Hz, 1H), 7.51 (t, J = 8.4 Hz, 1H), 7.46 (dd, J = 9.2, 2.0 Hz, 1H), 7.40 (t, J = 8.0 Hz, 1H), 7.36 (s, 1H), 6.71 (d, J = 5.2 Hz, 1H), 4.22 (s, 2H), 3.59 (t, J = 5.2 Hz, 2H), 3.54 (s, 2H), 3.31 (s, 3H), 3.14-3.08 (m, 2H) (presumably a mono-TFA salt).<br>LRMS(ESI): (calc.) 628.19 (found) 629.5 (MH)+ |

TABLE 3-continued

| Cpd | Ex | Structure | Characterization |
|---|---|---|---|
| 427 | 274 | 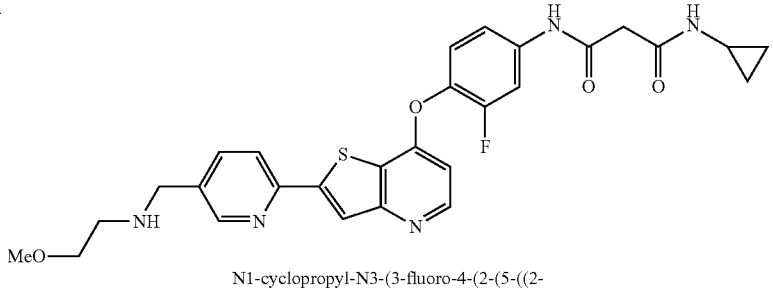<br>N1-cyclopropyl-N3-(3-fluoro-4-(2-(5-((2-methoxyethylamino)methyl)pyridin-2-yl)thieno[3,2-b]pyridin-7-yloxy)phenyl)malonamide | $^1$H NMR (DMSO-$d_6$) δ (ppm): 10.11 (s, 1H), 8.16 (d, 1H, J = 1.4 Hz), 8.10 (d, 1H, J = 5.3 Hz), 7.91 (s, 1H), 7.83-7.81 (m, 2H), 7.50-7.44 (m, 2H) 7.08 (t, 1H, J = 9.0 Hz), 7.06-7.00 (m, 1H), 6.26 (d, 1H, J = 5.5 Hz), 3.37 (s, 2H), 3.00 (t, 2H, J = 5.7 Hz), 2.88 (s, 3H), 2.81 (s, 2H), 2.24 (t, 2H, J = 4.5 Hz), 0.24-0.22 (m, 2H), 0.03-0.01 (m, 2H). LRMS(ESI): (calc.) 549.1 (found) 550.4 (MH)+ |
| 428 | 275 | 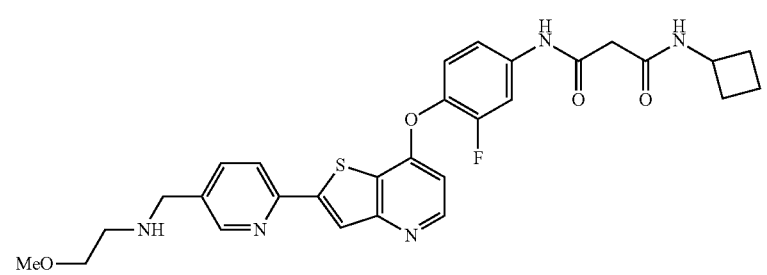 [SMILES: COCCNCc1ccc(-c2cc3nccc(Oc4ccc(NC(=O)CC(=O)NC5CCC5)cc4F)c3s2)nc1]<br>N1-cyclobutyl-N3-(3-fluoro-4-(2-(5-((2-methoxyethylamino)methyl)pyridin-2-yl)thieno[3,2-b]pyridin-7-yloxy)phenyl)malonamide | $^1$H NMR (DMSO-$d_6$) δ (ppm): 10.50 (s, 1H), 8.57 (s, 1H), 8.52 (d, 1H, J = 5.4 HZ), 8.40 (d, 1H, J = 7.8 Hz), 8.33 (s, 1H), 8.24 (d, 1H, J = 8.2 Hz), 7.91-7.68 (m, 2H), 7.49 (t, 1H, J = 9.0 Hz), 7.42 (d, 1H, J = 8.2 Hz), 6.67 (d, 1H, J = 4.9 Hz), 4.20 (m, 1H), 3.78 (s, 2H), 3.41 (t, 2H), 3.24 (s, 3H), 3.23 (s, 2H), 2.65 (t, 3H), 2.17 (m, 2H), 1.90 (m, 2H), 1.64 (m, 2H). LRMS(ESI): (calc.) 563.2 (found) 564.5 (MH)+ |
| 429 | 276 | 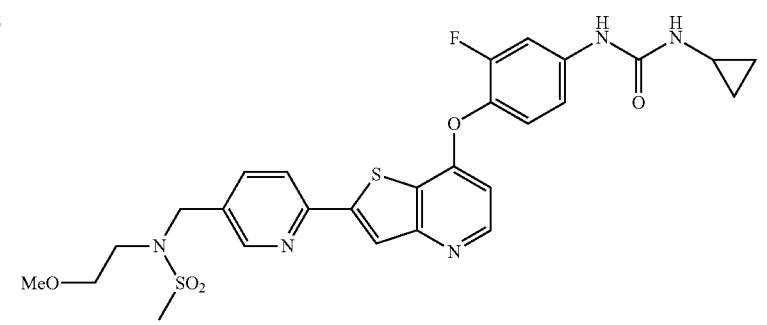 [SMILES: COCCN(Cc1ccc(-c2cc3nccc(Oc4ccc(NC(=O)NC5CC5)cc4F)c3s2)nc1)S(C)(=O)=O]<br>N-((6-(7-(4-(3-cyclopropylureido)-2-fluorophenoxy)thieno[3,2-b]pyridin-2-yl)pyridin-3-yl)methyl)-N-(2-methoxyethyl)methanesulfonamide | $^1$H NMR (DMSO-$d_6$) δ (ppm): 8.71 (s, 1H), 8.61 (d, J = 1.2 Hz, 1H), 8.52 (d, J = 5.6 Hz, 1H), 8.35 (s, 1H), 8.30 (d, J = 8.0 Hz, 1H), 7.91 (dd, J = 8.0, 2.0 Hz, 1H), 7.73 (dd, J = 13.6, 2.4 Hz, 1H), 7.38 (t, J = 8.8 Hz, 1H), 7.20 (d, J = 8.8 Hz, 1H), 6.65 (dd, J = 5.6, 0.8 Hz, 1H), 6.57 (d, J = 2.0 Hz, 1H), 4.48 (s, 2H), 3.43 (t, J = 5.6 Hz, 2H), 2.38-3.30 (m, 2H, hidden under water peak), 3.20 (s, 3H), 3.06 (s, 3H), 2.59-2.52 (m, 1H), 0.69-0.62 (m, 2H), 0.46-0.40 (m, 2H). LRMS(ESI): (calc.) 585.15 (found) 586.55 (MH)+ |

| Cpd | Ex | Structure | Characterization |
|---|---|---|---|
| 430 | 277 | 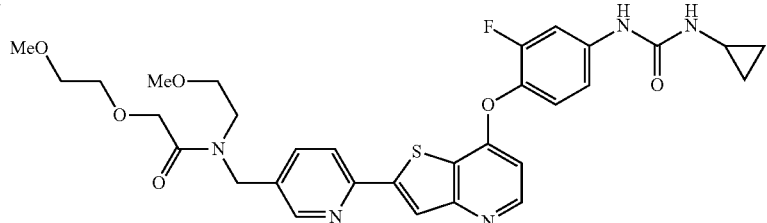<br>N-((6-(7-(4-(3-cyclopropylureido)-2-fluorophenoxy)thieno[3,2-b]pyridin-2-yl)pyridin-3-yl)methyl)-2-(2-methoxyethoxy)-N-(2-methoxyethyl)acetamide | $^1$H NMR (DMSO-$d_6$) δ (ppm): 8.76 (s, 1H); 8.54-8.51 (m, 2H); 8.36 (s, 0.3H); 8.32 (s, 0.7H); 8.28 (d, J = 8.2, 0.3H); 8.23 (d, J = 8.2, 0.7H); 7.84-7.76 (m, 1H); 7.72 (dd, J = 13.5, 2.5, 1H); 7.36 (t, J = 9.0, 1H); 7.20 (d, J = 9.0, 1H); 6.65-6.60 (m, 2H); 4.67 (s, 0.6H); 4.61 (s, 1.4H); 4.31 (s, 1.5H); 4.21 (s, 0.5H); 3.60-3.15 (m, 14H); 2.55 (septet, J = 3.5, 1H); 0.68-0.62 (m, 2H); 0.45-0.41 (m, 2H). (mixture of two rotamers, approx 7:3 ratio by NMR. LRMS(ESI): (calc.) 623.2 (found) 624.5 (MH)+ |
| 431 | 278 | 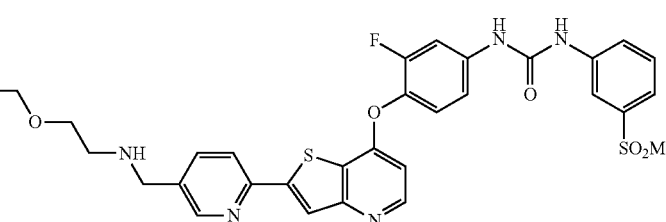<br>1-(4-(2-(5-5,8,11,14-tetraoxa-2-azapentadecylpyridin-2-yl)thieno[3,2-b]pyridin-7-yloxy)-3-fluorophenyl)-3-(3-(methylsulfonyl)phenyl)urea<br>$^1$H NMR (DMSO-$d_6$) δ (ppm): 9.34 (s, 1H), 9.26 (s, 1H), 8.58 (d, J = 1.4 Hz, 1H), 8.53 (d, J = 5.5 Hz, 1H), 8.32 (s, 1H), 8.24 (d, J = 8.0 Hz, 1H), 8.18 (t, J = 1.9 Hz, 1H), 7.90 (dd, J = 8.2, 2.2 Hz, 1H), 7.77 (dd, J = 13.3, 2.4 Hz, 1H), 7.70 (dt, J = 8.4, 1.8 Hz, 1H), 7.59 (t, J = 7.7 Hz, 1H), 7.55 (dt, J = 7.6, 1.5 Hz, 1H), 7.47 (t, J = 9.0 Hz, 1H), 7.34-7.28 (m, 1H), 6.67 (dd, J = 5.5, 0.8 Hz, 1H), 3.80 (s, 2H), 3.54-3.46 (m, 12H), 3.42-3.38 (m, 2H), 3.31 (bs, 1H), 3.21 and 3.208 (2s, 6H), 2.66 (t, J = 5.7 Hz, 2H).<br>LRMS(ESI): (calc.) 753.86 (found) 754.7 (MH)+ | |
| 432 | 279 | 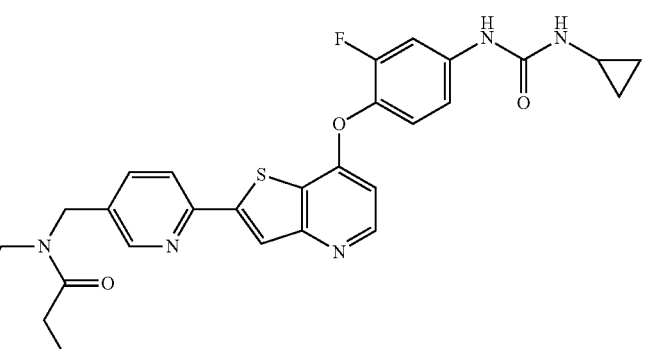<br>N-((6-(7-(4-(3-cyclopropylureido)-2-fluorophenoxy)thieno[3,2-b]pyridin-2-yl)pyridin-3-yl)methyl)-2-hydroxy-N-(2-methoxyethyl)acetamide | $^1$H NMR (DMSO-$d_6$) δ (ppm): (mixture of rotamers), 8.69 (s, 1H), 8.53-8.48 (m, 2H), 8.34 and 8.31 (2s, 1H), 8.27 and 8.22 (2d, J = 8.0 Hz, 1H), 7.81-7.74 (m, 1H), 7.71 (dd, J = 13.2, 2.4 Hz, 1H), 7.36 (t, J = 9.2 Hz, 1H), 7.18 (d, J = 8.8 Hz, 1H), 6.62 (d, J = 4.8 Hz, 1H), 6.56 (d, J = 2.0 Hz, 1H), 4.80-4.58 (m, 3H), 4.22 and 4.12 (2d, J = 5.6 Hz, 2H), 3.49-3.38 (m, 4H), 3.21 and 3.19 (2s, 3H), 2.57-2.50 (m, 1H), 0.67-0.60 (m, 2H), 0.44-0.38 (m, 2H). LRMS(ESI): (calc.) 565.18 (found) 566.5 (MH)+ |

Additional compounds according to the present invention include those in Table 4.

TABLE 4

| Cpd | Ex | Structure and Characterization |
|---|---|---|
| 433 | 280 | 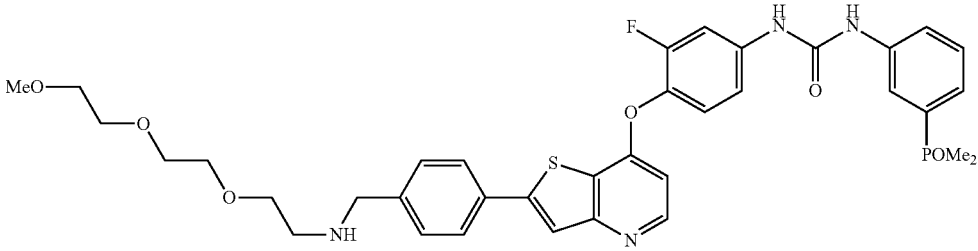<br>1-(4-(2-(4-5,8,11-trioxa-2-azadodecylphenyl)thieno[3,2-b]pyridin-7-yloxy)-3-fluorophenyl)-3-(3-(dimethylphosphoryl)phenyl)urea<br>$^1$H NMR (DMSO-d6) δ (ppm): 9.14 (s, 1H), 9.07 (s, 1H), 8.51 (d, J = 5.6 Hz, 1H), 8.03 (s, 1H), 7.90-7.81 (m, 2H), 7.77 (dd, J = 13.2, 2.4 Hz, 1H), 7.64 (d, J = 8.0 Hz, 1H), 7.50-7.41 (m, 3H), 7.36 (dd, J = 11.2, 7.6 Hz, 1H), 7.29 (d, J = 8.8 Hz, 1H), 6.62 (d, J = 5.6 Hz, 1H), 3.77 (s, 2H), 3.53-3.46 (m, 6H), 3.44-3.36 (m, 2H), 3.22 (s, 3H), 2.66 (t, J = 5.6 Hz, 2H), 1.64 (d, J = 13.2 Hz, 6H).<br>LRMS(ESI): (calc.) 706.24 (found) 354.3 (M + 2/2) |
| 434 | 281 | 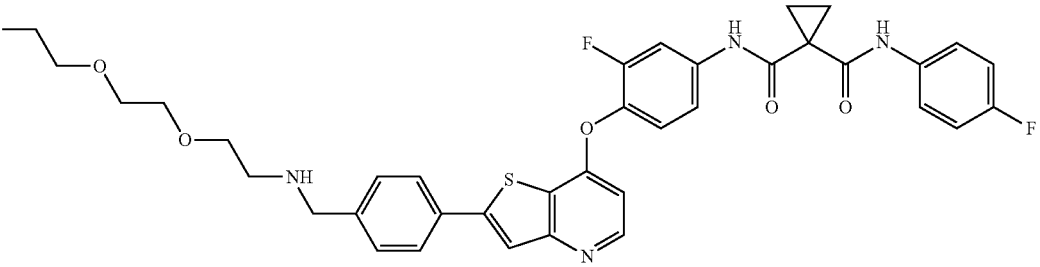<br>N-(4-(2-(4-5,8,11-trioxa-2-azadodecylphenyl)thieno[3,2-b]pyridin-7-yloxy)-3-fluorophenyl)-N-(4-fluorophenyl)cyclopropane-1,1-dicarboxamide<br>$^1$H NMR (DMSO-d$_6$) δ (ppm): 10.42 (s, 1H); 10.02 (s, 1H); 8.50 (d, J = 5.5, 1H); 8.02 (s, 1H); 7.91 (dd, J = 13.1, 2.2, 1H); 7.83 (d, J = 8.2, 2H); 7.65-7.62 (m, 2H); 7.53-7.44 (m, 4H); 7.18-7.13 (m, 2H); 6.60 (d, J = 5.5, 1H); 3.77 (s, 2H); 3.52-3.44 (m, 8H); 3.42-3.39 (m, 2H); 3.22 (s, 3H); 2.65 (t, J = 5.7, 2H); 1.48-1.45 (m, 4H).<br>LRMS(ESI): (calc.) 716.8 (found) 717.6 (MH)+ |
| 435 | 282 | 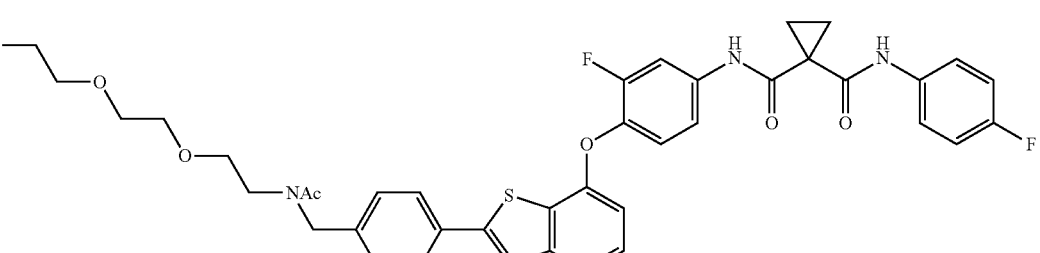<br>N-(4-(2-(4-(2-acetyl-5,8,11-trioxa-2-azadodecyl)phenyl)thieno[3,2-b]pyridin-7-yloxy)-3-fluorophenyl)-N-(4-fluorophenyl)cyclopropane-1,1-dicarboxamide<br>$^1$H NMR (DMSO-d$_6$) δ (ppm): 10.42 (s, 1H); 10.02 (s, 1H); 8.51 (d, J = 5.5, 0.4H); 8.50 (d, J = 5.5, 0.6H); 8.06 (s, 0.4H); 8.04 (s, 0.6H); 7.94-7.82 (m, 3H); 7.66-7.62 (m, 2H); 7.54-7.44 (m, 2H); 7.35 (d, J = 8.2, 2H); 7.18-7.13 (m, 2H); 6.62-6.59 (m, 1H); 4.70 (s, 0.7H); 4.60 (s, 1.3H); 3.55-3.40 (m, 12H); 3.23 (s, 3H); 2.13 (s, 2.1H); 2.03 (s, 0.9H); 1.46 (s, 4H).<br>LRMS(ESI): (calc.) 758.8 (found) 391.2 (M + H + Na/2)+ |

TABLE 4-continued

| Cpd | Ex | Structure and Characterization |
|---|---|---|
| 436 | 283 | 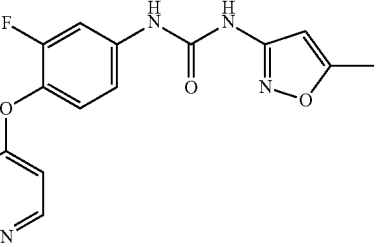<br>1-(4-(2-(4-5,8,11-trioxa-2-azadodecylphenyl)thieno[3,2-b]pyridin-7-yloxy)-3-fluorophenyl)-3-(5-methylisoxazol-3-yl)urea<br>$^1$H NMR (DMSO-$d_6$) δ (ppm): 9.71 (s, 1H); 9.31 (s, 1H); 8.48 (d, J = 5.5, 1H); 8.01 (s, 1H); 7.82-7.79 (m, 2H); 7.73 (dd, J = 13.1, 2.5, 1H)7.46-7.41 (m, 3H); 7.28-7.26 (m, 1H); 6.60 (d, J = 5.5, 1H); 6.54 (d, J = 0.8, 1H); 3.75 (s, 2H); 3.51-3.45 (m, 8H); 3.41-3.35 (m, 2H); 3.20 (s, 3H); 2.63 (t, J = 5.7, 2H); 2.35 (d, J = 0.6, 3H).<br>LRMS(ESI): (calc.) 635.7 (found) 636.5 (MH)+ |

Additional compounds according to the present invention include those in Table 5

TABLE 5

| Cpd | Ex | Structure and Characterization |
|---|---|---|
| 437 | 284 | 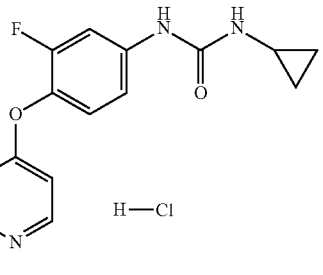<br>1-cyclopropyl-3-(3-fluoro-4-(2-(5-((2-methoxyethylamino)methyl)pyridin-2-yl)thieno[3,2-b]pyridin-7-yloxy)phenyl)urea hydrochloride<br>(DMSO) d(ppm) 1H: 9.55 (br, 2H), 9.38 (br, 1H), 8.82 (s, 1H), 8.72 (d, J = 6.0 Hz, 1H), 8.47 (s, 1H), 8.45 (d, J = 8.4 Hz, 1H), 8.23 (d, J = 7.8 Hz, 1H), 7.78 (dd, J = 13.5, 2.1 Hz, 1H), 7.44 (t, J = 9.3 Hz, 1H), 7.23 (d, J = 8.1 Hz, 1H), 6.97-6.92 (m, 1H), 6.82 (br, 1H), 4.35-4.20 (m, 2H), 3.66 (t, J = 5.1 H, 2H), 3.32 (s, 3H), 3.19-3.11 (m, 2H), 2.60-2.52 (m, 1H), 0.69-0.62 (m, 2H), 0.45-0.39 (m, 2H). |
| 439 | 286 | 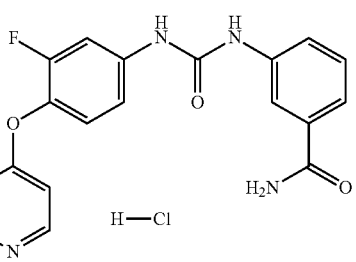<br>3-(3-(3-fluoro-4-(2-(5-((2-methoxyethylamino)methyl)pyridin-2-yl)thieno[3,2-b]pyridin-7-yloxy)phenyl)ureido)benzamide hydrochloride<br>(DMSO) d(ppm) 1H: 9.75 (s, 1H), 9.39 (br, 3H), 8.79 (d, J = 1.8 Hz, 1H), 8.67 (d, J = 6.0 Hz, 1H), 8.45 (s, 1H), 8.42 (d, J = 8.4 Hz, 1H), 8.18 (dd, J = 8.1, 2.4 Hz, 1H), 7.94 (br, 2H), 7.81 (dd, J = 13.5, 2.7 Hz, 1H), 7.65 (dd, J = 7.8, 1.5 Hz, 1H), 7.53-7.46 (m, 2H), 7.39-7.27 (m, 3H), 6.89 (d, J = 5.7 Hz, 1H), 4.40-4.21 (m, 2H), 3.65 (t, J = 5.1 Hz, 2H), 3.32 (s, 3H), 3.20-3.12 (m, 2H). |

| Cpd | Ex | Structure and Characterization |
|---|---|---|
| 440 | 287 | 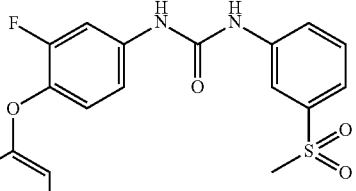
1-(3-fluoro-4-(2-(5-((2-methoxyethylamino)methyl)pyridin-2-yl)thieno[3,2-b]pyridin-7-yloxy)phenyl)-3-(3-(methylsulfonyl)phenyl)urea hydrochloride
(DMSO) d(ppm) 1H: 9.73 (s, 1H), 9.70 (s, 1H), 9.30 (br, 2H), 8.77 (s, 1H), 8.64 (d, J = 5.7 Hz, 1H), 8.44 (s, 1H), 8.40 (d, J = 8.4 Hz, 1H), 8.18-8.14 (m, 2H), 7.80 (dd, J = 13.5, 2.7 Hz, 1H), 7.69-7.67 (m, 1H), 7.61-7.43 (m, 3H), 7.30 (d, J = 9.3 Hz, 1H), 6.84 (d, J = 5.7 Hz, 1H), 4.30-4.25 (m, 2H), 3.64 (t, J = 5.1 Hz, 2H), 3.32 (s, 3H), 3.21 (s, 3H), 3.19-3.12 (m, 2H). |
| 441 | 288 | 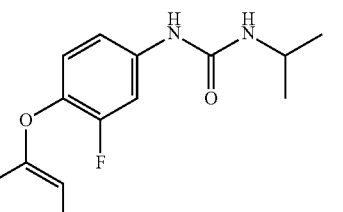
1-(3-fluoro-4-(2-(5((2-methoxyethylamino)methyl)-1-methyl-1H-imidazol-2-yl)thieno[3,2-b]pyridin-7-yloxy)phenyl)-3-isopropylurea
(DMSO) d(ppm) 1H: 8.70 (s, 1H), 8.51 (d, J = 5.7 Hz, 1H), 7.89 (s, 1H), 7.71 (dd, J = 2.4, 13.8 Hz, 1H), 7.37 (t, J = 9.0 Hz, 1H), 7.15-7.10 (m, 1H), 6.96 (s, 1H), 6.65 (d, J = 5.1 Hz, 1H), 6.17 (d, J = 7.8 Hz, 1H), 3.92 (s, 3H), 3.83-3.72 (m, 1H), 3.77 (s, 2H), 3.41 (t, 5.4 Hz, 2H), 3.25 (s, 3H), 2.70 (t, J = 5.4 Hz, 2H), 1.11 (d, J = 6.6 Hz, 6H). |
| 442 | 289 | 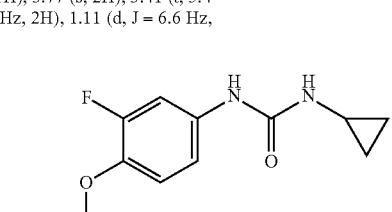
1-cyclopropyl-3-(3-fluoro-4-(2-(5-((2-(2-methoxyethoxy)ethylamino)methyl)pyridin-2-yl)thieno[3,2-b]pyridin-7-yloxy)phenyl)urea
(DMSO) d(ppm) 1H: 9.00 (s, 1H), 8.58 (d, J = 1.8 Hz, 1H), 8.52 (d, J = 5.4 Hz, 1H), 8.32 (s, 1H), 8.23 (d, J = 8.4 Hz, 1H), 7.90 (dd, J = 8.1, 1.8 Hz, 1H), 7.74 (dd, J = 13.5, 2.1, 1H), 7.38 (t, J = 8.7 Hz, 1H), 7.22 (d, J = 9.9 Hz, 1H), 6.84 (s, 1H), 6.64 (d, J = 5.7 Hz, 1H), 3.79 (s, 2H), 3.54-3.40 (m, 6H), 3.24 (s, 3H), 2.66 (t, J = 5.7 Hz, 2H), 2.57-2.51 (m, 1H), 0.68-0.61 (m, 2H), 0.45-0.40 (m, 2H). |

Pharmaceutical Compositions

In some embodiments, the invention provides pharmaceutical compositions comprising a compound according to the invention and a pharmaceutically acceptable carrier, excipient, or diluent. Compositions of the invention may be formulated by any method well known in the art and may be prepared for administration by any route, including, without limitation, parenteral, oral, sublingual, transdermal, topical, intranasal, intratracheal, or intrarectal. In some embodiments, compositions of the invention are administered intravenously in a hospital setting. In some embodiments, administration may be by the oral route.

The characteristics of the carrier, excipient or diluent will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

The active compound is included in the pharmaceutically acceptable carrier, excipient or diluent in an amount sufficient to deliver to a patient a therapeutically effective amount without causing serious toxic effects in the patient treated. The effective dosage range of a pharmaceutically acceptable derivative can be calculated based on the weight of the parent compound to be delivered. If the derivative exhibits activity in itself, the effective dosage can be estimated as above using the weight of the derivative, or by other means known to those skilled in the art.

Inhibition of VEGF Receptor Signaling

In some embodiments the invention provides a method of inhibiting VEGF receptor signaling in a cell, comprising contacting a cell in which inhibition of VEGF receptor signaling is desired with an inhibitor of VEGF receptor signaling according to the invention. Because compounds of the invention inhibit VEGF receptor signaling, they are useful research tools for in vitro study of the role of VEGF receptor signaling in biological processes.

In some embodiments, inhibiting VEGF receptor signaling causes an inhibition of cell proliferation of the contacted cells.

ASSAY EXAMPLES

Inhibition of VEGF Activity

The following protocol was used to assay the compounds of the invention.

Assay Example 1

In Vitro Receptor Tyrosine Kinase Assay (VEGF Receptor KDR)

This test measures the ability of compounds to inhibit the enzymatic activity of recombinant human VEGF receptor enzymatic activity.

A 1.6-kb cDNA corresponding to the catalytic domain of VEGFR2 (KDR) (Genbank accession number AF035121 amino acid 806 to 1356) is cloned into the Pst I site of the pDEST20 Gateway vector (Invitrogen) for the production of a GST-tagged version of that enzyme. This constuct is used to generate recombinant baculovirus using the Bac-to-Bac™ system according to the manucfacturer's instructions (Invitrogen).

The GST-VEGFR2806-1356 protein is expressed in Sf9 cells (*Spodoptera frugiperda*) upon infection with recombinant baculovirus construct. Briefly, Sf9 cells grown in suspension and maintained in serum-free medium (Sf900 II supplemented with gentamycin) at a cell density of about 2×10⁶ cells/ml are infected with the above-mentioned viruses at a multiplicity of infection (MOI) of 0.1 during 72 hours at 27° C. with agitation at 120 rpm on a rotary shaker. Infected cells are harvested by centrifugation at 398 g for 15 min. Cell pellets are frozen at −80° C. until purification is performed.

All steps described in cell extraction and purification are performed at 4° C. Frozen Sf9 cell pellets infected with the GST-VEGFR2806-1356 recombinant baculovirus are thawed and gently resuspended in Buffer A (PBS pH 7.3 supplemented with 1 µg/ml pepstatin, 2 µg/ml Aprotinin and leupeptin, 50 µg/ml PMSF, 50 µg/ml TLCK and 10 µM E64 and 0.5 mM DTT) using 3 ml of buffer per gram of cells. Suspension is Dounce homogenized and 1% Triton X-100 is added to the homogenate after which it is centrifuged at 22500 g, 30 min., 4° C. The supernatant (cell extract) is used as starting material for purification of GST-VEGFR2806-1356.

The supernatant is loaded onto a GST-agarose column (Sigma) equilibrated with PBS pH 7.3. Following a four column volume (CV) wash with PBS pH 7.3+1% Triton X-100 and 4 CV wash with buffer B (50 mM Tris pH 8.0, 20% glycerol and 100mM NaCl), bound proteins are step eluted with 5 CV of buffer B supplemented with 5 mM DTT and 15 mM glutathion. GST-VEGFR2806-1356 enriched fractions from this chromatography step are pooled based on U.V. trace i.e. fractions with high O.D.280. Final GST-VEGFR2806-1356 protein preparations concentrations are about 0.7 mg/ml with purity approximating 70%. Purified GST-VEGFR2806-1356 protein stocks are aliquoted and frozen at −80° C. prior to use in enzymatic assay.

Inhibition of VEGFR/KDR is measured in a DELFIA™ assay (Perkin Elmer). The substrate poly(Glu4, Tyr) is immobilized onto black high-binding polystyrene 96-well plates. The coated plates are washed and stored at 4° C. During the assay, the enzyme is pre-incubated with inhibitor and Mg-ATP on ice in polypropylene 96-well plates for 4 minutes, and then transferred to the coated plates. The subsequent kinase reaction takes place at 30° C. for 10-30 minutes. ATP concentrations in the assay are 0.6 uM for VEGFR/KDR (2× the Km). Enzyme concentration is 5 nM. After incubation, the kinase reactions are quenched with EDTA and the plates are washed. Phosphorylated product is detected by incubation with Europium-labeled anti-phosphotyrosine MoAb. After washing the plates, bound MoAb is detected by time-resolved fluorescence in a Gemini SpectraMax reader (Molecular Devices). Compounds are evaluated over a range of concentrations and IC50's (concentration of compounds giving 50% inhibition of enzymatic activity) are determined. The results are shown in Table 6. In the table, "a" indicates inhibitory activity at a concentration of less than 250 nanomolar; "b" indicates inhibitory activity at a concentration ≥250 but <500 nanomolar, "c" indicates inhibitory activity at ≥500 but <1000 nanomolar; and "d" indicates inhibitory activity ≥1000 nanomolar.

Assay Example 2

VEGF-Dependent Erk Phosphorylation

Cells and Growth Factor:

HUVEC cells were purchased from Cambrex Bio Science Walkersville, Inc and cultured according to the vendor's instructions. The full-length coding sequence of $VEGF_{165}$ was cloned using the Gateway Cloning Technology (Invitrogen) for baculovirus expression Sf9 cells. $VEGF_{165}$ was purified from conditioned media using a NaCl gradient elution from a HiTrap heparin column (GE Healthcare Life Sciences) followed by an imidazole gradient elution from a HiTrap chelating column (GE Healthcare Life Sciences), then buffer stored in PBS supplemented with 0.1% BSA and filter sterilized Cell Assays:

Cells were seeded at 8000 cells/well of a 96 wells plate and grown for 48 hours. Cells were then grown overnight in serum and growth factor-free medium and exposed for 1.5 h to compounds dilutions. Following a 15 min incubation in medium, VEGF$_{165}$ (150 ng/ml) cells were lysed in ice-cold lysis buffer (50 mM HEPES, pH 7.4, 150 mM NaCl, 1.5 mM MgCl$_2$, 1% Triton X-100, 10% glycerol) containing 1 mM 4-(2 aminoethyl)benzenesulfonyl fluoride hydrochloride, 200 µM sodium orthovanadate, 1 mM sodium fluoride, 10 µg/mL leupeptin, 10 µg/mL aprotinin, 1 µg/mL pepstatin and 50 µg/mL Na-p-tosyl-L-lysine chloromethyl ketone hydrochloride and processed as Western blots to detect anti-phospho ERK1/2 (T202/Y204) (Cell Signaling Technologies).

Western Blot Analysis:

lysates samples from single treatment wells were separated on 5-20% SDS-PAGE gels and immunobloting was performed using Immobilon polyvinylidene difluoride membranes (Amersham) according to the manufacturer's instructions. The blots were washed in Tris-buffered saline with 0.1% Tween 20 detergent (TBST) and probed for antibodies against phospho-Thr202/Tyr204-ERK (Cell signaling technologies. Chemiluminescence detection (Amersham, ECL plus) was performed according to the manufacturer's instructions using a Storm densitometer (GE Healthcare; 800 PMT, 100 nM resolution) for imaging and densitometry analysis. Values of over the range of dilution were used to prepare IC$_{50}$ curves using a 4-parameter fit model. These curves were calculated using GraFit 5.0 software. The results are shown in Table 6. In the table, "a" indicates inhibitory activity at a concentration of less than 250 nanomolar; "b" indicates inhibitory activity at a concentration ≥250 but <500 nanomolar, "c" indicates inhibitory activity at ≥500 but <1000 nanomolar; and "d" indicates inhibitory activity ≥1000 nanomolar.

TABLE 6

| Compound | VEGFR2 IC50 (mM) | VEGF-dependent Erk phosphorylation IC50 (mM) |
|---|---|---|
| (structure) | a | a |
| (structure) | a | a |
| (structure) | a | a |

TABLE 6-continued

| Compound | VEGFR2 IC50 (mM) | VEGF-dependent Erk phosphorylation IC50 (mM) |
|---|---|---|
| | a | a |
| | a | a |
| | a | a |
| | a | a |
| | a | a |

TABLE 6-continued

| Compound | VEGFR2 IC50 (mM) | VEGF-dependent Erk phosphorylation IC50 (mM) |
|---|---|---|
| (structure) | a | a |
| (structure) | a | a |
| (structure) | b | |
| (structure) | a | |
| (structure) | a | |

TABLE 6-continued

| Compound | VEGFR2 IC50 (mM) | VEGF-dependent Erk phosphorylation IC50 (mM) |
|---|---|---|
| (structure) | d | a |
| (structure) | a | a |
| (structure) | b | a |
| (structure) | d | a |
| (structure) | a | a |

TABLE 6-continued

| Compound | VEGFR2 IC50 (mM) | VEGF-dependent Erk phosphorylation IC50 (mM) |
|---|---|---|
| | c | a |
| | a | a |
| | a | a |
| | a | a |
| | a | a |

TABLE 6-continued

| Compound | VEGFR2 IC50 (mM) | VEGF-dependent Erk phosphorylation IC50 (mM) |
|---|---|---|
| | a | a |
| | a | a |
| | b | a |
| | a | a |

TABLE 6-continued

| Compound | VEGFR2 IC50 (mM) | VEGF-dependent Erk phosphorylation IC50 (mM) |
|---|---|---|
| | a | a |
| | c | a |
| | a | a |
| | a | a |

TABLE 6-continued

| Compound | VEGFR2 IC50 (mM) | VEGF-dependent Erk phosphorylation IC50 (mM) |
|---|---|---|
| | a | a |
| | a | a |
| | a | a |
| | a | |

TABLE 6-continued

| Compound | VEGFR2 IC50 (mM) | VEGF-dependent Erk phosphorylation IC50 (mM) |
|---|---|---|
| (structure) | a | a |

Assay Example 3

In Vivo Solid Tumor Disease Model

This test measures the capacity of compounds to inhibit solid tumor growth.

Tumor xenografts are established in the flank of female athymic CD1 mice (Charles River Inc.), by subcutaneous injection of 1×106 U87, A431 or SKLMS cells/mouse. Once established, tumors are then serially passaged s.c. in nude mice hosts. Tumor fragments from these host animals are used in subsequent compound evaluation experiments. For compound evaluation experiments female nude mice weighing approximately 20 g are implanted s.c. by surgical implantation with tumor fragments of ~30 mg from donor tumors. When the tumors are approximately 100 mm3 in size (~7-10 days following implantation), the animals are randomized and separated into treatment and control groups. Each group contains 6-8 tumor-bearing mice, each of which is ear-tagged and followed individually throughout the experiment.

Mice are weighed and tumor measurements are taken by calipers three times weekly, starting on Day 1. These tumor measurements are converted to tumor volume by the well-known formula (L+W/4)3 4/3π. The experiment is terminated when the control tumors reach a size of approximately 1500 mm$^3$. In this model, the change in mean tumor volume for a compound treated group/the change in mean tumor volume of the control group (non-treated or vehicle treated)×100 (AT/AC) is subtracted from 100 to give the percent tumor growth inhibition (% TGI) for each test compound. In addition to tumor volumes, body weight of animals is monitored twice weekly for up to 3 weeks

Assay Example 4

In vivo Choroidal Neovascularization (CNV) Model

This test measures the capacity of compounds to inhibit CNV progression. CNV is the main cause of severe vision loss in patients suffering from age-related macular degeneration (AMD).

Male Brown-Norway rats (Japan Clea Co., Ltd.) were used in these studies.

Rats were anesthetized by intraperitoneal injection of pentobarbital, and the right pupil was dilated with 0.5% tropicamide and 0.5% phenylephrine hydrochloride. The right eye received 6 laser burns between retinal vessels using a slit lamp delivery system of Green laser Photocoagulator (Nidex Inc., Japan), and microscope slide glass with Healon™ (AMO Inc) used as a contact lens. The laser power was 100 or 200 mW for 0.1 second and spot diameter was 100 µm. At the time of laser burn, bubble production was observed, which is an indication of rupture of Bruch's membrane which is important for CNV generation.

Rats were divided into the groups based on their body weight using SAS software (SAS institute Japan, R8.1) after laser irradiation (Day 0). After animals were anesthetized, and the right pupil dilated (as above mentioned), the right eye of the animal received the compound or vehicle by an injection (10 µL/eye) at doses of 30 nmol/eye on Day 3. The compounds were dissolved or suspended in CBS, PBS, or other adequate vehicles before injection.

On Day 10, the animals were anesthetized with ether, and high molecular weight fluorescein isothiocyanate (FITC)-dextran (SIGMA, 2×10$^6$ MW) was injected via a tail vein (20 mg/rat). About 30 min after FITC-dextran injection, animals were euthanized by ether or carbon dioxide, and the eyes were removed and fixed with 10% formaline neutral buffer solution. After over 1 hour of fixation, RPE-choroid-sclera flat mounts were obtained by removing cornea, lens and retina from the eyeballs. The flat mounts were mounted in 50% glycerol on a microscope slide, and the portion burned by laser was photographed using a fluorescence microscope (Nikon Corporation, excitation filter: 465-495 nm, absorption filter: 515-555 nm). The CNV area was obtained by measurement of hyper-fluorescence area observed on the photograph using Scion image.

The average CNV area of 6 burns was used as an individual value of CNV area, and the average CNV area of compound treated group was compared with that of the vehicle-treated group. Results with some compounds of the present invention are shown in Table 7 and are indicated as % of inhibition of CNV progression ("A" indicates greater than or equal to 60% inhibition, and "B" indicates ≥40% to <60% inhibition).

TABLE 7

| Cpd. No. (EX. No.) | Inhibition of CNV progression |
|---|---|
| 315(202) | A |
| 323(203) | A |
| 324(204) | B |
| 331(205) | B |
| 333(207) | A |
| 335(209) | B |
| 341(212) | A |
| 348(215) | B |
| 349(215) | A |
| 351(216) | B |
| 387(235) | B |
| 390(238) | B |
| 392(240) | B |
| 397(245) | B |
| 403(251) | A |
| 413(261) | A |
| 414(262) | B |
| 419(267) | B |
| 434(282) | A |

What is claimed is:

1. A compound selected from the group consisting of

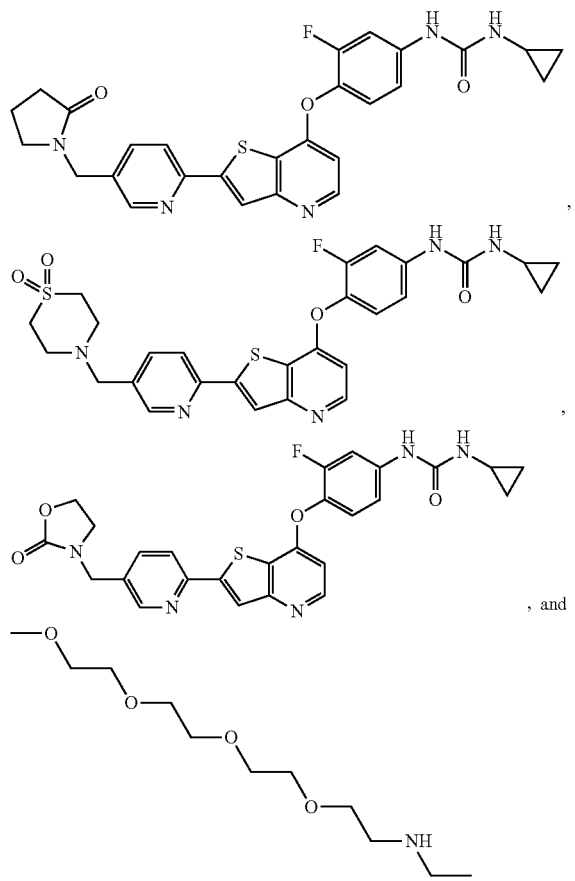

, and and pharmaceutically acceptable salts thereof.

2. The compound according to claim 1, wherein the compound is

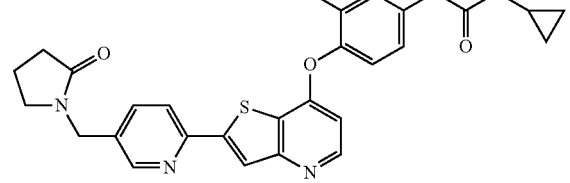

3. The compound according to claim 1, wherein the compound is

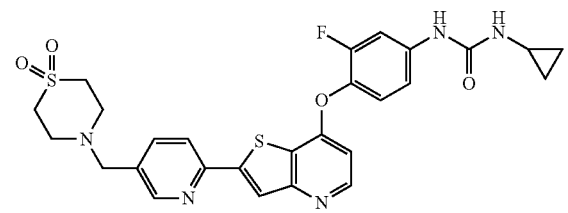

4. The compound according to claim 1, wherein the compound is

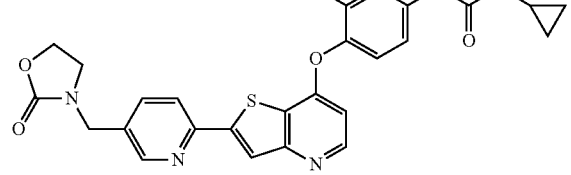

5. The compound according to claim 1, wherein the compound is

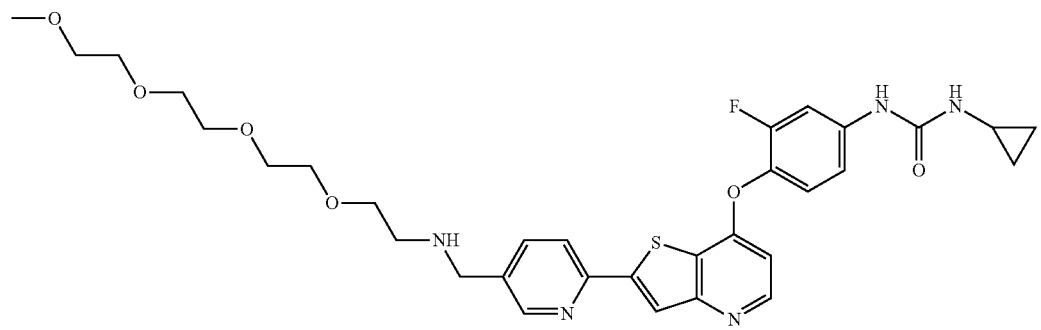 [SMILES: COCCOCCOCCOCCNCc1ccc(-c2cc3nccc(Oc4ccc(NC(=O)NC5CC5)cc4F)c3s2)nc1]

6. A composition comprising a compound according to claim 1, and a pharmaceutically acceptable carrier.

7. The composition according to claim 6, wherein the compound is

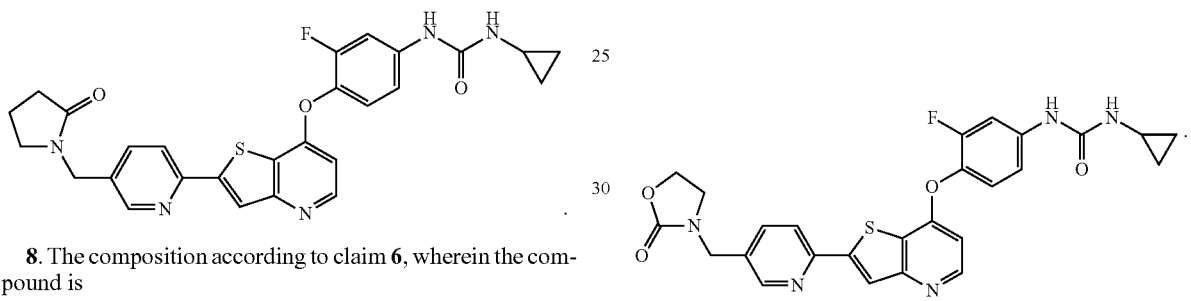

8. The composition according to claim 6, wherein the compound is

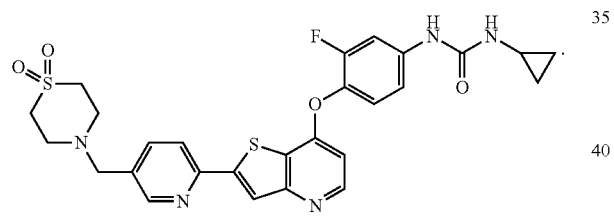

9. The composition according to claim 6, wherein the compound is

10. The composition according to claim 6, wherein the compound is

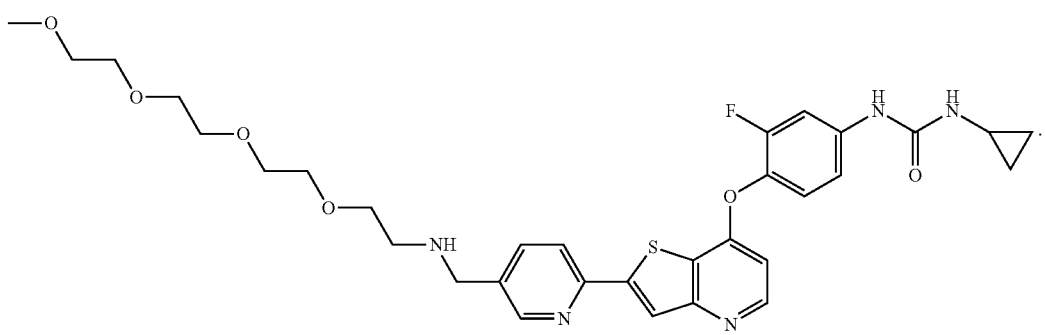 [SMILES: COCCOCCOCCOCCNCc1ccc(-c2cc3nccc(Oc4ccc(NC(=O)NC5CC5)cc4F)c3s2)nc1]

* * * * *